US009718888B2

(12) United States Patent
Magliery et al.

(10) Patent No.: US 9,718,888 B2
(45) Date of Patent: Aug. 1, 2017

(54) METHODS AND COMPOSITIONS RELATED TO SINGLE CHAIN ANTIBODY FRAGMENTS THAT BIND TO TUMOR-ASSOCIATED GLYCOPROTEIN 72 (TAG-72)

(71) Applicant: Ohio State Innovation Foundation, Columbus, OH (US)

(72) Inventors: Thomas J. Magliery, Columbus, OH (US); Brandon J. Sullivan, Gahanna, OH (US); Heather C. Allen, Columbus, OH (US); Edward W. Martin, Delaware, OH (US); Charles L. Hitchcock, Arlington, OH (US); E. David Alten, Loveland, OH (US); Nicholas E. Long, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/907,368

(22) PCT Filed: Jul. 23, 2014

(86) PCT No.: PCT/US2014/047854
§ 371 (c)(1),
(2) Date: Jan. 25, 2016

(87) PCT Pub. No.: WO2015/013429
PCT Pub. Date: Jan. 29, 2015

(65) Prior Publication Data

US 2016/0176979 A1 Jun. 23, 2016

Related U.S. Application Data

(60) Provisional application No. 61/857,511, filed on Jul. 23, 2013.

(51) Int. Cl.

| | |
|---|---|
| ***C07K 16/30*** | (2006.01) |
| ***A61K 51/10*** | (2006.01) |
| ***C12N 15/62*** | (2006.01) |
| ***C12N 15/70*** | (2006.01) |
| ***C12N 15/79*** | (2006.01) |
| ***C12N 1/21*** | (2006.01) |
| ***C12N 15/13*** | (2006.01) |
| ***A61K 39/395*** | (2006.01) |
| ***G01N 33/563*** | (2006.01) |
| ***G01N 33/574*** | (2006.01) |
| ***G01N 33/573*** | (2006.01) |
| ***G01N 33/58*** | (2006.01) |
| ***C12N 5/09*** | (2010.01) |
| ***A61K 45/06*** | (2006.01) |
| ***A61K 47/48*** | (2006.01) |
| ***A61N 5/10*** | (2006.01) |
| *C12N 15/86* | (2006.01) |
| *C12N 15/66* | (2006.01) |
| *C12N 5/10* | (2006.01) |

(52) U.S. Cl.
CPC ........ *C07K 16/3076* (2013.01); *A61K 39/395* (2013.01); *A61K 45/06* (2013.01); *A61K 47/48569* (2013.01); *A61K 51/1045* (2013.01); *A61N 5/10* (2013.01); *C07K 16/3092* (2013.01); *C12N 5/0693* (2013.01); *C07K 2317/622* (2013.01); *C07K 2317/92* (2013.01); *C07K 2317/94* (2013.01); *C07K 2319/00* (2013.01); *C07K 2319/02* (2013.01); *C07K 2319/21* (2013.01); *C12N 5/10* (2013.01); *C12N 15/62* (2013.01); *C12N 15/66* (2013.01); *C12N 15/86* (2013.01); *C12N 2800/00* (2013.01); *G01N 2800/00* (2013.01)

(58) Field of Classification Search
None
See application file for complete search history.

(56) References Cited

U.S. PATENT DOCUMENTS

| | | | |
|---|---|---|---|
| 6,495,137 | B1 | 12/2002 | Mezes et al. |
| 7,179,899 | B2 | 2/2007 | Mezes et al. |
| 8,029,788 | B2 | 10/2011 | Kashmiri et al. |
| 8,119,132 | B2 | 2/2012 | Hong et al. |
| 2006/0171941 | A1 | 8/2006 | Kashmiri et al. |
| 2010/0183504 | A1 | 7/2010 | Chen |
| 2013/0052130 | A1 | 2/2013 | Davis |

OTHER PUBLICATIONS

Pavlinkova et al., Int. J. Cancer, 2001, 94:717-726.*
Goel et al., Biochim Biophys Acta, 2000, 1523:13-20.*
Bailey, Graham S. (1996) "The lodogen method for radiolabeling protein." The protein protocols handbook. Humana Press, 673-674.
Beresford, G. W. et al. (1999). Binding characteristics and tumor targeting of a covalently linked divalent CC49 single-chain antibody. International journal of cancer, 81(6), 911-917.
Bird, R. E. et al. (1988). Single-chain antigen-binding proteins. Science 242, 423-6.
Bork, P., Holm, L. & Sander, C. (1994). The immunoglobulin fold. Structural classification, sequence patterns and common core. J Mol Biol 242, 309-20.
Chen, K. C. et al. (2011). A humanized immunoenzyme with enhanced activity for glucuronide prodrug activation in the tumor microenvironment. Bioconjugate chemistry, 22(5), 938-948.
Chen, C., Constantinou, A., Deonarain, M. (2011) Modulating antibody pharmacokinetics using hydrophilic polymers. Exper Opin Drug Deliv 8, 1221-36.
Colcher, D., Hand, P. H., Nuti, M., & Schlom, J. (1981). A spectrum of monoclonal antibodies reactive with human mammary tumor cells. Proceedings of the National Academy of Sciences, 78(5), 3199-3203.

(Continued)

*Primary Examiner* — Hong Sang
(74) *Attorney, Agent, or Firm* — Meunier Carlin & Curfman LLC

(57) ABSTRACT

Disclosed herein are methods and compositions related to single chain antibody fragments which specifically bind sialyl-Tn epitope of tumor-associated glycoprotein 72 (TAG-72).

19 Claims, 30 Drawing Sheets

(56) References Cited

OTHER PUBLICATIONS

Colcher, D. et al. (1988). Radioimmunolocalization of human carcinoma xenografts with B72.3 second generation monoclonal antibodies. Cancer Res 48, 4597-603.

Colcher, D. et al. (1999). Single-chain antibodies in pancreatic cancer. Ann N Y Acad Sci 880, 263-80.

Denzin, L. K., Whitlow, M. & Voss, E. W., Jr. (1991). Single-chain site-specific mutations of fluorescein-amino acid contact residues in high affinity monoclonal antibody 4-4-20. J Biol Chem 266, 14095-103.

Divgi, C. R. et al. (1995). Phase I radioimmunotherapy trial with iodine-131-CC49 in metastatic colon carcinoma. J Nucl Med 36, 586-92.

Durani, V., Sullivan, B.J., Magliery, T.J. (2012) Simplifying protein expression with ligation-free, traceless and tag-switching plasmids. Protein Expr Purif 85, 9-17.

Goel, A., Colcher, D., Baranowska-Kortylewicz, et al. (2000) Genetically engineered tetravalent single-chain Fv of the pancarcinoma monoclonal antibody CC49: Improved biodistribution and potential for therapeutic application. Cancer Res 60, 6964-71.

Guadagni, Fiorella et al. (1996) Correlation between tumor associated glycoprotein 72 mucin levels in tumor and serum of colorectal patients as measured by the quantitative CA 72-4 immunoassay. Cancer Research 56(22), 5293-5298.

International Search Report and Written Opinion of the International Searching Authority from Application No. PCT/US2014/047854, mailed Oct. 28, 2014, 12 pages.

Jemal, A., Bray, F., Center, M. M., Ferlay, J., Ward, E. & Forman, D. (2011). Global cancer statistics. CA Cancer J Clin 61, 69-90.

Kashmiri, S. V. et al. (1995). Generation, characterization, and in vivo studies of humanized anticarcinoma antibody CC49. Hybridoma 14, 461-73.

Kjeldsen, T. (1988). Preparation and characterization of monoclonal antibodies directed to the tumor-associated O-linked sialosyl-2-6 alpha-N-acetylgalactosaminyl (sialosyl-Tn) epitope. Cancer Res 48, 2214-20.

Kortt, A.A., Dolezal, O., Power, B.E., Hudson, P.J. (2001). Dimeric and trimeric antibodies: high avidity scFv for cancer targeting. Biomol Eng 18, 95-108.

Lavinder, J. J., Hari, S. B., Sullivan, B. J. & Magliery, T. J. (2009). High-throughput thermal scanning: a general, rapid dye-binding thermal shift screen for protein engineering. J Am Chem Soc 131, 3794-5.

Maddalena, M. E. et al. (2009) 177Lu-AMBA biodistribution, radiotherapeutic efficacy, imaging, and autoradiography in prostate cancer models with low GRP-R expression. Journal of nuclear medicine : official publication, Society of Nuclear Medicine 50, 2017-24.

Milenic, D.E. et al. (1991) Construction, binding properties, metabolism, and tumor targeting of a single-chain Fv derived from the pancarcinoma monoclonal antibody CC49. Cancer Research 51, 6363-6371.

Miroux, B., Walker, J.E. (1996) Over-production of proteins in *Escherichia coli*: mutant hosts that allow synthesis of some membrane proteins and globular proteins at high levels. J Mol Biol 260, 289-98.

Muraro, R. et al. (1988). Generation and characterization of B72.3 second generation monoclonal antibodies reactive with the tumor-associated glycoprotein 72 antigen. Cancer Res 48, 4588-96.

Pantoliano, M. W. et al. (1991). Conformational stability, folding, and ligand-binding affinity of single-chain Fv immunoglobulin fragments expressed in *Escherichia coli*. Biochemistry, 30(42), 10117-10125.

Paus, E. B. et al. (1982) Radioiodination of proteins with the lodogen method. In Radioimmunoassay and Related Procedures in Medicine 1982: Proceedings of an International Symposium on Radioimmunoassay and Related Procedures in Medicine Organized by the International Atomic Energy Agency and Held in Vienna, Austria, Jun. 21-25, 1982. 161-171.

Pavlinkova, G. et al. (1999). Pharmacokinetics and biodistribution of engineered single-chain antibody constructs of MAb CC49 in colon carcinoma xenografts. J Nucl Med 40, 1536-46.

Pavlinkova, G. et al. (1999). Charge-modified single chain antibody constructs of monoclonal antibody CC49: generation, characterization, pharmacokinetics, and biodistribution analysis. Nucl Med Biol, 26, 27-34.

Pini, A. & Bracci, L. (2000). Phage display of antibody fragments. Curr Protein Pept Sci 1, 155-69.

Prachayasittikul, V. et al. (2007). EDTA-induced membrane fluidization and destabilization: biophysical studies on artificial lipid membranes. Acta Biochim Biophys Sin (Shanghai) 39, 901-13.

Sandhu, J. S. (1992). Protein engineering of antibodies. Crit Rev Biotechnol 12, 437-62.

Senisterra, G. A. & Finerty, P. J., Jr. (2009). High throughput methods of assessing protein stability and aggregation. Mol Biosyst 5, 217-23.

Son et al. (2009) Small animal PET imaging of recombinant single chain frgment variable of anti-TAG-72 humanized antibody in colon cancer xenograft model. J Nucl Med, 50, Supplement 2, 1592.

Sun, D. et al. (2007). Radioimmunoguided surgery (RIGS), PET/CT image-guided surgery, and fluorescence image-guided surgery: past, present, and future. J Surg Oncol 96, 297-308.

Thor, A. et al. (1986). Distribution of oncofetal antigen tumor-associated glycoprotein-72 defined by monoclonal antibody B72.3. Cancer Res 46, 3118-24.

Thor, A., Viglione, M. J., Muraro, R., Ohuchi, N., Schlom, J. & Gorstein, F. (1987). Monoclonal antibody B72.3 reactivity with human endometrium: a study of normal and malignant tissues. Int J Gynecol Pathol 6, 235-47.

Veronese, F.M., Mero, A. (2008) The impact of PEGylation on biological therapies. BioDrugs 22, 315-29.

Wedeking, P., and Tweedle, M. (1988) Comparison of the Biodistribution of Gd-153-Labeled Gd(Dtpa)2-, Gd(Dota)-, and Gd(Acetate)N in Mice. Nuclear medicine and biology 15, 395-402.

Yang, K., Basu, A., Wang, M., Chintala, R., Hsieh, M. C., Liu, S., Hua, J., Zhang, Z., Zhou, J., Li, M., Phyu, H., Petti, G., Mendez, M., Janjua, H., Peng, P., Longley, C., Borowski, V., Mehlig, M. & Filpula, D. (2003). Tailoring structure-function and pharmacokinetic properties of single-chain Fv proteins by site-specific PEGylation. Protein Eng 16, 761-70.

Yokota, T., Milenic, D. E., Whitlow, M. & Schlom, J. (1992). Rapid tumor penetration of a single-chain Fv and comparison with other immunoglobulin forms. Cancer Res 52, 3402-8.

Yoon, S. O. et al. (2006). Construction, affinity maturation, and biological characterization of an anti-tumor-associated glycoprotein-72 humanized antibody. J Biol Chem 281, 6985-92.

* cited by examiner

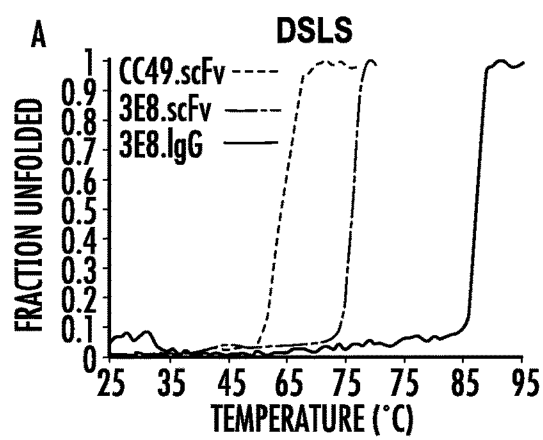
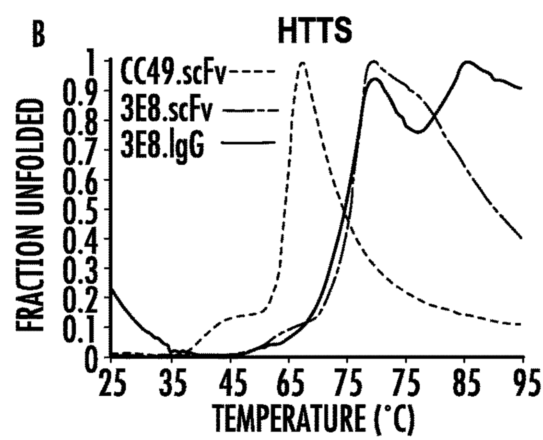
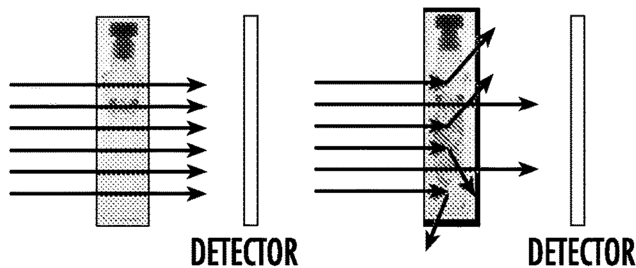
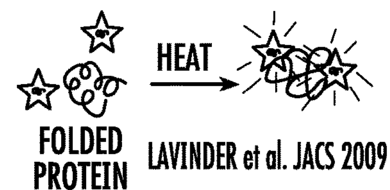
*FIG. 6A*
*FIG. 6B*

A

CC49.scFv

3E8.scFv

B

0 μm 0.25 μm 0.5 μm 1 μm 2 μm 4 μm 8 μm

3E8.scFv

3E8.IgG 0.25μm (-)* (-)**

SIMPLE BINDING ASSAY
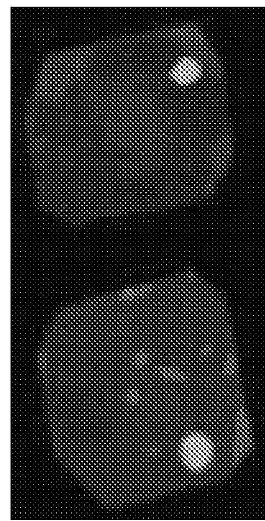
3E8.scFv BINDS TO THE PROPER SUBSTRATE
COMPETITION ELISA
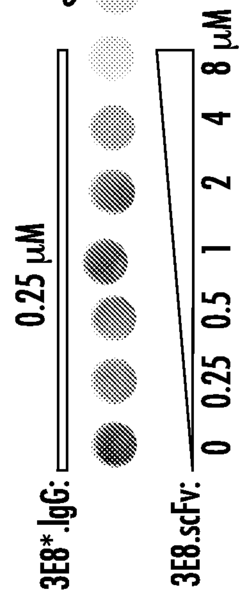
FIG. 14

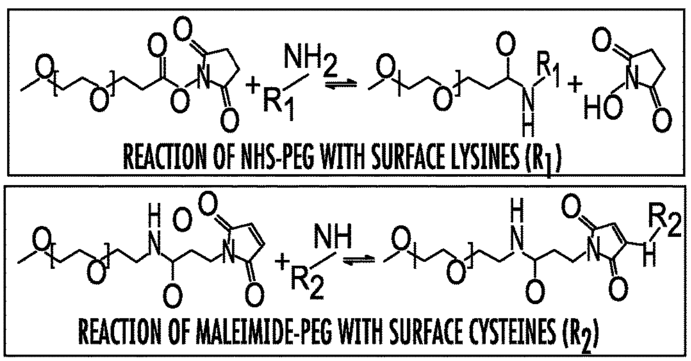

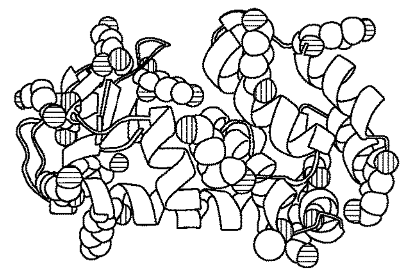

T4L WITH LYSINE RESIDUES SHOWN IN BLUE AND CYSTEINE RESIDUES SHOWN IN PINK

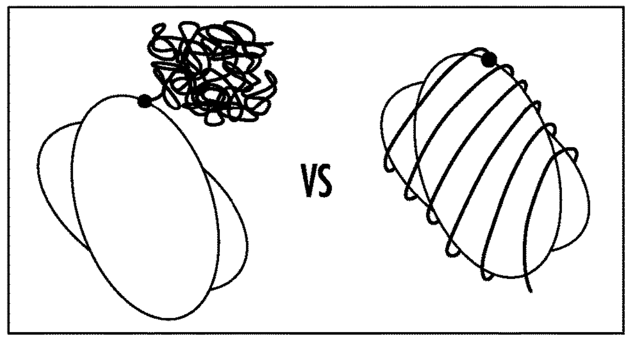

TWO HYPOTHESES ABOUT PEG-PROTEIN INTERACTION. LEHT: PEG FORMS POLYMER-LIKE BEAD NEAR ATTACHMENT. RIGHT: PEG WRAPS AROUND PROTEIN THREAD

SDS-PAGE OF PEGYLATION

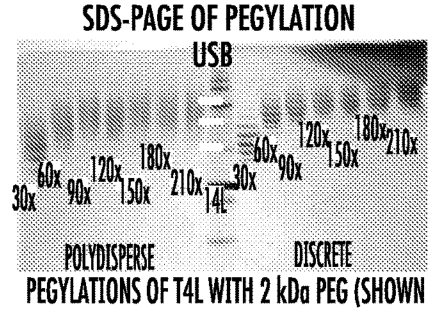

PEGYLATIONS OF T4L WITH 2 kDa PEG (SHOWN BELOW). POLYDISPERSE PEGs RESULT IN SMEAR OF PEGYLATED PRODUCTS; DISCRETE PEGs RESULT IN LADDER OF DISTINCT PEGYLATED PRODUCTS

FIG. 17

AT 60 °C, BOTH THE IgG AND scFv OF 3E8 ARE WELL FOLDED.

AT 70 °C, THE scFv IS COMPLETELY UNFOLDED, AS IS THE BINDING SITE OF THE IgG. THE CONSTANT DOMAINS OF THE IgG PREVENT AGGREGATION AT THIS TEMPERATURE.

BY 85 °C BOTH MOLECULES ARE UNFOLDED AND AGGREGATED.

METHODS AND COMPOSITIONS RELATED TO SINGLE CHAIN ANTIBODY FRAGMENTS THAT BIND TO TUMOR-ASSOCIATED GLYCOPROTEIN 72 (TAG-72)

CROSS-REFERENCE TO RELATED APPLICATIONS

This application claims benefit of U.S. Provisional Application No. 61/857,511, filed Jul. 23, 2013, which is hereby incorporated by reference in its entirety.

BACKGROUND

Greater than 10% of all deaths are caused by cancer; therefore, it is imperative that scientific research improves and innovates the state-of-the-art in prevention, diagnosis, imaging, therapeutics, and surgery (Jemal 2011). Traditional cancer imaging techniques rely on computed tomography (CT) and positron emission tomography (PET). Both methods suffer from poor resolution and weak signal-to-noise ratios. Radioimmunoguided detection and surgery (RIGS) is a powerful modality for accurately mapping the surfaces of cancerous tissue, but the current catalog of cancer-binding antibodies are not ideal for these applications (Sun 2007).

Several generations of monoclonal antibodies have been developed against the sialyl-Tn epitope. The first two, B72.3 (Thor 1986 and Thor 1987) and CC49 (Muraro 1988; Colcher 1988), entered clinical trials for radioimmunoguided surgery (RIGS), but a significant fraction of patients developed human anti-mouse antibodies (HAMA) (Dvigi 1995). In response, a humanized variant of CC49 was constructed (AKA) (Yoon 2006; Kashmiri 1995). None of the 21 patients experience HAMA when the procedure was performed with AKA, but the third generation antibody lost more than two-fold of its binding affinity. In 2008, Yoon et al. constructed a Fab library at CDR3 of AKA (Yoon 2006). This study yielded a Fab with improved binding that was later converted to a full-length IgG named 3E8.

The latest generation of sialyl-Tn IgGs (tumor-associated antigens) are nonimmunogenic and bind the sialyl-Tn epitope with remarkable affinity. However, in order to satisfy all the requirements for imaging, these full-length antibodies require reduction to the smaller scFv scaffold. This remaining step is nontrivial, which likely describes why these imaging agents are not common place in hospitals. The variable domains are stabilized by the constant domains which are void in the truncated scFv. Independently, the VH and VL domains are only weakly associated by noncovalent interactions (and possibly disulfide bonding), thus an amino acid linker is required to assemble the full antigen binding site. Often, these engineered proteins suffer from loss of affinity, heterogeneity in quaternary structure, and diminished stability. What is needed in the art is a dramatically stabilized 3E8 scFv.

SUMMARY

Disclosed herein is antibody fragment which specifically bind tumor-associated glycoprotein 72 (TAG-72). The antibody fragment can be a single chain variable antibody fragment (scFv). Disclosed herein are scFvs which bind the sialyl-Tn epitope of TAG-72. Examples include those found in SEQ ID NO: 1 and 2. The antibody fragment can comprises a heavy chain variable region comprising SEQ ID NO: 10, and a light chain variable region comprising SEQ ID NO: 11.

Also disclosed are nucleic acid sequences corresponding to the antibody fragments disclosed herein which specifically bind TAG-72. For example, disclosed are nucleic acid sequences SEQ ID NO: 7 and SEQ ID NO: 8.

Disclosed are compositions comprising the antibody fragments disclosed herein which specifically bind TAG-72 and a pharmaceutically acceptable carrier. Disclosed are compositions suitable for the treatment of cancer comprising a therapeutically effective amount of an antibody fragment which specifically binds TAG-72.

Further disclosed is a composition suitable for the in vivo or in vitro detection of cancer comprising a diagnostically effective amount of an antibody fragment which specifically binds TAG-72.

Disclosed is a method for in vivo treatment of a mammal having a TAG-72-expressing cancer comprising a step of administering to the mammal a therapeutically effective amount of a composition comprising an antibody fragment which specifically binds TAG-72.

Disclosed is a method for in vitro immunodetection of TAG-72-expressing cancer cells comprising a step of contacting the cancer cells with a composition suitable in vitro detection of cancer comprising a diagnostically effective amount of an antibody fragment which specifically binds TAG-72.

Also disclosed is a method for in vivo immunodetection of TAG-72-expressing cancer cells comprising a step of contacting the cancer cells with a composition suitable in vitro detection of cancer comprising a diagnostically effective amount of an antibody fragment of TAG-72.

Disclosed herein is a method of in vivo treatment of cancer comprising the steps of: (a) intravenously administering a radionuclide-labeled antibody fragment which specifically binds TAG-72; (b) thereafter detecting tumor cells using a radionuclide activity probe; and (c) thereafter removing the detected tumor cells by surgical excision.

Disclosed herein are kits comprising an antibody fragment which specifically binds TAG-72 and instructions for its use.

Disclosed are method of making an antibody fragment which specifically binds TAG-72, comprising: (a) culturing an isolated cell under conditions such that said antibody fragment is expressed; and (b) recovering said antibody fragment from the cell.

Also disclosed are methods of treating cancer comprising administering to a subject in need thereof a composition comprising an antibody fragment which specifically binds TAG-72, wherein the effector moiety is a chemotherapeutic agent.

Disclosed is a method for prognosing recurrence of cancer in a subject previously treated for the cancer, the method comprising: (a) isolating a biological sample comprising cells from a subject with a cancer; (b) contacting the biological sample with a composition comprising an antibody fragment under conditions sufficient for the composition to bind to an epitope present on a tumor and/or a cancer cell, if present, in the biological sample; and (c) identifying in the biological sample one or more cells that bind to the composition comprising an antibody fragment which specifically binds TAG-72, whereby recurrence of a cancer is prognosed in the subject.

DESCRIPTION OF DRAWINGS

FIG. 6 shows the stability of antibodies and fragments. A. Aggregation propensity is measured with increasing temperature. 3E8.scFv is intermediate in stability between the less stable CC49.scFv and the more stable 3E8.IgG. B. HTTS shows similar results to those reported by DSLS, with a second unfolding transition for 3E8.IgG. The binding domains of 3E8.scFv and 3E8.IgG both unfold at 66° C.

FIG. 14 shows binding studies for 3E8.scFv. An Estimated 50% bound at 4 μM i.e. 3E8.scFv is roughly a 16-fold worse binder than 3E8.IgG (KD=0.65 nM) so its estimated KD=10.4 nM.

FIG. 17 shows PEGylation results. PEGylations of T4L with 2 kDa PEG is shown. Polydispersed PEGs result in smear of PEGylated products; discrete PEGs result in ladder of distinct PEGylated products.

FIG. 22A: Model of 3E8.scFv—The complementary determining regions are the loops responsible for binding the antigen. The C-terminal cysteine is shown in blue spheres opposite the binding site. FIG. 22B: PEGylation increases the hydrodynamic radius of proteins, can reduce immunogenicity, decrease aggregation, and protect the antibody fragment from serum proteases.

DETAILED DESCRIPTION

Figure 1:
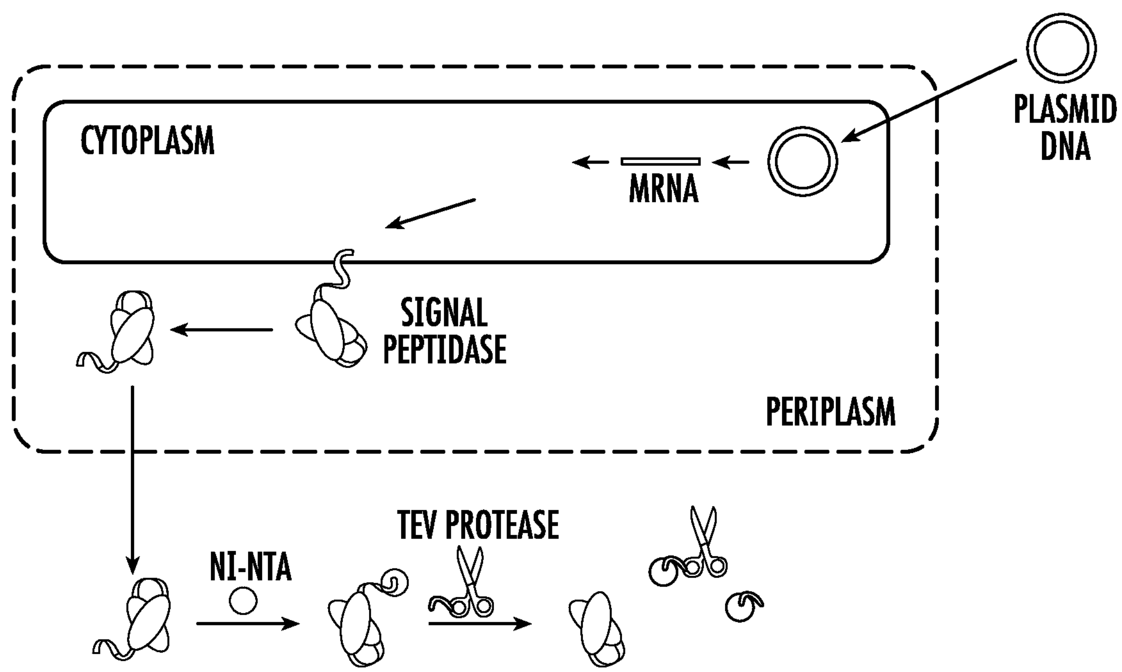
FIG. 1 shows a schematic describing the production, export and purification of scFv. Signal peptide shown in red with TEV cleavage site shown in blue. Note that the 6×His tag and TEV protease are removed by a second Ni-NTA agarose column.
Figure 2:
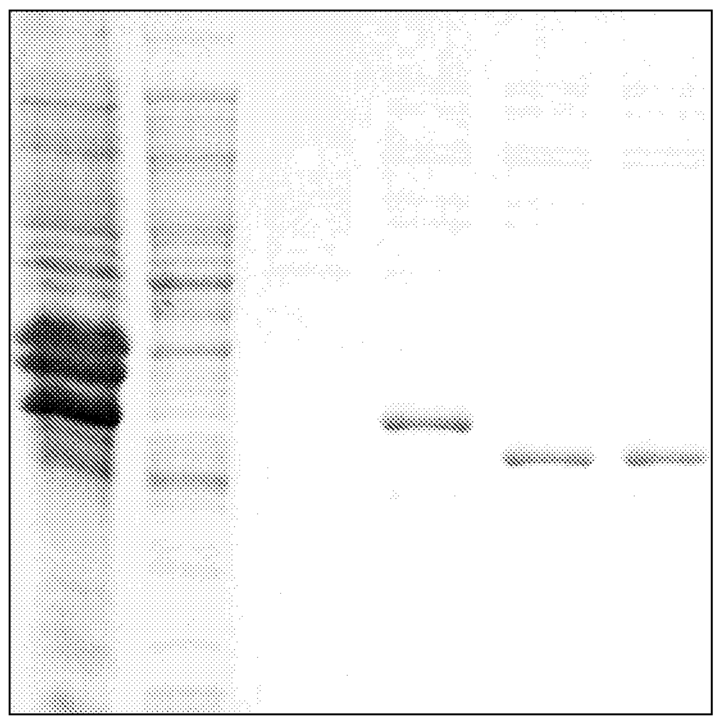
FIG. 2 shows sample purification of 3E8.scFv from pCOLD IV. Lane 1: Sphereoplasts, Lane 2: Periplasmic fraction after Ni-NTA binding, Lane 3: Wash, Lane 4: Eluted 6×His-TEV-3E8.scFv, Lane 5: 3E8.scFv after TEV protease cleavage to remove 6×His-tag, Lane 6: Ni-NTA purified protein after removal of TEV protease and 6×His-tag.

The materials, compositions, and methods described herein can be understood more readily by reference to the following detailed descriptions of specific aspects of the disclosed subject matter and the Examples and Figure included herein.

Before the present materials, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

DEFINITIONS

Unless defined otherwise, all technical and scientific terms used herein have the same meaning as commonly understood by one of ordinary skill in the art. Methods and materials similar or equivalent to those described herein can be used in the practice or testing of the present disclosure. In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "an antibody" includes mixtures of two or more such antibodies; reference to "the composition" includes mixtures of two or more such compositions, and the like.

"Optional" or "optionally" means that the subsequently described event or circumstance can or cannot occur, and that the description includes instances where the event or circumstance occurs and instances where it does not.

Unless otherwise indicated, all numbers expressing quantities of ingredients, reaction conditions, and so forth used in the specification and claims are to be understood as being modified in all instances by the term "about". The term "about", as used herein when referring to a measurable value such as an amount of mass, weight, time, volume, concentration, or percentage, is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods and/or employ the disclosed compositions. Accordingly, unless indicated to the contrary, the numerical parameters set forth in this specification and attached claims are approximations that can vary depending upon the desired properties sought to be obtained by the presently disclosed subject matter.

As used herein, the term "and/or" when used in the context of a list of entities, refers to the entities being present singly or in combination. Thus, for example, the phrase "A, B, C, and/or D" includes A, B, C, and D individually, but also includes any and all combinations and subcombinations of A, B, C, and D.

With respect to the terms "comprising", "consisting of, and "consisting essentially of, where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

The term "subject" as used herein refers to a member of any invertebrate or vertebrate species. Accordingly, the term "subject" is intended to encompass in some embodiments any member of the Kingdom Animalia including, but not limited to the phylum Chordata (e.g., members of Classes Osteichythyes (bony fish), Amphibia (amphibians), Reptilia (reptiles), Ayes (birds), and Mammalia (mammals), and all Orders and Families encompassed therein.

The compositions and methods of the presently disclosed subject matter are particularly useful for warm-blooded vertebrates. Thus, in some embodiments the presently disclosed subject matter concerns mammals and birds. More particularly provided are compositions and methods derived from and/or for use in mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also provided is the use of the disclosed methods and compositions on livestock, including but not limited to domesticated swine (pigs and hogs), ruminants, horses, poultry, and the like.

Similarly, all genes, gene names, and gene products disclosed herein are intended to correspond to homologs and/or orthologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes presented in GENBANK® Accession Nos: AAA60019 and NP_004976, the human amino acid sequences disclosed are intended to encompass homologous genes and gene products from other animals including, but not limited to other mammals, fish, amphibians, reptiles, and birds. Also encompassed are any and all nucleotide sequences that encode the disclosed amino acid sequences, including but not limited to those disclosed in the corresponding GENBANK® entries (i.e., J05582.1 and NM_004985, respectively).

The terms "cancer" and "tumor" are used interchangeably herein and can refer to both primary and metastasized solid tumors and carcinomas of any tissue in a subject, including but not limited to breast; colon; rectum; lung; oropharynx; hypopharynx; esophagus; stomach; pancreas; liver; gallbladder; bile ducts; small intestine; urinary tract including kidney, bladder, and urothelium; female genital tract including cervix, uterus, ovaries (e.g., choriocarcinoma and gestational trophoblastic disease); male genital tract including prostate, seminal vesicles, testes and germ cell tumors; endocrine glands including thyroid, adrenal, and pituitary; skin (e.g., hemangiomas and melanomas), bone or soft tissues; blood vessels (e.g., Kaposi's sarcoma); brain, nerves, eyes, and meninges (e.g., astrocytomas, gliomas, glioblastomas, retinoblastomas, neuromas, neuroblastomas, Schwannomas and meningiomas). As used herein, the terms "cancer and "tumor" are also intended to refer to multicellular tumors as well as individual neoplastic or preneoplastic cells. In some embodiments, a cancer or a tumor comprises a cancer or tumor of an epithelial tissue such as, but not limited to a carcinoma. In some embodiments, a tumor is an adenocarcinoma, which in some embodiments is an adenocarcinoma of the pancreas, breast, ovary, colon, or rectum, and/or a metastatic cell derived therefrom.

As used herein in the context of molecules, the term "effector" refers to any molecule or combination of molecules whose activity it is desired to deliver/into and/or localize at a cell. Effectors include, but are not limited to labels, cytotoxins, enzymes, growth factors, transcription factors, drugs, etc.

As used herein in the context of cells of the immune system, the term "effector" refers to an immune system cell that can be induced to perform a specific function associated with an immune response to a stimulus. Exemplary effector cells include, but are not limited to natural killer (NK) cells and cytotoxic T cells (Tc cells).

As used herein, the term "expression vector" refers to a DNA sequence capable of directing expression of a particular nucleotide sequence in an appropriate host cell, comprising a promoter operatively linked to the nucleotide sequence of interest which is operatively linked to termination signals. It also typically comprises sequences required for proper translation of the nucleotide sequence. The construct comprising the nucleotide sequence of interest can be chimeric. The construct can also be one that is naturally occurring but has been obtained in a recombinant form useful for heterologous expression.

As used herein, the term "hybridoma" refers to a cell or cell line that is produced in the laboratory from the fusion of an antibody-producing lymphocyte and a non-antibody-producing cancer cell, usually a myeloma or lymphoma cell. As would be known to those of one of ordinary skill in the art, a hybridoma can proliferate and produce a continuous supply of a specific monoclonal antibody. Methods for generating hybridomas are known in the art (see e.g., Harlow & Lane, 1988).

As used herein, the terms "operatively linked" and "operably linked" refer to transcriptional regulatory elements (such as, but not limited to promoter sequences, transcription terminator sequences, etc.) that are connected to a nucleotide sequence (for example, a coding sequence or open reading frame) in such a way that the transcription of the nucleotide sequence is controlled and regulated by that transcriptional regulatory element. Similarly, a nucleotide sequence is said to be under the "transcriptional control" of a promoter to which it is operably linked. Techniques for operatively linking a promoter region to a nucleotide sequence are known in the art.

As used herein, the term "prodrug" refers to an analog and/or a precursor of a drug (e.g., a cytotoxic agent) that substantially lacks the biological activity of the drug (e.g., a cytotoxic activity) until subjected to an activation step. Activation steps can include enzymatic cleavage, chemical activation steps such as exposure to a reductant, and/or physical activation steps such as photolysis. In some embodiments, activation occurs in vivo within the body of a subject, As used herein, the terms "antibody" and "antibodies" refer to proteins comprising one or more polypeptides substantially encoded by immunoglobulin genes or fragments of immunoglobulin genes. Immunoglobulin genes typically include the kappa (κ), lambda (λ), alpha (a), gamma (γ), delta (δ), epsilon (ϵ), and mu (μ) constant region genes, as well as myriad immunoglobulin variable region genes. Light chains are classified as either κ or λ. In mammals, heavy chains are classified as γ, μ, α, δ, or ϵ, which in turn define the immunoglobulin classes, IgG, IgM, IgA, IgD, and IgE, respectively. Other species have other light and heavy chain genes (e.g., certain avians produced what is referred to as IgY, which is an immunoglobulin type that hens deposit in the yolks of their eggs), which are similarly encompassed by the presently disclosed subject matter. In some embodiments, the term "antibody" refers to an antibody that binds specifically to an epitope that is present on a tumor antigen.

A typical immunoglobulin (antibody) structural unit is known to comprise a tetramer. Each tetramer is composed of two identical pairs of polypeptide chains, each pair having one "light" chain (average molecular weight of about 25 kiloDalton (kDa)) and one "heavy" chain (average molecular weight of about 50-70 kDa). The two identical pairs of polypeptide chains are held together in dimeric form by disulfide bonds that are present within the heavy chain region. The N-terminus of each chain defines a variable region of about 100 to 110 or more amino acids primarily responsible for antigen recognition (sometimes referred to as the "paratope"). The terms variable light chain (VL) and variable heavy chain (VH) refer to these light and heavy chains, respectively.

Antibodies typically exist as intact immunoglobulins or as a number of well-characterized fragments that can be produced by digestion with various peptidases. For example, digestion of an antibody molecule with papain cleaves the antibody at a position N-terminal to the disulfide bonds. This produces three fragments: two identical "Fab" fragments, which have a light chain and the N-terminus of the heavy chain, and an "Fc" fragment that includes the C-terminus of the heavy chains held together by the disulfide bonds. Pepsin, on the other hand, digests an antibody C-terminal to the disulfide bond in the hinge region to produce a fragment known as the "F(ab)'2" fragment, which is a dimer of the Fab fragments joined by the disulfide bond. The F(ab)'2 fragment can be reduced under mild conditions to break the disulfide linkage in the hinge region, thereby converting the F(ab')2 dimer into two "Fab" monomers. The Fab' monomer is essentially an Fab fragment with part of the hinge region (see e.g., Paul, 1993, for a more detailed description of other antibody fragments). With respect to these various fragments, Fab, F(ab')2, and Fab' fragments include at least one intact antigen binding domain (paratope), and thus are capable of binding to antigens.

While various antibody fragments are defined in terms of the digestion of an intact antibody, one of skill will appreciate that various of these fragments (including, but not limited to Fab' fragments) can be synthesized de novo either chemically or by utilizing recombinant DNA methodology. Thus, the term "antibody" as used herein also includes antibody fragments produced by the modification of whole antibodies and/or synthesized de novo using recombinant DNA methodologies. In some embodiments, the term "antibody" comprises a fragment that has at least one antigen binding domain (paratope).

Antibodies can be polyclonal or monoclonal. As used herein, the term "polyclonal" refers to antibodies that are present together in a given collection of antibodies and that are derived from different antibody-producing cells (e.g., B cells). Exemplary polyclonal antibodies include, but are not limited to those antibodies that bind to a particular antigen and that are found in the blood of an animal after that animal has produced an immune response against the antigen. However, it is understood that a polyclonal preparation of antibodies can also be prepared artificially by mixing at least non-identical two antibodies. Thus, polyclonal antibodies typically include different antibodies that are directed against (i.e., bind to) the same and/or different epitopes (sometimes referred to as an "antigenic determinant" or just "determinant") of any given antigen.

As used herein, the term "monoclonal" refers to a single antibody species and/or a substantially homogeneous population of a single antibody species. Stated another way, "monoclonal" refers to individual antibodies or populations of individual antibodies in which the antibodies are identical in specificity and affinity except for possible naturally occurring mutations that can be present in minor amounts. Typically, a monoclonal antibody (mAb or moAb) is generated by a single B cell or a progeny cell thereof (although the presently disclosed subject matter also encompasses "monoclonal" antibodies that are produced by molecular biological techniques as described herein). Monoclonal antibodies (mAbs or moAbs) are highly specific, typically being directed against a single antigenic site. Furthermore, in contrast to polyclonal antibody preparations, a given mAb is typically directed against a single epitope on the antigen.

In addition to their specificity, mAbs can be advantageous for some purposes in that they can be synthesized uncontaminated by other antibodies. The modifier "monoclonal" is not to be construed as requiring production of the antibody by any particular method, however. For example, in some embodiments, the mAbs of the presently disclosed subject matter are prepared using the hybridoma methodology first described by Kohler et al., 1975, and in some embodiments are made using recombinant DNA methods in prokaryotic or eukaryotic cells (see e.g., U.S. Pat. No. 4,816,567, the entire contents of which are incorporated herein by reference). mAbs can also be isolated from phage antibody libraries.

The antibodies, fragments, and derivatives of the presently disclosed subject matter can also include chimeric antibodies. As used herein in the context of antibodies, the term "chimeric", and grammatical variants thereof, refers to antibody derivatives that have constant regions derived substantially or exclusively from antibody constant regions from one species and variable regions derived substantially or exclusively from the sequence of the variable region from another species.

The variable region allows an antibody to selectively recognize and specifically bind epitopes on antigens. That is, the VL domain and VH domain, or subsets of the complementarity determining regions (CDRs) within these variable domains, of an antibody combine to form the variable region that defines a three dimensional antigen binding site. This quaternary antibody structure forms the antigen binding site present at the end of each arm of the antibody. More specifically, the antigen binding site is defined by three CDRs on each of the VH and VL chains. In some instances (e.g., certain immunoglobulin molecules derived from camelid species or engineered based on camelid immunoglobulins), a complete immunoglobulin molecule can consist of heavy chains only with no light chains.

In naturally occurring antibodies, there are six CDRs present in each antigen binding domain that are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable domain by one of ordinary skill in the art, since they have been precisely defined (see e.g., Chothia & Lesk, 1987; Kabat et al., 1991; Martin, 1996; Johnson & Wu, 2000).

A particular kind of chimeric antibody is a "humanized" antibody, in which the antibodies are produced by substituting the CDRs of, for example, a mouse antibody, for the CDRs of a human antibody (see e.g., PCT International Patent Application Publication No. WO 1992/22653). Thus, in some embodiments, a humanized antibody has constant regions and variable regions other than the CDRs that are derived substantially or exclusively from the corresponding regions of a human antibody, and CDRs that are derived substantially or exclusively from a mammal other than a human.

The antibodies the presently disclosed subject matter can be single chain antibodies and single chain antibody fragments, such as single chain variable fragments. Single-chain antibody fragments contain amino acid sequences having at least one of the variable regions and/or CDRs of the whole antibodies described herein, but are lacking some or all of the constant domains of those antibodies. These constant domains are not necessary for antigen binding, but constitute a major portion of the structure of whole antibodies. In the present invention, SEQ ID NOS 10 and 11 constitute the light chain and heavy chain fragments.

Single-chain antibody fragments can overcome some of the problems associated with the use of antibodies containing a part or all of a constant domain. For example, single-chain antibody fragments tend to be free of undesired interactions between biological molecules and the heavy-chain constant region, and/or other unwanted biological activities. Additionally, single-chain antibody fragments are considerably smaller than whole antibodies and can therefore be characterized by greater capillary permeability than whole antibodies, allowing single-chain antibody fragments to localize and bind to target antigen-binding sites more efficiently. Also, antibody fragments can be produced on a relatively large scale in prokaryotic cells, thus facilitating their production. Furthermore, the relatively small size of single-chain antibody fragments makes them less likely than whole antibodies to provoke an immune response in a recipient. The single-chain antibody fragments of the presently disclosed subject matter include, but are not limited to single chain fragment variable (scFv) antibodies and derivatives thereof such as, but not limited to tandem di-scFv, tandem tri-scFv, miniantibodies, and minibodies.

Fv fragments correspond to the variable fragments at the N-termini of immunoglobulin heavy and light chains. Fv fragments appear to have lower interaction energy of their two chains than Fab fragments. To stabilize the association of the VH and VL domains, they can be linked with peptides (see e.g., Bird et al., 1988; Huston et al., 1988), disulfide bridges (see e.g., Glockshuber et al., 1990), and/or "knob in hole" mutations (see e.g., Zhu et al., 1997). ScFv fragments can be produced by methods well known to those skilled in the art (see e.g., Whitlow et al., 1991; Huston et al., 1993).

A "single-chain variable fragment" (scFv) is a fusion protein of the variable regions of the heavy (VH) and light chains (VL) of immunoglobulins, connected with a short linker peptide. The linker can be rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and the introduction of the linker. scFv can be produced in bacterial cells such as *E. coli* or in eukaryotic cells.

Methods and Compositions scFvs and Nucleic Acids Thereof

Disclosed herein are scFvs which specifically bind tumor-associated glycoprotein 72 (TAG-72). Even more specifically, they can bind the sialyl-Tn epitope of TAG-72. These highly stable, high-affinity, bacterially-expressible scFvs are capable of specifically binding to a sialyl-Tn glycoform epitope found in TAG-72, a mucin-like glycoprotein found in human adenocarcinomas. This epitope is rarely expressed in the microenvironment of healthy tissue and thus provides a specific target for imaging and detection. Radiolabeled antibodies that specifically bind Sialyl-Tn allow one to image at the molecular level and provide the ability to improve patient care. Various molecules—B72.3, CC49, huCC49, 3E8—demonstrate the utility of anti-TAG-72 antibodies in cancer diagnosis and imaging.

3E8.scFv, a scFv that incorporates structural and binding site components from a CC49 scFv and the 3E8 antibody, as well as other sequence features for bacterial expression and purification, are described herein. Also described herein is the DNA sequence, protein sequence, and method of expression in and purification from *Escherichia coli.*

The stability of the scFv and its binding to TAG-72 in mucin is demonstrated herein. Also demonstrated is the use of biotinylated 3E8.scFv in immunohistochemistry against a human colon cancer specimen. Finally, described herein is the construction of a C-terminal Cys mutant, 3E8.scFv.Cys, and it is demonstrated that it can be specifically conjugated to a maleimide PEG. Since 3E8.scFv is derived from a humanized antibody, it is not likely to elicit a human immune response.

The scFvs disclosed herein have the following properties: tight and specific binding to the cancer epitope, sialyl-Tn (Thor 1986; Thor 1987), enhanced stability for longer shelf life, performance during application, resistance to serum proteases; improved expression and purification from bacteria; amenability to further engineering; reduced immunogenicity; and increased tissue penetrance over full-length antibodies (IgG) and fragment antigen binding (Fab) domains (Yokota 1992) Several of these properties exist in one or more sialyl-Tn binding proteins, but to date, no single molecule combines all desired features (Colcher 1999; Yoon 2006).

Specifically, the scFvs disclosed herein can have a shelf life of 1, 2, 3, 4, 5, 6, 7, 8, 9, 10, 11, or 12 weeks, or 3, 4, 5, 6, 7, 8, 9, 10, 11, or 12 months, or 1 2, 3, 4, 5, 6, 7, 8, 9, or 10 years more than a full-length antibody (IgG) or Fab domain. The scFvs disclosed herein can be 2, 3, 4, 5, 6, 7, 8, 9, or 10 times, or any amount smaller, larger or in between, more resistance to serum proteases. They can have 2, 3, 4, 5, 6, 7, 8, 9, or 10 times, or any amount smaller, larger or in between, reduced immunogenicity when compared with a full length IgG or Fab domain. They can have 2, 3, 4, 5, 6, 7, 8, 9, or 10 times, or any amount smaller, larger or in between, increased tissue penetrance compared with a full length IgG or Fab domain. They can have 1, 2, or 3 or more of these characteristics.

To generate a cancer detection and imaging agent with the above features, a single chain variable fragment (scFv) has been engineered (SEQ ID NOS 1 and 2 are examples). Full-length antibodies are large (~160 kDa) and possess innate effector functions that are not necessary, nor desirable for imaging and detection (FcRn recycling and cellular internalization, cytoxicity, etc.). Single chain variable fragments lack the constant domains responsible for effector functions, but maintain the full antigen binding domains (Bird 1988). Their small size (~25 kDa) and lack of complexity is more amenable to bacterial production, and high-throughput engineering and screening (Sandhu 1992; Pini 2000). Additionally, the compactness of scFvs and lack of cellular uptake improve tissue penetrance and provide more flexible serum half-lives. The clearance rates are faster than IgGs which is desired when using harmful radionuclides, but can be extended by PEGylation to complement a wider pairing of isotopes (Yang 2003). The 3E8-inspired scFvs disclosed herein are humanized for reduced immunogenicity, expresses well in bacteria, are 1, 2, 3, 4, 5, 6, 7, 8, 9, 10, 11, 12, 13, 14, 15, 16, 17, 18, 19, or 20° C. more stable than the clinically tested CC49.scFv, and bind the sialyl-Tn antigen with low nanomolar affinity.

The scFvs disclosed herein can be made in a variety of ways, as one of skill in the art will appreciate. In its most essential form, the antibody fragment can comprise a heavy chain variable region comprising SEQ ID NO: 10, and a light chain variable region comprising SEQ ID NO: 11, or a fragment of SEQ ID NO: 10 and 11. For example, an scFv can be produced which has 60, 70, 80, 90, 91, 92, 93, 94, 95, 96, 97, 98, or 99% identity to SEQ ID NO: 10, and 60, 70, 80, 90, 91, 92, 93, 94, 95, 96, 97, 98, or 99% identity to SEQ ID NO: 11. The scFv can be functionally equivalent to those found in SEQ ID NOS 10 and 11.

The scFvs can have an antigen binding affinity for sialyl-Tn which is at least 25% that of 3E8. 3E8 has shown an anti-tumor therapeutic effect in athymic mice bearing human colon adenocarcinoma xenografts (Yoon 2006).

The presently disclosed subject matter includes functional equivalents of the antibodies of the presently disclosed subject matter. As used herein, the phrase "functional equivalent" as it refers to an antibody refers to a molecule that has binding characteristics that are comparable to those of a given antibody. In some embodiments, chimerized, humanized, and single chain antibodies, as well as fragments thereof, are considered functional equivalents of the corresponding antibodies upon which they are based.

Functional equivalents also include polypeptides with amino acid sequences substantially the same as the amino acid sequence of the variable or hypervariable regions of the antibodies of the presently disclosed subject matter. As used herein with respect to nucleic acid and/or amino acid sequences, the phrase "substantially the same" refers to a biosequence with in some embodiments at least 80%, in some embodiments at least 85%, in some embodiments at least about 90%, in some embodiments at least 91%, in some embodiments at least 92%, in some embodiments at least 93%, in some embodiments at least 94%, in some embodiments at least 95%, in some embodiments at least 96%, in some embodiments at least 97%, in some embodiments at least 98%, and in some embodiments at least about 99% sequence identity to another nucleic acid and/or amino acid sequence, as determined by the FASTA search method in accordance with Pearson & Lipman, 1988. In some embodiments, the percent identity calculation is performed over the full length of the nucleic acid and/or amino acid sequence of an antibody of the presently disclosed subject matter.

Specifically disclosed herein is an amino acid sequence comprising 90% identity to SEQ ID NO: 1. Also disclosed is an isolated amino acid sequence comprising 90% identity to SEQ ID NO: 2. Further disclosed is a nucleic acid sequence from which may be expressed an antibody fragment, such as the scFv antibodies disclosed herein. Also disclosed is nucleic acid sequence from which may be expressed the antibody fragments of the present invention. Disclosed herein is a nucleic acid sequence comprising 90% identity to SEQ ID NO: 7. Also disclosed is a nucleic acid sequence comprising 90% identity to SEQ ID NO: 8. Also disclosed is a vector comprising the nucleic acids disclosed herein. Vectors include, but are not limited to, a bare nucleic acid segment, a carrier-associated nucleic acid segment, a nucleoprotein, a plasmid, a virus, a viroid, or a transposable element. Also disclosed is a cell that produces the antibody fragment of the present invention.

Treatment Methods

Disclosed herein are compositions comprising an scFv and a pharmaceutically acceptable carrier. For example, disclosed are compositions useful for the treatment of cancer comprising a therapeutically effective amount of an scFv. For instance, the antibody fragment can be, directly or indirectly, associated with or linked to an effector moiety having therapeutic activity, and the composition is suitable for the treatment of cancer. The effector moiety can be a radionuclide, therapeutic enzyme, anti-cancer drug, cytokine, cytotoxin, or anti-proliferative agent.

Disclosed herein is a method for in vivo treatment of a mammal having a TAG-72-expressing cancer comprising a step of administering to the mammal a therapeutically effective amount of a composition comprising an scFv.

Also disclosed is a method for suppressing tumor growth in a subject, the method comprising administering to a subject bearing a tumor an effective amount of an scFv composition, wherein the scFv is coupled to an anti-tumor composition. By "suppressing tumor growth" is meant that a tumor grows less than one which is not treated (a control). For example, suppressed tumor growth can mean that the tumor being treated grows 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 50, 60, 70, 80, 90, or 100% less than the measured growth of a control over the same period of time.

Administration

The scFvs of the invention may be administered to a mammal in accordance with the aforementioned methods of treatment in an amount sufficient to produce such effect to a therapeutic, prophylactic, or diagnostic effect. Such antibodies of the invention can be administered to such mammal in a conventional dosage form prepared by combining the antibody of the invention with a conventional pharmaceutically acceptable carrier or vehicle, diluent, and/or excipient according to known techniques to form a suspension, injectable solution, or other formulation. It will be recognized by one of skill in the art that the form and character of the pharmaceutically acceptable carrier or diluent is dictated by the amount of active ingredient with which it is to be combined, the route of administration and other well-known variables.

Pharmaceutically acceptable formulations may include, e.g., a suitable solvent, preservatives such as benzyl alcohol if desired, and a buffer. Useful solvent may include, e.g., water, aqueous alcohols, glycols, and phosphate and carbonate esters. Such aqueous solutions contain no more than 50% by volume of organic solvent. Suspension-type formulations may include a liquid suspending medium as a carrier, e.g., aqueous polyvinylpyrrolidone, inert oils such as vegetable oils or highly refined mineral oils, or aqueous cellulose ethers such as aqueous carboxymethylcellulose. A thickener such as gelatin or an alginate may also be present, one or more natural or synthetic surfactants or antifoam agents may be used, and one or more suspending agents such as sorbitol or another sugar may be employed therein. Such formations may contain one or more adjuvants.

The route of administration of the scFv of the invention may be oral, parenteral, by inhalation or topical. The term parenteral as used herein includes intravenous, intramuscular, subcutaneous, rectal, vaginal or intraperitoneal administration. The subcutaneous, intravenous and intramuscular forms of parenteral administration are generally preferred. The daily parenteral and oral dosage regimens for employing humanized antibodies of the invention prophylactically or therapeutically will generally be in the range of about 0.005 to 100, but preferably about 0.5 to 10, milligrams per kilogram body weight per day.

The scFv of the invention may also be administered by inhalation. By "inhalation" is meant intranasal and oral inhalation administration. Appropriate dosage forms for such administration, such as an aerosol formulation or a metered dose inhaler, may be prepared by conventional techniques. The preferred dosage amount of a compound of the invention to be employed is generally within the range of about 0.1 to 1000 milligrams, preferably about 10 to 100 milligrams/kilogram body weight.

The scFv of the invention may also be administered topically. By topical administration is meant non-systemic administration. This includes the administration of a humanized antibody (or humanized antibody fragment) formulation of the invention externally to the epidermis or to the buccal cavity, and instillation of such an antibody into the ear, eye, or nose, and wherever it does not significantly enter the bloodstream. By systemic administration is meant oral, intravenous, intraperitoneal, subcutaneous, and intramuscular administration. The amount of an antibody required for therapeutic, prophylactic, or diagnostic effect will, of course, vary with the antibody chosen, the nature and severity of the condition being treated and the animal undergoing treatment, and is ultimately at the discretion of the physician. A suitable topical dose of an antibody of the invention will generally be within the range of about 1 to 100 milligrams per kilogram body weight daily.

Formulations

While it is possible for an antibody fragment to be administered alone, it is preferable to present it as a pharmaceutical formulation. The active ingredient may comprise, for topical administration, from 0.001% to 10% w/w, e.g., from 1% to 2% by weight of the formulation, although it may comprise as much as 10% w/w but preferably not in excess of 5% w/w and more preferably from 0.1% to 1% w/w of the formulation. The topical formulations of the present invention, comprise an active ingredient together with one or more acceptable carrier(s) therefor and optionally any other therapeutic ingredients(s). The carrier(s) must be "acceptable" in the sense of being compatible with the other ingredients of the formulation and not deleterious to the recipient thereof.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

Kits according to the present invention include scFvs as disclosed herein, and instructions for their use. Frozen or lyophilized humanized antibody fragments to be reconstituted, respectively, by thawing (optionally followed by further dilution) or by suspension in a (preferably buffered) liquid vehicle can also be used in these kits. The kits may also include buffer and/or excipient solutions (in liquid or frozen form)—or buffer and/or excipient powder preparations to be reconstituted with water—for the purpose of mixing with the humanized antibodies or humanized antibody fragments to produce a formulation suitable for administration. Thus, preferably the kits containing the humanized antibodies or humanized antibody fragments are frozen, lyophilized, pre-diluted, or pre-mixed at such a concentration that the addition of a predetermined amount of heat, of water, or of a solution provided in the kit will result in a formulation of sufficient concentration and pH as to be effective for in vivo or in vitro use in the treatment or diagnosis of cancer. Preferably, such a kit will also comprise instructions for reconstituting and using the humanized antibody or humanized antibody fragment composition to treat or detect cancer. The kit may also comprise two or more component parts for the reconstituted active composition. For example, a second component part—in addition to the humanized antibodies or humanized antibody fragments—may be bifunctional chelant, bifunctional chelate, or a therapeutic agent such as a radionuclide, which when mixed with the humanized antibodies or humanized antibody fragments forms a conjugated system therewith. The above-noted buffers, excipients, and other component parts can be sold separately or together with the kit.

It will be recognized by one of skill in the art that the optimal quantity and spacing of individual dosages of a humanized antibody or humanized antibody fragment of the invention will be determined by the nature and extent of the condition being treated, the form, route and site of administration, and the particular animal being treated, and that such optima can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Active Agents

The compositions of the presently disclosed subject matter can comprise an active agent, wherein the active agent comprises a therapeutic moiety, a diagnostic moiety, and/or a biologically active moiety. As used herein, the phrase "active agent" thus refers to a component of the presently disclosed compositions that provides a therapeutic benefit to a subject, permits visualization of cells or tissues in which the compositions of the presently disclosed subject matter accumulate, detection of epitopes to which the presently disclosed scFvs bind, and/or enhances any of these activities. In some embodiments, an active agent of the presently disclosed subject matter is selected from the group consisting of a radioactive molecule (including, but not limited to radionuclides and radioisotopes), a sensitizer molecule, an imaging agent or other detectable agent, a toxin, a cytotoxin, an anti-angiogenic agent, an anti-tumor agent, a chemotherapeutic agent, an immunomodulator, a cytokine, a reporter group, and combinations thereof. It is understood that these categories are not intended to be mutually exclusive, as some radioactive molecules, for example, are also chemotherapeutic agents, some immunomodulators are cytokines, etc.

In some embodiments, an active agent comprises a chemotherapeutic. Various chemotherapeutics are known to one of ordinary skill in the art, and include, but are not limited to alkylating agents such as nitrogen mustards (e.g., Chlorambucil, Cyclophosphamide, Isofamide, Mechlorethamine, Melphalan, Uracil mustard), aziridines (e.g., Thiotepa), methanesulfonate esters (e.g., Busulfan), nitroso ureas (e.g., Carmustine, Lomustine, Streptozocin), platinum complexes (e.g., Cisplatin, Carboplatin), and bioreductive alkylators (e.g., Mitomycin C, Procarbazine); DNA strand breaking agents (e.g., Bleomycin); DNA topoisomerase I inhibitors (e.g., camptothecin and derivatives thereof including, but not limited to 10-hydroxycamptothecin), DNA topoisomerase II inhibitors (e.g., Amsacrine, Dactinomycin, Daunorubicin, Doxorubicin, Idarubicin, Mitoxantrone, Etoposide, Teniposide, Podophyllotoxin); DNA minor groove binders (e.g., Plicamycin); anti-metabolites such as folate antagonists (e.g., Methotrexate and trimetrexate), pyrimidine antagonists (e.g., Fluorouracil, Fluorodeoxyuridine, CB3717, Azacytidine, Cytarabine, Floxuridine), purine antagonists (e.g., Mercaptopurine, 6-Thioguanine, Fludarabine, Pentostatin), sugar modified analogs (e.g., Cyctrabine, Fludarabine), and ribonucleotide reductase inhibitors (e.g., Hydroxyurea); tubulin interactive agents (e.g., Vincristine, Vinblastine, Paclitaxel); adrenal corticosteroids (e.g., Prednisone, Dexamethasone, Methylprednisolone, Prednisolone); hormonal blocking agents such as estrogens and related compounds (e.g., Ethinyl Estradiol, Diethylstilbesterol, Chlorotrianisene, Idenestrol), progestins (e.g., Hydroxyprogesterone caproate, Medroxyprogesterone, Megestrol), androgens (e.g., Testosterone, Testosterone propionate; Fluoxymesterone, Methyltestosterone), leutinizing hormone releasing hormone agents and/or gonadotropin-releasing hormone antagonists (e.g., Leuprolide acetate; Goserelin acetate), anti-estrogenic agents (e.g., Tamoxifen), anti-androgen agents (e.g., Flutamide), and anti-adrenal agents (e.g., Mitotane, Aminoglutethimide). Other chemotherapeutics include, but are not limited to Taxol, retinoic acid and derivatives thereof (e.g., 13-cis-retinoic acid, all-trans-retinoic acid, and 9-cis-retinoic acid), sulfathiazole, mitomycin C, mycophenolic acid, sulfadiethoxane, and gemcitabine (4-amino-1-(2-deoxy-2,2-difluoro- -D-eryi/7ro-pentofuranosyl)pyhmidin-2(1H)-on-2',2'-difluoro-2'-deoxycytidine).

The subject scFvs may also be administered in combination with other anti-cancer agents, e.g., other antibodies or drugs. Also, the subject humanized scFvs may be directly or indirectly attached to effector having therapeutic activity. Suitable effector moieties include by way of example cytokines (IL-2, TNF, interferons, colony stimulating factors, IL-1, etc.), cytotoxins (*Pseudomonas* exotoxin, ricin, abrin, etc.), radionuclides, such as $^{90}$Y, $^{131}$I, $^{99m}$Tc, $^{111}$In, $^{125}$I, among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

The compositions of the presently disclosed subject matter can further comprise a drug carrier to facilitate drug preparation and administration. Any suitable drug delivery vehicle or carrier can be used, including but not limited to a gene therapy vector (e.g., a viral vector or a plasmid), a microcapsule, for example a microsphere or a nanosphere (Manome et al., 1994; Hallahan et al., 2001 b; Saltzman & Fung, 1997), a peptide (U.S. Pat. Nos. 6,127,339 and 5,574,172), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al., 1997; U.S. Pat. Nos. 4,551,482; 5,714,166; 5,510,103; 5,490,840; and 5,855,900), and a polysome (U.S. Pat. No. 5,922,545).

The disclosed scFvs can also be coupled to drugs or drug carriers using methods known in the art, including but not limited to carbodiimide conjugation, esterification, sodium periodate oxidation followed by reductive alkylation, and glutaraldehyde crosslinking (see e.g., U.S. Pat. No. 6,071,890; and European Patent No. 0 439 095).

Detection Methods

Disclosed are compositions suitable for the in vivo or in vitro detection of cancer comprising a diagnostically effective amount of an scFv disclosed herein. The scFv can be, directly or indirectly, associated with or linked to a detectable label, and the composition can be suitable for detection of cancer. Also disclosed is a method for in vitro immunodetection of TAG-72-expressing cancer cells comprising a step of contacting the cancer cells with a composition comprising an scFv of the present invention. The scFv can be bound to a solid support, for example.

Also disclosed is a method of in vivo immunodetection of TAG-72-expressing cancer cells in a mammal comprising a step of administering to the mammal a diagnostically effective amount of a composition comprising the scFv of the present invention.

For diagnostic applications, a detectable amount of a composition of the presently disclosed subject matter is administered to a subject. A "detectable amount", as used herein to refer to a composition, refers to a dose of such a composition that the presence of the composition can be determined in vivo or in vitro. A detectable amount will vary according to a variety of factors, including but not limited to chemical features of the composition being labeled, the detectable label, the labeling methods, the method of imaging and parameters related thereto, metabolism of the labeled drug in the subject, the stability of the label (including, but not limited to the half-life of a radionuclide label), the time elapsed following administration of the composition prior to imaging, the route of administration, the physical condition and prior medical history of the subject, and the size and longevity of the tumor or suspected tumor. Thus, a detectable amount can vary and can be tailored to a particular application. After study of the present disclosure, it is within the skill of one in the art to determine such a detectable amount.

As used herein, the terms "detectable moiety", "detectable label", and "detectable agent" refer to any molecule that can be detected by any moiety that can be added to an antibody fragment that allows for the detection of the antibody fragment in vitro and/or in vivo. Representative detectable moieties include, but are not limited to, chromophores, fluorescent moieties, enzymes, antigens, groups with specific reactivity, chemiluminescent moieties, and electrochemically detectable moieties, etc. In some embodiments, the antibodies are biotinylated.

Detection and imaging of the antibody fragment is tunable, such that imaging can be performed in under 1, 2, 4, 6, 12, or 18, 24, 36, or 48 hours, or any amount below, above, or between this amount. It has been demonstrated that PEGs/larger fragments increase serum half-life by 2, 3, 4, 5, 6, 7, 8, 9, 10, 15, 20, 25, 30, 35, 40, 45, 50, 55, 60, 65, 70, 75, 80, 85, 90, 95, or 100%, or 2, 3, 4, 5, 6, 7, 8, 9, or 10 or more times compared to a smaller fragment. This allows for imaging at different time points. For therapeutic purposes, it allows for an increase in the therapeutic window.

Detectable Moieties

In some embodiments, a detectable moiety comprises a fluorophore. Any fluorophore can be employed with the compositions of the presently disclosed subject matter, provided that the conjugation of fluorophore results in a composition that is detectable either in vivo (e.g., after administration to a subject) and/or in vitro, and further does not negatively impact the ability of the antibody fragment to bind to its epitope. Representative fluorophores include, but are not limited to 7-dimethylaminocoumarin-3-carboxylic acid, dansyl chloride, nitrobenzodiazolamine (NBD), dabsyl chloride, cinnamic acid, fluorescein carboxylic acid, Nile Blue, tetramethylcarboxyrhodamine, tetraethylsulfohodamine, 5-carboxy-X-rhodamine (5-ROX), and 6-carboxy-X-rhodamine (6-ROX). It is understood that these representative fluorophores are exemplary only, and additional fluorophores can also be employed. For example, there the ALEXA FLUOR® dye series includes at least 19 different dyes that are characterized by different emission spectra. These dyes include ALEXA FLUOR® 350, 405, 430, 488, 500, 514, 532, 546, 555, 568, 594, 610, 633, 635, 647, 660, 680, 700, and 750 (available from Invitrogen Corp., Carlsbad, Calif., United States of America), and the choice of which dye to employ can be made by the skilled artisan after consideration of the instant specification based on criteria including, but not limited to the chemical compositions of the specific ALEXA FLUOR®, whether multiple detectable moieties are to be employed and the emission spectra of each, the detection technique to be employed, etc.

In some embodiments, a detectable moiety comprises a cyanine dye. Non-limiting examples of cyanine dyes that can be conjugated to the antibody fragments of the presently disclosed subject matter include the succinimide esters Cy5, Cy5.5, and Cy7, supplied by Amersham Biosciences (Piscataway, N.J., United States of America).

In some embodiments, a detectable moiety comprises a near infrared (NIR) dye. Non-limiting examples of near infrared dyes that can be conjugated to the scFv of the presently disclosed subject matter include NIR641, NIR664, NIT7000, and NIT782.

In some embodiments, the biotinylated antibodies are detected using a secondary antibody that comprises an avidin or streptavidin group and is also conjugated to a fluorescent label including, but not limited to Cy3, Cy5, Cy7, and any of the ALEXA FLUOR®® series of fluorescent labels available from INVITROGEN™ (Carlsbad, Calif., United States of America). In some embodiments, the scFv is directly labeled with a fluorescent label and cells that bind to the antibody fragment are separated by fluorescence-activated cell sorting. Additional detection strategies are known to the skilled artisan.

For diagnostic applications (including but not limited to detection applications and imaging applications), the antibodies of the presently disclosed subject matter can be labeled with a detectable moiety. The detectable moiety can be any one that is capable of producing, either directly or indirectly, a detectable signal. For example, a detectable moiety can be a radioisotope, such as but not limited to 3H, 14C, 32P, 35S, 125l, or 3 1; a fluorescent or chemiluminescent compound such as but not limited to fluorescein isothiocyanate, rhodamine, or luciferin; or an enzyme, such as but not limited to alkaline phosphatase, β-galactosidase, or horseradish peroxidase.

The presently disclosed subject matter further provides methods for diagnosing a tumor, wherein a tumor sample or biopsy is evaluated in vitro. In some embodiments, a targeting ligand of the presently disclosed subject matter comprises a detectable label such as a fluorescent label, an epitope tag, or a radioactive label, each described briefly herein below.

Detection of an Epitope Tag

If an epitope label has been used, a protein or compound that binds the epitope can be used to detect the epitope. A representative epitope label is biotin, which can be detected by binding of an avidin-conjugated fluorophore, for example avidin-FITC. Alternatively, the label can be detected by binding of an avidin-horseradish peroxidase (HRP) streptavidin conjugate, followed by colorimetric detection of an HRP enzymatic product. The production of a colorimetric or luminescent product/conjugate is measurable using a spectrophotometer or luminometer, respectively.

Autoradiographic Detection

In the case of a radioactive label (e.g., $^{131}$1 or $^{99m}$Tc) detection can be accomplished by conventional autoradiography or by using a phosphorimager as is known to one of skill in the art. A preferred autoradiographic method employs photostimulable luminescence imaging plates (Fuji Medical Systems of Stamford, Conn., United States of America). Briefly, photostimulable luminescence is the quantity of light emitted from irradiated phosphorous plates following stimulation with a laser during scanning. The luminescent response of the plates is linearly proportional to the activity.

Any method known in the art for conjugating an antibody to a detectable moiety can be employed.

Immunohistochemistry

Disclosed herein are methods of using immunohistochemistry (IHC) utilizing the scFvs disclosed herein to detect cancer. IHC detects target molecules through antigen-antibody complexes in a pathological specimen using enzyme-linked antigens or antibodies. The presence of the target molecule can then detected via an enzyme immunoassay.

A multitude of benefits are realized with IHC versus traditional immunofluorescence. For example, unlike immunofluorescence, IHC can be used with commonly used formalin-fixed paraffin-embedded tissue specimens. Pathological specimens, including histological tissue sections and/or other biological preparations such as tissue culture cells and PAP smears, are commonly used in diagnostic pathology and can be easily screened via IHC. Further, IHC staining is permanent and preserves cell morphology. A comparison of the cell morphology and antigen proliferation on two different slides can be useful in monitoring the progression of a disease.

Once a labeled antibody has been attached, either directly or indirectly, to the specimen, a substrate, specific for the enzyme, is added to the specimen. When the substrate is added, the enzyme label converts the substrate causing a color change that can be seen with light microscopy. The presence of a color change indicates the presence of the target molecule and allows an observer to determine, assess, and diagnose the disease level and severity.

In Vivo Imaging

The scFvs of the presently disclosed subject matter also are useful for in vivo imaging, wherein an antibody labeled with a detectable moiety such as a radio-opaque agent and/or a radioisotope is administered to a subject, in some embodiments via intravenous administration, and the presence and location of the labeled antibody in the host is assayed. This imaging technique can be useful in the staging and treatment of malignancies.

Therefore, disclosed is a method of in vivo treatment of cancer comprising the steps of: (a) intravenously administering a radionuclide-labeled scFv; (b) thereafter detecting tumor cells using a radionuclide activity probe; and (c) thereafter removing the detected tumor cells by surgical excision.

Thus, in some embodiments, a composition of the presently disclosed subject matter comprises a label that can be detected in vivo. The term "in vivo" as used herein to describe imaging or detection methods, refers to generally non-invasive methods such as scintigraphic methods, magnetic resonance imaging, ultrasound, or fluorescence, each described briefly herein below. The term "non-invasive methods" does not exclude methods employing administration of a contrast agent to facilitate in vivo imaging.

In some embodiments, the detectable moiety can be conjugated or otherwise associated with the scFv of the presently disclosed subject matter, a therapeutic, a diagnostic agent, a drug carrier, or combinations thereof as set forth in more detail hereinabove. Following administration of the labeled composition to a subject, and after a time sufficient for binding, the biodistribution of the composition can be visualized. The term "time sufficient for binding" refers to a temporal duration that permits binding of the labeled agent to a radiation-induced target molecule.

Scintigraphic Imaging

Scintigraphic imaging methods include SPECT (Single Photon Emission Computed Tomography), PET (Positron Emission Tomography), gamma camera imaging, and rectilinear scanning. A gamma camera and a rectilinear scanner each represent instruments that detect radioactivity in a single plane. Most SPECT systems are based on the use of one or more gamma cameras that are rotated about the subject of analysis, and thus integrate radioactivity in more than one dimension. PET systems comprise an array of detectors in a ring that also detect radioactivity in multiple dimensions.

Imaging instruments suitable for practicing the detection and/or imaging methods of the presently disclosed subject matter, and instruction for using the same, are readily available from commercial sources. For example, a SPECT scanner can be used with a CT scanner, with coregistration of images. As in PET/CT, this allows location of tumors or tissues which may be seen on SPECT scintigraphy, but are difficult to precisely locate with regard to other anatomical structures. Both PET and SPECT systems are offered by ADAC of Milpitas, Calif., United States of America, and Siemens of Hoffman Estates, Ill., United States of America. Related devices for scintigraphic imaging can also be used, such as a radio-imaging device that includes a plurality of sensors with collimating structures having a common source focus.

When scintigraphic imaging is employed, the detectable label comprises in some embodiments a radionuclide label, in some embodiments a radionuclide label selected from the group consisting of $^{18}$F, $^{64}$Cu, $^{65}$Cu, $^{67}$Ga, $^{68}$Ga, $^{77}$Br, $^{80m}$Br, $^{95}$Ru, $^{97}$Ru, $^{103}$Ru, $^{105}$Ru, $^{99m}$Tc, $^{107}$Hg, $^{203}$Hg, $^{123}$I, $^{124}$I, $^{125}$I, $^{I}$ $^{131}$I, $^{133}$I, $^{111}$In, $^{113m}$In, $^{99m}$Re, $^{105}$Re, $^{101}$Re, $^{186}$Re, $^{188}$Re, $^{121m}$Te, $^{122m}$Te, $^{125m}$Te, $^{165}$Tm, $^{167}$Tm, $^{168}$Tm, and nitride or oxide forms derived there from. In some embodiments, the radionuclide label comprises $^{131}$I or $^{99m}$Tc.

Methods for radionuclide labeling of a molecule so as to be used in accordance with the disclosed methods are known in the art. For example, a targeting molecule can be derivatized so that a radioisotope can be bound directly to it. Alternatively, a linker can be added that to enable conjugation. Representative linkers include diethylenetriamine pentaacetate (DTPA)-isothiocyanate, succinimidyl 6-hydrazinium nicotinate hydrochloride (SHNH), and hexamethylpropylene amine oxime (U.S. Pat. No. 6,024,938). Additional methods can be found in U.S. Pat. No. 6,080,384.

When the labeling moiety is a radionuclide, stabilizers to prevent or minimize radiolytic damage, such as ascorbic acid, gentisic acid, or other appropriate antioxidants, can be added to the composition comprising the labeled targeting molecule.

Magnetic Resonance Imaging (MRI)

Magnetic resonance image-based techniques create images based on the relative relaxation rates of water protons in unique chemical environments. As used herein, the term "magnetic resonance imaging" refers to magnetic source techniques including convention magnetic resonance imaging, magnetization transfer imaging (MTI), proton magnetic resonance spectroscopy (MRS), diffusion-weighted imaging (DWI) and functional MR imaging.

Contrast agents for magnetic source imaging include but are not limited to paramagnetic or superparamagnetic ions, iron oxide particles, and water-soluble contrast agents. Paramagnetic and superparamagnetic ions can be selected from the group of metals including iron, copper, manganese, chromium, erbium, europium, dysprosium, holmium and gadolinium. Preferred metals are iron, manganese and gadolinium; most preferred is gadolinium.

Those skilled in the art of diagnostic labeling recognize that metal ions can be bound by chelating moieties, which in turn can be conjugated to a therapeutic agent in accordance with the methods of the presently disclosed subject matter. For example, gadolinium ions are chelated by diethylenetriaminepentaacetic acid (DTPA). Lanthanide ions are chelated by tetraazacyclododocane compounds. See U.S. Pat. Nos. 5,738,837 and 5,707,605. Alternatively, a contrast agent can be carried in a liposome.

Images derived used a magnetic source can be acquired using, for example, a superconducting quantum interference device magnetometer (SQUID, available with instruction from Quantum Design of San Diego, Calif., United States of America; see also U.S. Pat. No. 5,738,837).

Ultrasound

Ultrasound imaging can be used to obtain quantitative and structural information of a target tissue, including a tumor. Administration of a contrast agent, such as gas microbubbles, can enhance visualization of the target tissue during an ultrasound examination. In some embodiments, the contrast agent can be selectively targeted to the target tissue of interest, for example by using a peptide for guided drug delivery (e.g., radiation guided drug delivery) as disclosed herein. Representative agents for providing microbubbles in vivo include but are not limited to gas-filled lipophilic or lipid-based bubbles (e.g., U.S. Pat. Nos. 6,245,318; 6,231,834; 6,221,018; and 5,088,499). In addition, gas or liquid can be entrapped in porous inorganic particles that facilitate microbubble release upon delivery to a subject (U.S. Pat. Nos. 6,254,852 and 5,147,631).

Gases, liquids, and combinations thereof suitable for use with the presently disclosed subject matter include air; nitrogen; oxygen; is carbon dioxide; hydrogen; nitrous oxide; an inert gas such as helium, argon, xenon or krypton; a sulfur fluoride such as sulfur hexafluoride, disulfur decafluoride or trifluoromethylsulfur pentafluoride; selenium hexafluoride; an optionally halogenated silane such as tetramethylsilane; a low molecular weight hydrocarbon (e.g. containing up to 7 carbon atoms), for example an alkane such as methane, ethane, a propane, a butane or a pentane, a cycloalkane such as cyclobutane or cyclopentane, an alkene such as propene or a butene, or an alkyne such as acetylene; an ether; a ketone; an ester; a halogenated low molecular weight hydrocarbon (e.g. containing up to 7 carbon atoms); or a mixture of any of the foregoing. Halogenated hydrocarbon gases can show extended longevity, and thus are preferred for some applications. Representative gases of this group include decafluorobutane, octafluorocyclobutane, decafluoroisobutane, octafluoropropane, octafluorocyclopropane, dodecafluoropentane, decafluorocyclopentane, decafluoroisopentane, perfluoropexane, perfluorocyclohexane, perfluoroisohexane, sulfur hexafluoride, and perfluorooctaines, perfluorononanes; perfluorodecanes, optionally brominated.

Attachment of targeting ligands to lipophilic bubbles can be accomplished via chemical crosslinking agents in accordance with standard protein-polymer or protein-lipid attachment methods (e.g., via carbodiimide (EDC) or thiopropionate (SPDP)). To improve targeting efficiency, large gas-filled bubbles can be coupled to a targeting ligand using a flexible spacer arm, such as a branched or linear synthetic polymer (U.S. Pat. No. 6,245,318). A targeting ligand can be attached to the porous inorganic particles by coating, adsorbing, layering, or reacting the outside surface of the particle with the targeting ligand (U.S. Pat. No. 6,254,852).

Fluorescence Imaging

Non-invasive imaging methods can also comprise detection of a fluorescent label. A drug comprising a lipophilic component (therapeutic agent, diagnostic agent, vector, or drug carrier) can be labeled with any one of a variety of lipophilic dyes that are suitable for in vivo imaging. Representative labels include but are not limited to carbocyanine and aminostyryl dyes, preferably long chain dialkyl carbocyanines (e.g., Dil, DiO, and DiD available from Molecular Probes Inc. of Eugene, Oreg., United States of America) and dialkylaminostyryl dyes. Lipophilic fluorescent labels can be incorporated using methods known to one of skill in the art. For example VYBRANT™ cell labeling solutions are effective for labeling of cultured cells of other lipophilic components (Molecular Probes Inc. of Eugene, Oreg., United States of America).

A fluorescent label can also comprise sulfonated cyanine dyes, including Cy5.5 and Cy5 (available from Amersham of Arlington Heights, Ill., United States of America), IRD41 and IRD700 (available from Li-Cor, Inc. of Lincoln, Nebr.), NIR-1 (available from Dejindo of Kumamoto, Japan), and LaJolla Blue.

In addition, a fluorescent label can comprise an organic chelate derived from lanthanide ions, for example fluorescent chelates of terbium and europium (U.S. Pat. No. 5,928,627). Such labels can be conjugated or covalently linked to a drug as disclosed therein.

For in vivo detection of a fluorescent label, an image is created using emission and absorbance spectra that are appropriate for the particular label used. The image can be visualized, for example, by diffuse optical spectroscopy. Additional methods and imaging systems are described in U.S. Pat. Nos. 5,865,754; 6,083,486; and 6,246,901, among other places.

Radioimmunoguided System® (RIGS)

Another preferred application of the scFvs is in the Radioimmunoguided System®. This technique, also known as the RIGS® System involves the intravenous administration of a radiolabeled monoclonal antibody or its fragment prior to surgery. After allowing for tumor uptake and blood clearance of radioactivity, the patient is taken to the operating room where surgical exploration is effected with the aid of a hand-held gamma activity probe, e.g., Neoprobe®1000. This helps the surgeon identify the tumor metastases and improve the complications of excision. The RIGS® system is advantageous because it allows for the detection of tumors not otherwise detectable by visual inspection and/or palpation. See, O'Dwyer et al, Arch. Surg., 121:1 391-1394 (1986). This technique is described in detail in Hinkle et al, Antibody, Immunoconjugates and Radiopharmacouticals, 4:(3)339-358 (1991) (citing numerous references describing this technique). This reference also discloses the use of this technique with the CC49 monoclonal antibody itself. This technique is particularly useful for cancers of the colon, breast, pancreas, and ovaries.

In some embodiments, the scFvs of the presently disclosed subject matter are employed for in vivo imaging of tumors, wherein a composition of the presently disclosed subject matter that has been labeled with an imaging moiety such as a radio-opaque agent, a radioisotope, or other imaging agent is administered to a subject, and the presence and location of the detectably-labeled composition in the subject is assayed. This imaging technique can be useful in the staging and treatment of malignancies. In some embodiments, an antibody is labeled with any moiety that is detectable in situ in a subject, for example by nuclear magnetic resonance, radiology, or other detection methods known in the art.

As such, the presently disclosed subject matter also provides methods for detecting tumors in subjects. In some embodiments, the presently disclosed methods comprise (a) administering to the subject a composition comprising the scFv of the presently disclosed subject matter conjugated to a detectable label; and (b) detecting the detectable label to thereby detect the tumor.

Methods for Predicting the Recurrence and/or Progression of Cancer in a Subject

In some embodiments, the presently disclosed subject matter also provides methods for predicting the recurrence of cancer in a subject. In some embodiments, the methods comprise (a) isolating a biological sample comprising cells from a subject with a cancer; (b) contacting the biological sample with scFv of the presently disclosed subject matter; and (c) identifying in the biological sample one or more cells that bind to the scFv of the presently disclosed subject matter, whereby the recurrence of a cancer is predicted in the subject. With respect to these methods, the identification of cells that bind to the scFvs of the presently disclosed subject matter can be indicative of a recurrence of a subject's cancer when the subject had previously been negative for such circulating cells. In some embodiments, the presence of cells that bind to the one or more of the antibody fragments of the presently disclosed subject matter indicates that the subject is at enhanced risk of metastatic disease relative to a subject that is negative for such cells.

Methods for Prognosing Progression of Cancer

The presently disclosed subject matter also provides methods for prognosing progression of a cancer in subjects. In some embodiments, the methods comprise isolating a biological sample comprising cells from a subject with a cancer; contacting the biological sample with the scFv of the presently disclosed subject matter under conditions sufficient for the scFv to bind to an epitope present on a tumor and/or a cancer cell, if present, in the biological sample; and identifying in the biological sample one or more cells that bind to the scFv, whereby progression of a cancer is prognosed in the subject. In some embodiments, the biological sample comprises a blood sample, a lymph sample, or a fraction thereof. In some embodiments, the cancer is a adenocarcinoma or colon cancer.

As used herein, the phrase "prognosing progression of a cancer" refers to evaluating indicia of a cancer disease at a given time point and comparing the same to the indicia of the cancer disease taken at an earlier time point, wherein the comparison is indicative of a progression of the cancer in the subject. In some embodiments, progression of the cancer comprises metastasis of the cancer in the subject.

Other Uses

The antibodies of the presently disclosed subject matter can also be employed in various assay methods, such as but not limited to competitive binding assays, direct and indirect sandwich assays, and immunoprecipitation assays (see e.g., Zola, 1987; Harlow & Lane, 1988).

The antibodies of the presently disclosed subject matter also are useful as affinity purification agents. In this process, one or more antibodies are immobilized on a suitable support (such as, but not limited to a Sephadex resin or filter paper) using methods well known in the art. See e.g., Harlow & Lane, 1988.

Making scFvs

Also disclosed are methods of making scFvs comprising: (a) culturing an isolated cell comprising a vector comprising a nucleic acid sequence encoding an scFv as disclosed herein, under conditions such that said scFv is expressed; and (b) recovering said scFv from the cell.

As disclosed herein, the scFvs disclosed herein can be made by a variety of methods. Importantly, a VH and VL domain are present, and they are linked together. The VH and VL domains can comprise SEQ ID NOS 10 and 11, for example.

Having generally described the invention, the same will be more readily understood by reference to the following examples, which are provided by way of illustration and are not intended as limiting.

Without further description, it is believed that one of ordinary skill in the art can, using the preceding description and the following illustrative examples, make and utilize the alterations detected in the present invention and practice the claimed methods. The following working examples therefore, specifically point out preferred embodiments of the present invention, and are not to be construed as limiting in any way the remainder of the disclosure.

EXAMPLES

Example 1: Sequences and Purification Methods for Stable, High-Affinity Single-Chain Antibody Fragments that Bind to the Human Adenocarcinoma Marker TAG-72

Protein Sequences for 3E8.scFv and 3E8.scFv.Cys

```
3E8.scFv
                                             (SEQ ID NO: 1)
MKYLLPTAAAGLLLLAAQPAMAAHHHHHHGSSGGGENLYFQGSSGDIVMT

QSPDSLAVSLGERATINCKSSQSVLYSSNNKNYLAWYQQKPGQPPKLLIY

WASTRESGVPDRFSGSGSGTDFTLTISSLQAEDVAVYYCQQYYSYPLTFG

GGTKVEIKLSADDAKKDAAKKDDAKKDDAKKDLQVQLVQSGAEVKKPGAS

VKVSCKASGYTFTDHAIHWVRQAPGQRLEWMGYFSPGNDDFKYSQKFQGR

VTITADKSASTAYMELSSLRSEDTAVYYCARSWIMQYWGQGTLVTVSS

3E8.scFv.Cys
                                             (SEQ ID NO: 2)
MKYLLPTAAAGLLLLAAQPAMAAHHHHHHGSSGGGENLYFQGSSGDIVMT

QSPDSLAVSLGERATINCKSSQSVLYSSNNKNYLAWYQQKPGQPPKLLIY

WASTRESGVPDRFSGSGSGTDFTLTISSLQAEDVAVYYCQQYYSYPLTFG

GGTKVEIKLSADDAKKDAAKKDDAKKDDAKKDLQVQLVQSGAEVKKPGAS

VKVSCKASGYTFTDHAIHWVRQAPGQRLEWMGYFSPGNDDFKYSQKFQGR

VTITADKSASTAYMELSSLRSEDTAVYYCARSWIMQYWGQGTLVTVSSC
```

The sequences include the pelB leader sequence for periplasmic export with the signal peptidase sequence underlined (MKYLLPTAAAGLLLLAAQPAMA (SEQ ID NO: 3)), a cleavable 6×His tag with TEV protease recognition sequence (AHHHHHHGSSGGGENLYFQ (SEQ ID NO: 4)), a short linker (GSSG (SEQ ID NO: 5)), the VL domain derived from 3E8, a linker known as 205C (LSADDAKKDAAKKDDAKKDDAKKDL (SEQ ID NO: 6)) derived from a CC49 scFv, and the VH domain derived from 3E8.

DNA Sequences for Expression of 3E8.scFv and 3E8.scFv.Cys

```
3E8.scFv
                                             (SEQ ID NO: 7)
5'CATATGAAATATCTGTTACCTACTGCTGCTGCGGGCCTGCTATTA

TTAGCGGCACAACCAGCAATGGCGGCGCATCATCATCATCATCATGGGTC

CTCGGGCGGTGGCGAAAATCTGTATTTTCAGGGTAGCAGCGGCGATATTG

TGATGACCCAGAGCCCGGATAGTTTGGCCGTTAGCCTGGGCGAACGTGCG

ACGATTAATTGCAAGAGCAGCCAGAGCGTGCTTTACAGCAGCAACAATAA

GAATTACCTGGCGTGGTATCAGCAAAAACCCGGCCAGCCGCCGAAACTTT

TGATTTATTGGGCGAGCACCCGTGAAAGCGGCGTGCCGGATCGTTTCTCG

GGCTCAGGCAGCGGGACCGATTTTACGCTGACCATCAGCAGCCTTCAGGC

GGAGGATGTCGCGGTGTACTACTGCCAGCAGTATTACAGCTATCCGTTGA

CCTTTGGGGGAGGCACCAAAGTGGAGATCAAACTGAGCGCGGATGATGCT
```

-continued

```
AAGAAAGATGCGGCGAAGAAGGACGATGCGAAAAAAGACGACGCAAAA

AAGGATCTGCAGGTGCAGCTGGTGCAGTCGGGTGCGGAAGTGAAGAAAC

CTGGGGCGTCGGTGAAAGTGAGCTGCAAAGCGAGCGGCTATACCTTTACC

GATCATGCGATTCATTGGGTGCGTCAAGCGCCAGGCCAGCGTCTGGAATG

GATGGGCTATTTTTCCCCAGGCAACGATGATTTCAAGTATTCCCAGAAGTT

CCAAGGGCGCGTGACCATTACCGCCGATAAAAGCGCAAGCACCGCGTATA

TGGAGCTGTCCAGCCTGCGTAGCGAAGATACAGCGGTTTACTATTGCGCA

CGGAGCTGGATTATGCAATACTGGGGCCAGGGCACCCTGGTGACCGTGAG

CAGCTAAGGATCC3'
```

```
3E8.scFv.Cys
                                            (SEQ ID NO: 8)
5'CATATGAAATATCTGTTACCTACTGCTGCTGCGGGCCTGCTATTA

TTAGCGGCACAACCAGCAATGGCGGCGCATCATCATCATCATCATGGGTC

CTCGGGCGGTGGCGAAAATCTGTATTTTCAGGGTAGCAGCGGCGATATTG

TGATGACCCAGAGCCCGGATAGTTTGGCCGTTAGCCTGGGCGAACGTGCG

ACGATTAATTGCAAGAGCAGCCAGAGCGTGCTTTACAGCAGCAACAATAA

GAATTACCTGGCGTGGTATCAGCAAAAACCCGGCCAGCCGCCGAAACTTT

TGATTTATTGGGCGAGCACCCGTGAAAGCGGCGTGCCGGATCGTTTCTCG

GGCTCAGGCAGCGGGACCGATTTTACGCTGACCATCAGCAGCCTTCAGGC

GGAGGATGTCGCGGTGTACTACTGCCAGCAGTATTACAGCTATCCGTTGA

CCTTTGGGGGAGGCACCAAAGTGGAGATCAAACTGAGCGCGGATGATGCT

AAGAAAGATGCGGCGAAGAAGGACGATGCGAAAAAAGACGACGCAAAA

AAGGATCTGCAGGTGCAGCTGGTGCAGTCGGGTGCGGAAGTGAAGAAAC

CTGGGGCGTCGGTGAAAGTGAGCTGCAAAGCGAGCGGCTATACCTTTACC

GATCATGCGATTCATTGGGTGCGTCAAGCGCCAGGCCAGCGTCTGGAATG

GATGGGCTATTTTTCCCCAGGCAACGATGATTTCAAGTATTCCCAGAAGTT

CCAAGGGCGCGTGACCATTACCGCCGATAAAAGCGCAAGCACCGCGTATA

TGGAGCTGTCCAGCCTGCGTAGCGAAGATACAGCGGTTTACTATTGCGCA

CGGAGCTGGATTATGCAATACTGGGGCCAGGGCACCCTGGTGACCGTGAG

CAGCTGTTAAGGATCC3'
```

This sequence has been subcloned into plasmids pCOLD IV (under the control of the cspA promoter) and pHLIC (under the control of the T7 promoter), in both cases between NdeI and BamHI restriction sites. Expression of 3E8.scFv from pCOLD IV and pHLIC and 3E8.scFv.Cys from pCOLD IV and pHLIC has been demonstrated.

Method of Expression and Purification

Both scFvs are produced from bacterial expression with export to the periplasm, IMAC purification, and proteolytic cleavage of the 6×His tag (FIG. 1).

Expression from pCOLD IV: The ampicillin resistant plasmids (3E8.scFv or 3E8.scFv.Cys) were transformed into DH10B for cold-shock expression. Cells were grown at 37° C. in 2×YT shake flasks to OD600=0.7-1.0. At mid-log phase the flasks were plunged into ice water for 10 minutes. Next, the cells were induced with 0.2 mM IPTG and moved to 4° C. for 20 minutes. After cold shock, the flasks were returned to the shaker and grown for ~16 hours at 16° C.

Expression from pHLIC: The ampicillin resistant plasmids were transformed into DE3 (successful expression achieved in BL21 (DE3), C41 (DE3), C43 (DE3), C43 (DE3) pLysS, T7 Express LysY (NEB), T7 Express LysY/Iq (NEB)) bacterial strains for cold-shock expression. Cells were grown at 37° C. in 2×YT shake flasks to OD600=~1.0-1.5. At late-log phase the flasks were plunged into ice water for 10 minutes. Next, the cells were induced with 0.05 mM IPTG and moved to 4° C. for 20 minutes. After cold shock, the flasks were returned to the shaker and grown for about 16 hours at 16° C.

Purification from Bacteria: Cells were harvested by centrifugation at 8,000 g and resuspended (40 mL/1 L culture) in 30 mM Tris.HCl, 20% sucrose, pH 8. Spheroplasts from 1 L of culture were isolated by adding 30 mg lysozyme, 0.05 mg RNase (Pierce), 100 U DNase (Fisher), and 2 mM MgCl2. The suspension is mixed at 4° C. with a magnetic stir bar for 20 minutes before dilution with 80 mL of ice cold water. The diluted sample is stirred for another 30 minutes at 4° C. before centrifugation at 8,000 g. The antibody fragment is purified from the supernatant by immobilized metal affinity chromatography (IMAC). For each liter of culture, 1 mL of 50% Ni-NTA agarose (Thermo) is added to a pre-fitted column (Bio-Rad). Next, the supernatant is passed through the resin and the bound material is washed (50 mM Tris.HCl, 300 mM NaCl, 20 mM imidazole pH 8.0) before elution (50 mM Tris-HCl, 300 mM NaCl, 250 mM imidazole pH 8.0). The 6×His-TEV-3E8.scFv is digested overnight with 6×His-tagged TEV protease with 1 mM DTT. After cleavage, the sample is dialyzed into 50 mM potassium phosphate, 300 mM NaCl, pH 8. The hexahistidine tag and 6×His-fused TEV protease are removed by a second Ni-NTA column. Concentration and purity are assayed by SDS-PAGE and absorbance at 280 nm.

Purification of 3E8.scFv.Cys: The C-terminal cysteine variant is purified identically to 3E8.scFv with the following modifications. (1) All solutions are supplemented with 1 mM TCEP to prevent undesired disulfide bonds between the C-terminal cysteine residues. (2) The 3E8.scFv.Cys copurifies with a degradation product. To remove this protein, the 6×His-3E8.scFv.Cys was dialyzed into 50 mM acetate pH 5, 15 mM NaCl, 1 mM TCEP and ion exchange chromatography was performed with Resource S column (GE). The protein is eluted with increasing concentrations of NaCl in 50 mM acetate pH 5, 1 mM TCEP. The full-length scFv elutes at 450 mM NaCl and is easily separated from the contaminant which elutes at 600 mM NaCl. Post elution, the desired fractions are dialyzed into 50 mM potassium phosphate, 300 mM NaCl, pH 8 and TEV digested overnight. The 6×His-tag and TEV protease are removed by a second Ni-NTA column.

Addition of Extra Alanine Following the Signal Peptidase Cleavage Site

Initial purification of 3E8.scFv resulted in poor yields with the majority of the antibody fragment residing in the insoluble fraction. It appeared that the amino acid sequence of SEQ ID NO: 1 was a poor substrate for signal peptidase. To improve the cleavage reaction, a second alanine codon was inserted into the DNA sequence. The resulting protein product,

```
                                            (SEQ ID NO: 9)
MKYLLPTAAAGLLLLAAQPAMAAHHHHHHGSSGGGENLYFQGSSGDIV,
```

increases the fraction of soluble (membrane-liberated) antibody fragment.

Optimization of Periplasm Extraction

The purification methodology reported here is the result of empirical optimization that significantly deviates from standard periplasmic purification protocols. The most common approach is to resuspend the cells in TSE buffer (Tris-Sucrose-EDTA). In this protocol, after incubation in TSE, the cells are harvested from the osmotic fraction by centrifugation and resuspended in water supplemented with magnesium. After incubation in water, the sample is centrifuged to separate the periplasmic fraction and the cells. The periplasmic fraction is then dialyzed to remove residual EDTA before IMAC. This process generates excessively large volumes that complicate dialysis steps, or require concentration. In addition, some or all protein may be lost to the osmotic fraction. 3E8.scFv was purified in poor yield when executing this standard protocol.

To improve yield, the purification procedure was optimized and the amount of protein recovered from the osmotic and periplasmic fractions was quantified. It is thought that dialysis is necessary to remove residual EDTA before applying the protein to the Ni-NTA column. In fact, when the dialysis step was omitted, the amount of recovered protein decreased in both the osmotic and periplasmic fraction. It was then questioned whether or not the EDTA itself was necessary. EDTA chelates divalent cations resulting in membrane destabilization. When the procedure was repeated in the absence of EDTA, the dialysis step was no longer necessary. Here, an increased recovery in the osmotic fraction was obtained, but minimal material was isolated from the periplasmic fraction. Next, it was hypothesized that lysozyme could destabilize the membrane in lieu of EDTA. Once again, no dialysis was required and increased yields were seen in both fractions. Finally, the lysozyme protocol was modified by omitting the centrifugation and harvest step between Tris-Sucrose and water. This generated pure protein in the highest yield.

Effect of Expression Vessel

Early preparations of periplasmic scFvs resulted in slow growth and significant cell lysis. To deter cellular lysing, the protocol was switched from aeration baffled flasks to standard Erlenmeyer flasks and decreased shaking from 200 rpm to 100 rpm. These adaptions led to higher O.D.600 values with minimal lysing.

Physical Properties

Oligomeric State

The CC49 scFv from Pavlinkova (1999) was reported to be a mixture of monomer and dimer. The quaternary structure of both scFvs by gel filtration chromatography was assayed. 3E8.scFv has a molecular weight of 28 kDa, and elutes as a single species with a calculated molecular weight of 25 kDa. The engineered scFv of 3E8 is monomeric with no visible dimer or higher oligomer formation. CC49.scFv elutes earlier with a calculated molecular weight of 31 kDa, which suggests some degree of unfolding/expansion. Additionally, the CC49 chromatogram has a smaller second peak with calculated molecular mass of 64 kDa, corresponding to some dimer formation. The CC49.scFv exists as a heterogeneous mixture, and may be slightly expanded or unfolded.

Stability

The full-length IgG and both scFvs were assayed for stability to aggregation by Differential Static Light Scattering (DSLS) and High-Throughput Thermal Scanning (HTTS). DSLS measures the diffraction of 600 nm light with increasing temperature. As proteins unfold and aggregate, the precipitation products diffract light leading to high O.D.600 values. CC49.scFv undergoes a single cooperative transition with Tagg=54.0° C. (temperature where half the protein is aggregated). A similar transition is seen in 3E8.scFv, but the engineered variant is ~12° C. more stable (66.0° C.). The full-length antibody, 3E8.IgG is an additional 21° C. more stable than its truncated relative. These results show that the 3E8.scFv is significantly more stable to aggregation than CC49.scFv, but more aggregation-prone than the corresponding IgG.

A second technique for measuring protein stability is based on hydrophobic dye binding of thermally denatured intermediates (HTTS). Here, it is reported that THTTS values (temperature where half the protein is unfolded) that are highly concordant to the Tagg values shown for both scFvs (55.4° C.—CC49.scFv and 66.0° C.—3E8.scFv). The full-length IgG exhibits two unfolding transitions—one at 66.2° C., and a second at 83.6° C. The first transition overlaps the unfolding event seen for 3E8.scFv and can describe the unfolding variable domains. The second transition therefore corresponds to the unfolding of constant domains. These data taken together with the DSLS values, show that the increased stability of the constant domains prevent the IgG from aggregating, but both the scFv of 3E8 and the IgG are inactivated at 66° C. Therefore a single chain variable fragment has been successfully produced that is dramatically more stable than CC49.scFv and equal to the stability of 3E8.IgG.

Binding

Fluorescence Dot Blot

Figures 7A, 7B, 7C:
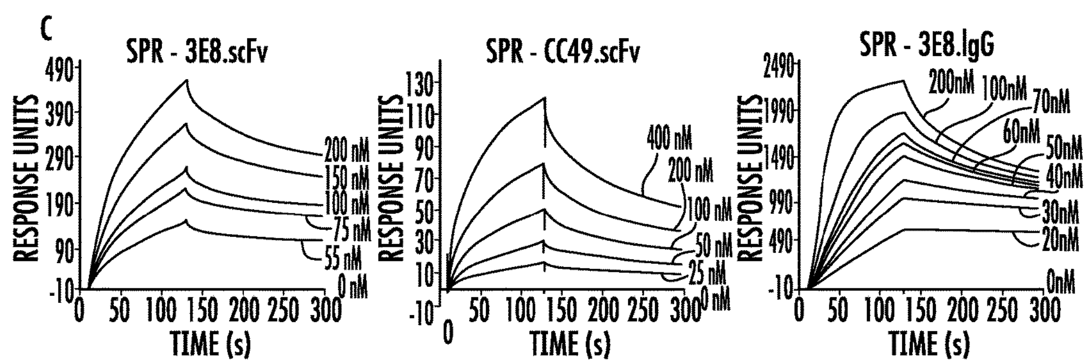
FIG. 7 shows antibody and fragment binding. A. Dot blot assay shows that both CC49.scFv and 3E8.scFv bind BSM (sialyl-Tn), but not BSA. B. Inhibition assay with fluorescent IgG and nonlabeled scFv shows that the scFv binds ~16-fold less strongly than the bivalent IgG. (−)* was performed with 0.25 μM IgG with no BSM. (−)** was performed using free fluorescein in the absence of antibody. C. SPR sensograms for each variant.

Bovine submaxillary mucin is positive for the TAG-72 epitope, sialyl-Tn. To qualitatively assay binding, BSM was spotted on a nitrocellulose membrane and then blocked with bovine serum albumin (BSA). The antibodies and fragments were labeled nonspecifically at lysines with the NHS-ester of fluorescein, and then were added to the dot blots. After gentle washing the samples were imaged using a Typhoon phosphorimager. The darker circle indicates a positive result for sialyl-Tn binding and was seen for both CC49.scFv and our engineered variant, 3E8.scFv (FIG. 7A).

Competition Dot Blot

Figure 3A:
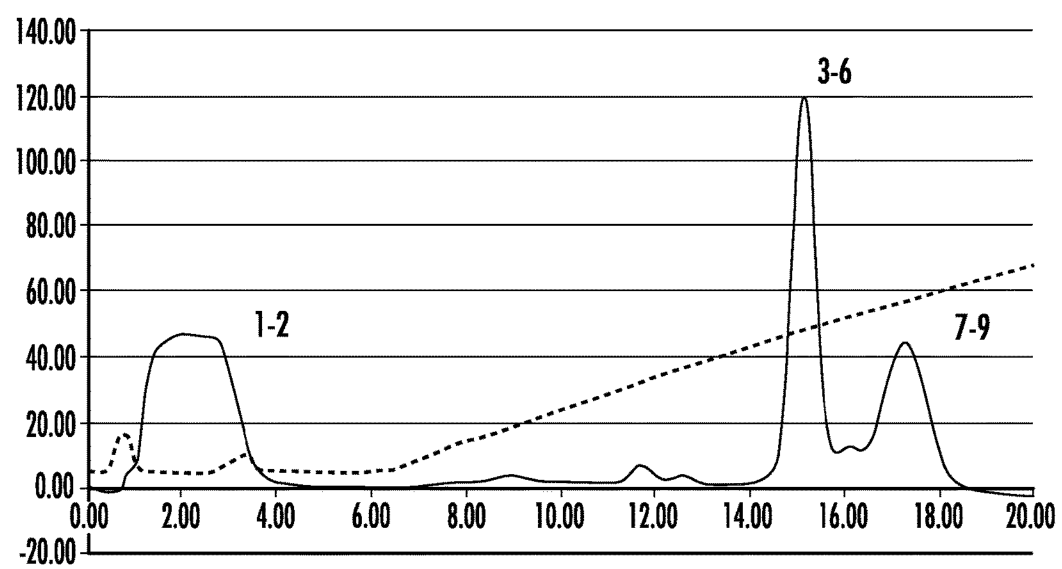
FIGS. 3A and B show purification of 3E8.scFv.Cys from its proteolytic fragment using cation exchange chromatography. The two species eluted from a Resource S column at 450 and 600 mM NaCl, with the authentic product eluting first. This was confirmed by SDS-PAGE. Lanes 1 and 12 are USB ladder, Lane 2: 3E8.scFv.Cys prior to ion exchange chromatography, Lanes 3-4: Fractions 1 and 2, Lanes 5-8: Fractions 3-6, Lanes 9-11: Fractions 7-9. The desired product is indicated with an asterisk.
Figure 3B:
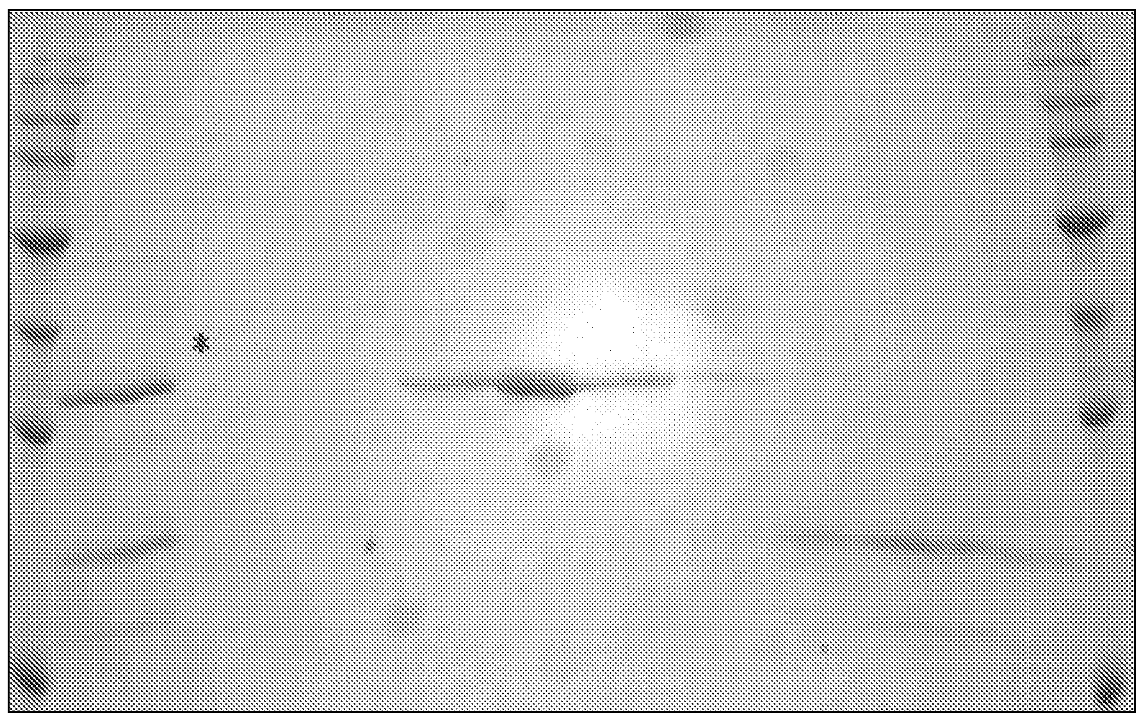
Figure 8:
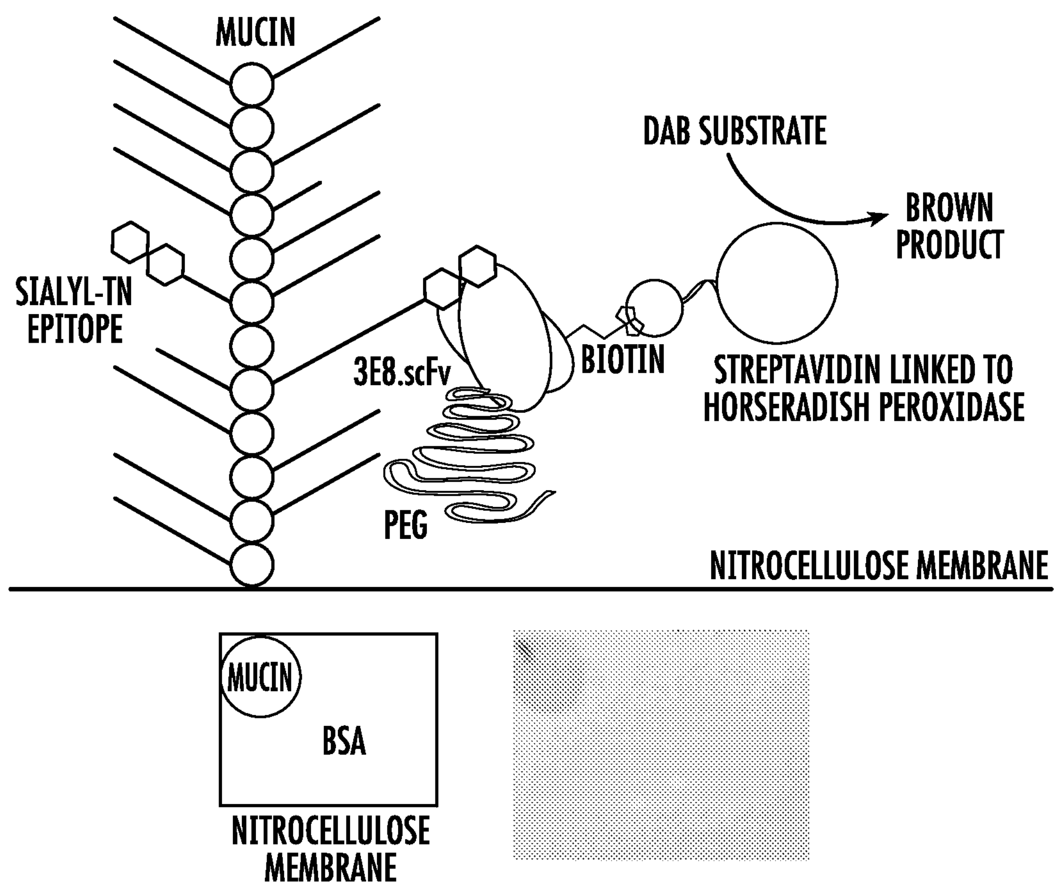
FIG. 8 shows dot blot assay using horseradish peroxidase as the reporter. Here, the scFv specifically binds the section of nitrocellulose that was blotted with mucin containing the TAG-72 epitope. The brown color is the result of the chemical reaction catalyzed by horseradish peroxidase, which is linked to the scFv by the biotin-streptavidin interaction.

A similar dot blot experiment was performed using constant concentrations of BSM and fluorescein-labeled 3E8 IgG. The assays were performed with increasing concentrations of unlabeled 3E8.scFv. If the scFv and IgG recognize the same epitope in BSM, and the scFv affinity is comparable to the IgG, one should see diminished fluorescence at increasing concentrations of scFv. Two negative controls were performed in parallel. First, the nitrocellulose membrane was prepared using only BSA to show that the antibodies do not bind nitrocellulose or BSA nonspecifically. Second, free fluorescein was added to the BSM dots to show that the interaction is not mediated by the fluorophore. As shown in FIG. 7B, 3E8 IgG binds strongly until ~2 μM competing 3E8.scFv. By 4 μM scFv about half of the IgG is displaced and by 8 μM the dot blot resembles the negative control. This analysis estimates that 3E8.scFv binds approximately 16-fold weaker than 3E8.IgG and both bind the same epitope. The slight loss in affinity is expected since the native IgG is bivalent versus the monovalent scFv.

Surface Plasmon Resonance

To further confirm the binding data, surface plasmon resonance was performed on 3E8 IgG, CC49.scFv, and 3E8.scFv (FIG. 7C). The 3E8 IgG has been previously reported to bind the sialyl-Tn epitope with a KD of ~1 nM (Yoon 2006). The commercially prepared 3E8 IgG was assayed by SPR and determined the affinity to be similar, 4±2 nM. CC49.scFv binds in the mid-nanomolar range with a dissociation constant of 30±8 nM. 3E8.scFv bound 2-fold more tightly than CC49.scFv and only 4-fold more weakly than the bivalent IgG. At 16±4 nM, 3E8.scFv binds better than clinically tested CC49 IgG and scFv variants of CC49, and has more desirable biophysical properties than full-length antibodies.

IHC

3E8.scFv was nonspecifically biotinylated (using NHS-biotin) to investigate its candidacy for immunohistochemistry (IHC), and to validate its ability to bind sialyl-Tn in human tissue. Generally, antibody was incubated with tissue before gentle washing and addition of a biotinylated secondary antibody. Next, streptavidin-linked horseradish peroxidase (HRPO) was added to the tissue in the presence of 3,3'-diaminobenzidine tetrahydrochloride (DAB). The oxidation of DAB results in a chromogenic product that stains localized tissue. The fragment was directly labeled with biotin at surface lysines. Before staining human tissue, a nitrocellulose dot blot analogous to FIG. 8A was performed successfully.

Figure 9:
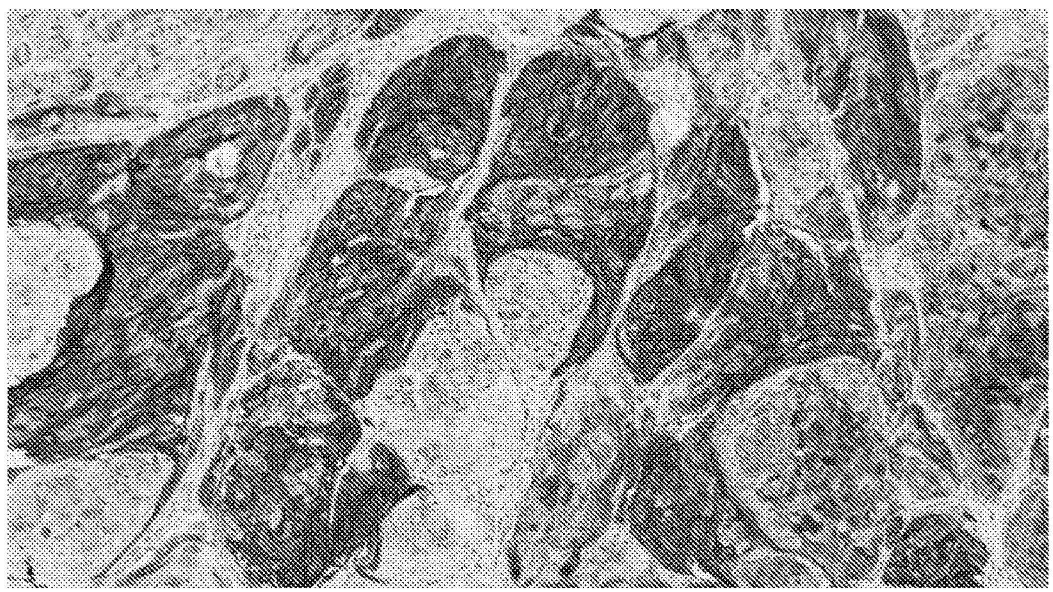
FIG. 9 shows immunohistochemical staining of human colon cancer. The scFv intensely stains the extracellular mucin and the intracellular vacuoles containing the TAG-72 epitope.

Diseased colon was obtained from surgical resection and embedded in paraffin before sectioning. The sample was stained with the commercial B72.3 kit (Biocare Medical) and 3E8.scFv. Both samples intensely stained the extracellular mucin, as well as mucin-filled intracellular vesicles (FIG. 9). Nonspecific binding in the two colon specimens tested was not detected.

Paraffin-embedded tissue was cut at 4 μm and sections were placed on positively-charged slides. Slides were then placed at 60° C. for one hour, cooled, deparaffinized and rehydrated through xylene and graded ethanol solutions to water. All slides were quenched for 5 minutes in 3% hydrogen peroxide to block endogenous peroxidase. Antigen retrieval was performed by Heat-Induced Epitope Retrieval (HIER) where slides are incubated in Target Retrieval Solution pH 6 (Dako) for 25 minutes at 96° C. Slides were stained with 5 μM scFv using a Dako Autostainer Immunostaining System at room temperature. Slides were counterstained in Richard-Allan hematoxylin, dehydrated through graded ethanol solution, cleared with xylene and coverslipped.

Conjugation of 3E8.scFv and 3E8.scFv.Cys

NHS-PEG

3E8.scFv was nonspecifically PEGylated at surface lysines using NHS-ester chemistry. A discrete PEG with molecule weight of 1.8 kD (Quanta BioDesign-10910) was reacted with the antibody fragment at 0, 5×, and 20× molar excess. The reaction proceeded in phosphate buffered saline for 1 hour at room temperature before quenching with ethanolamine. Unreacted PEG was removed by dialysis. Conjugation of a deuterated PEG for detection by Raman or IR spectroscopy was also demonstrated.

NHS-Fluorescein

3E8.scFv was nonspecifically labeled with fluorescein at surface lysines using NHS-ester chemistry. A NHS-fluorescein (Pierce-46410) was reacted with the antibody fragment at 20× molar excess. The reaction proceeded in phosphate buffered saline for 2 hour at 4° C. Unreacted fluorophore was removed by dialysis.

NHS-Biotin

3E8.scFv was nonspecifically labeled with biotin at surface lysines using NHS-ester chemistry. A NHS-biotin (Sigma-H1759) was reacted with the antibody fragment at 5× molar excess. The reaction proceeded in phosphate buffered saline for 1 hour at room temperature. Unreacted biotin was removed by dialysis.

Maleimide-PEG

3E8.scFv.Cys was specifically PEGylated at the C-terminal cysteine using maleimide chemistry. A discrete PEG with molecule weight of 2.7 kD (Quanta BioDesign-10931) was reacted with the antibody fragment at 20-fold molar excess. The reaction proceeded in phosphate buffered saline for 1 hour at room temperature. Unreacted PEG was removed by dialysis.

Example 2: Improving Therapeutic Protein Through PEGylation: Cancer Imaging Antibodies A modern cancer-imaging system, radioimmunoguided surgery (RIGS), utilizes radionuclide-labeled antibodies that bind to an epitope present only on certain cancer cells. Studies on the covalent attachment of polyethylene glycol molecules (PEGs) to proteins indicate that PEGylation can improve therapeutic effectiveness. Disclosed herein are the effects of PEGylation (using different types of PEG) with the end-goal of improving 3E8.scFv as a RIGS antibody. Described herein is what PEGs actually do to the protein to which they are attached. Differentiation between two models, PEG-protein interaction: polymer-like beads near the attachment point vs. wrapping around the protein like thread, is examined. A model protein (T4 lysozyme, T4L) is used to observe the general behavior of PEGylated proteins and to compare the different types of PEGs. An analysis of the effects of PEGylation with SDS polyacrylamide gel electrophoresis (PAGE) and a lysozyme activity assay is analyzed. Circular dichroism is used to do an in depth analysis to measure folding; gel filtration chromatography to measure size; differential static light-scattering and high-throughput thermal scanning to measure stability; and analytical ultracentrifugation and small-angle x-ray scattering to measure size/shape.

A PEGylation procedure that attaches activated PEGs to T4L or 3E8.scFv has been developed. SDS-PAGE analysis indicates proteins with integer numbers of attached PEGs. The activity of T4L and the binding of 3E8.scFv (PEGylated and unPEGylated) has been assessed using a fluorescence-based activity assay and surface plasmon resonance and immunohistochemistry binding assays, respectively.

The clinical applications of RIGS include that RIGS can be performed during surgery, eliminating hours of pre- and post-operative imaging. Furthermore, one can tune serum half-life of PEGylated proteins by changing the amount of PEGylation. One can also tune half-life of radionuclide to match the half-life of the antibody.

Traditional cancer imaging includes CT and PET scans, and is not very sensitive or specific. Modern cancer imaging uses Radioimmunoguided Surgery (RIGS), which uses radio-labeled antibodies raised against a disaccharide(sialyl-TN) present on tumor-associated glycoprotein (TAG-72) which is present on the surface of many cancer cells. It is very sensitive and very specific. The antibody currently used is CC49. 3E8 is a good binder, and can be modified into a single chain variable fragment (scFv) as disclosed herein.

It has been shown that attaching PEGs to proteins can improve the therapeutic properties of the protein. It can be attached to proteins (like the model protein, called T4L), at lysine residues using NHS-ester chemistry; at cysteine residues using maleimide chemistry. When attached to proteins, PEGs: are non-immunogenic, decrease aggregation and proteolysis, and increase serum half-lives.

PEGs exist as polydisperse mixtures of molecules, discrete (homogenous) molecules (dPEGs from Quanta Biodesign), and linear and branched molecules, as well as neutral and charged molecules. 3E8.scFv is a correctly folded monomer. It is as stable as the binding domain of 3E8.IgG. It has a KD=16.4 nM and binds correctly. PEGylated 3E8.scFv still binds to correct tissue. PEGylated T4L can be PEGylated with integer numbers of PEGs at lysine residues.

Example 3: Design and Biophysical Characterization of a Stabilized Single Chain Variable Antibody Fragment that Binds Tumor Associated Glycoprotein-72

Results

Construction and Purification

Figure 18:
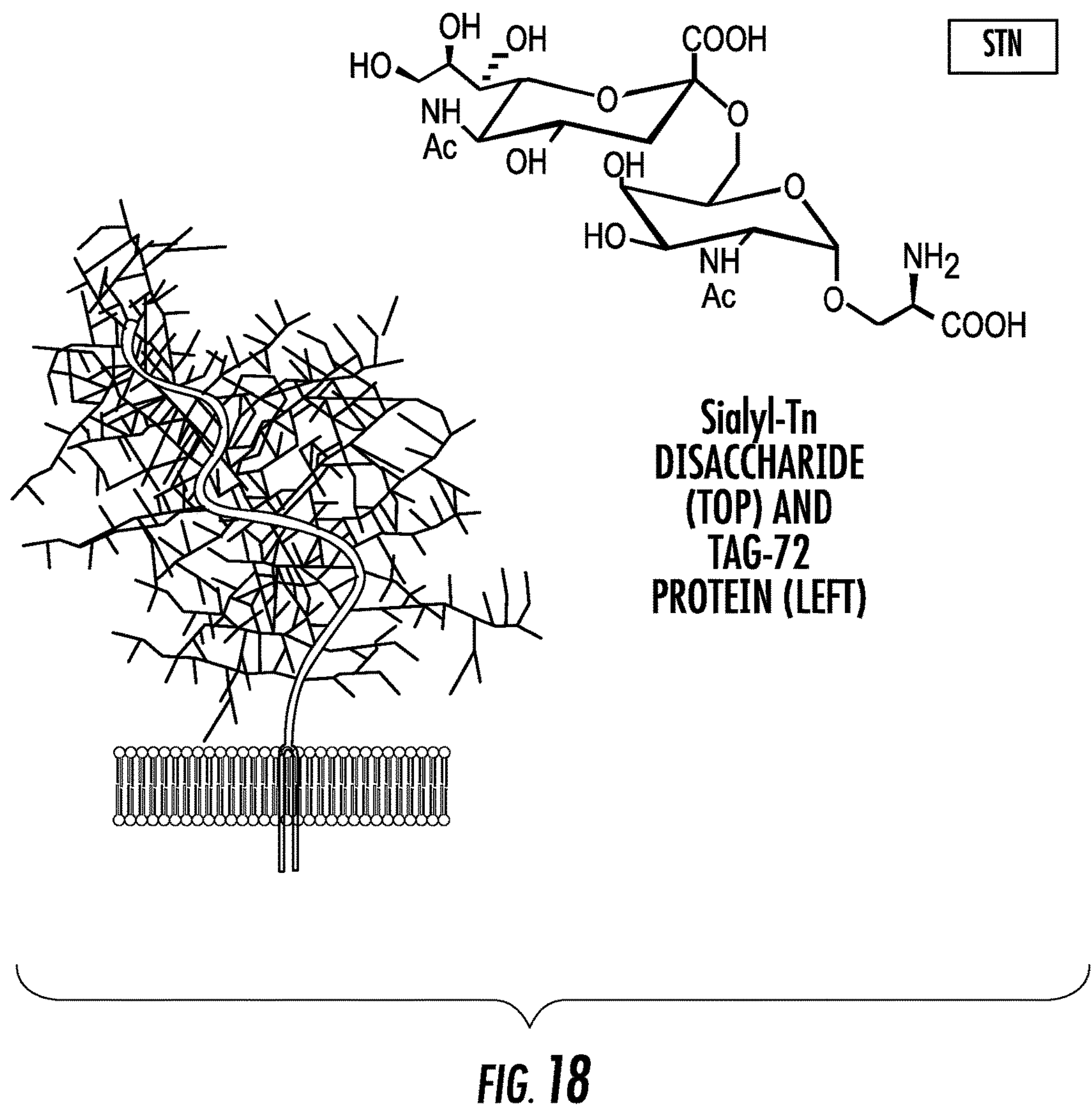
FIG. 18 shows Sialyl-Tn Disaccharide and TAG-72 protein.
Figure 19:
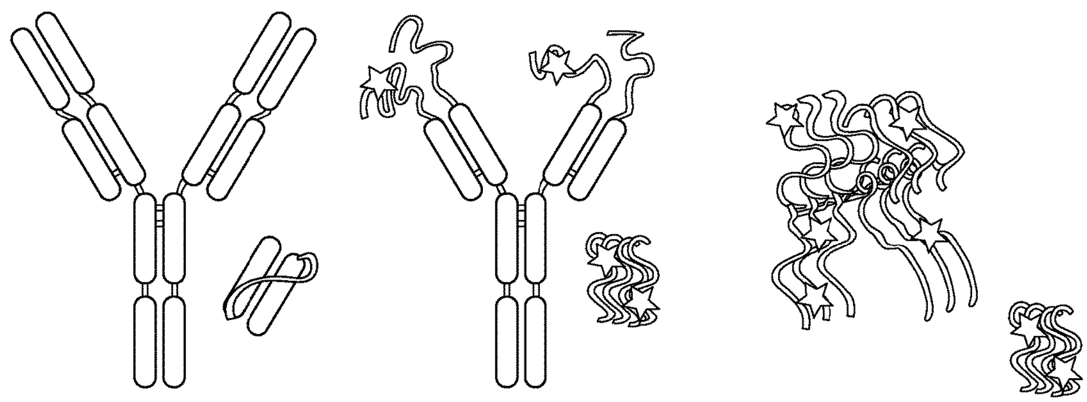
FIG. 19 shows antibody scaffolds depicted in gray bound to antigen (black stars). Also shown is the schematic for the scFv gene.

A detection and imaging agent for adenocarcinomas that express the TAG-72 epitope, sialyl-Tn, was discovered. Disclosed herein is a scFv inspired by 3E8 with carefully chosen linker sequences and improved expression and purification protocols. The variable light domain (VL) is fused to the variable heavy domain (VH) by the 205C linker sequence (Denzin 1991). The scFv is produced as a cleavable hexahistidine fusion and trafficked to the periplasm to enhance folding (FIG. 18). Finally, the full-length gene is subcloned into the pCOLD expression vector to make use of the cold-shock chaperone system (Takara Bio, Inc.).

The scFvs are purified from the periplasmic fraction using lysozyme digestion and osmotic shock. The modified protocol is preferred to standard procedures for its lack of large volumes, removal of dialysis steps, and compatibility with Ni-NTA purification. EDTA has been shown to destabilize the membrane by chelation of divalent calcium, but must be removed before nickel binding (Prachayasittkul 2007). Instead, the outer membrane is disturbed by mild lysozyme digestion. After osmotic shock, the periplasmic fraction can be directly bound to Ni-NTA agarose and purified by standard means. Addition of TEV protease and a second IMAC step yields native single chain variable fragments.

Under cold-shock conditions we are able to express and purify >2 mg $L^{-1}$ of 3E8.scFv in shake flasks, with the ability to increase production through fermentation. We also constructed a literature reported CC49.scFv as a control that under the same conditions yields ~1 mg $L^{-1}$ (Pavlinkova 1999).

Structure

Figure 20A:
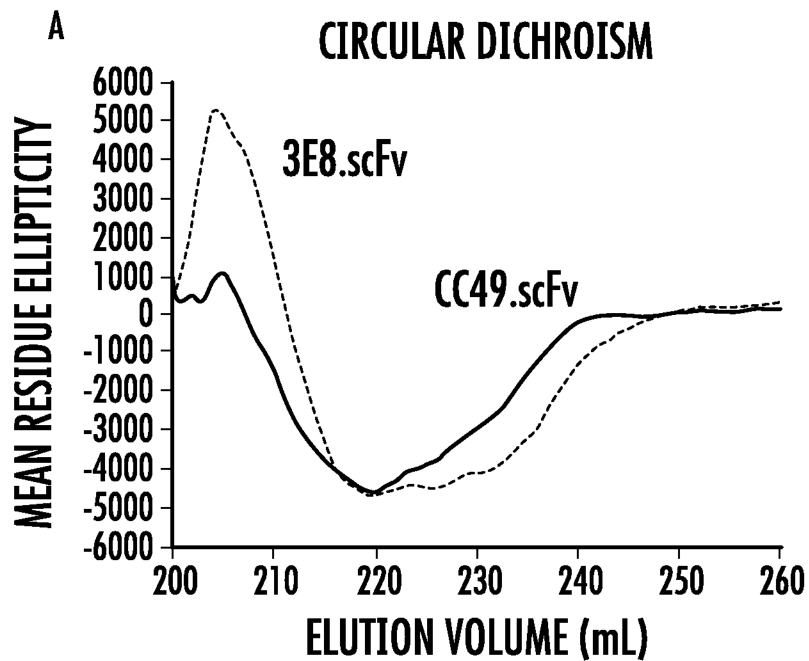
FIG. 20 shows the ScFv structure. A. CD wavelength scan of scFvs is consistent with the immunoglobulin domain fold. B. Gel filtration shows a single monomeric species for 3E8.scFv, but CC49 is slightly expanded and exists as a scFv.

Full-length IgGs consist of four polypeptide chains including two heavy (~50 kDa) and two light (~25 kDa) chains. The two heavy chains interact with each other and with the light chain both through noncovalent contacts and disulfide bonds. Antigen binding is achieved using the variable loops in the N-terminal domains of the heavy and light chains, both of which belong to the immunoglobulin fold. An immunoglobulin fold is comprised of 7-9 antiparallel β-strands (Bork 1994). These secondary structures form two β-sheets with Greek key architecture. To stabilize the $V_H$ and $V_L$ interaction in scFvs, an amino acid linker is used to connect the C-terminus of the $V_L$ domain to the N-terminus of $V_H$ domain. To assess the gross structural features of 3E8.scFv and CC49.scFv circular dichroism (CD) (FIG. 20*a*) was performed. CC49.scFv has the expected minima around 215-220 nm for β-strands. 3E8.scFv has a similar shape spectra, but also exhibits a large positive peak around 205 nm consistent with immunoglobulin domains. The 205C linker is predicted to possess some coiled structure which can lead enhanced signal at 222 nm.

Figure 20B:
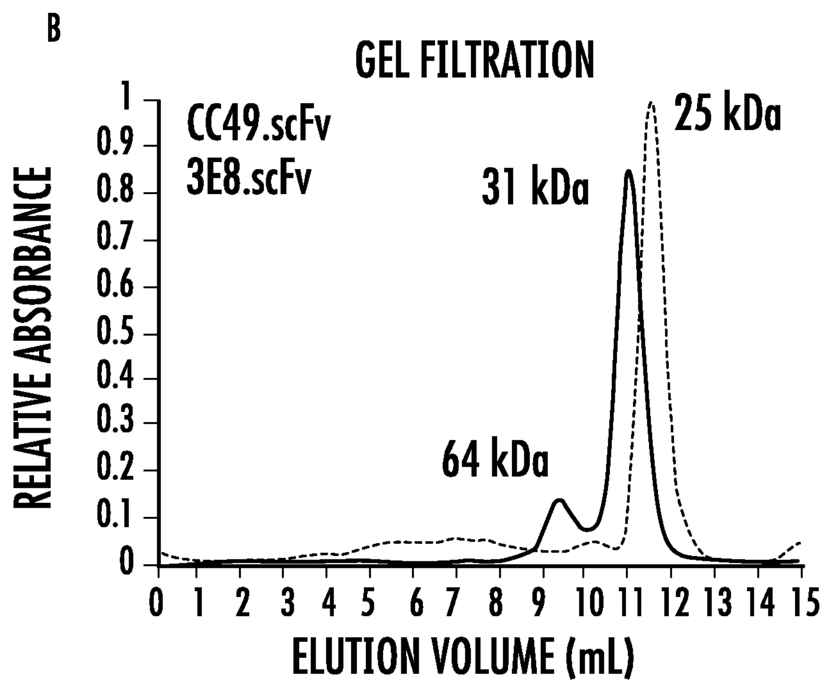
Figure 21:
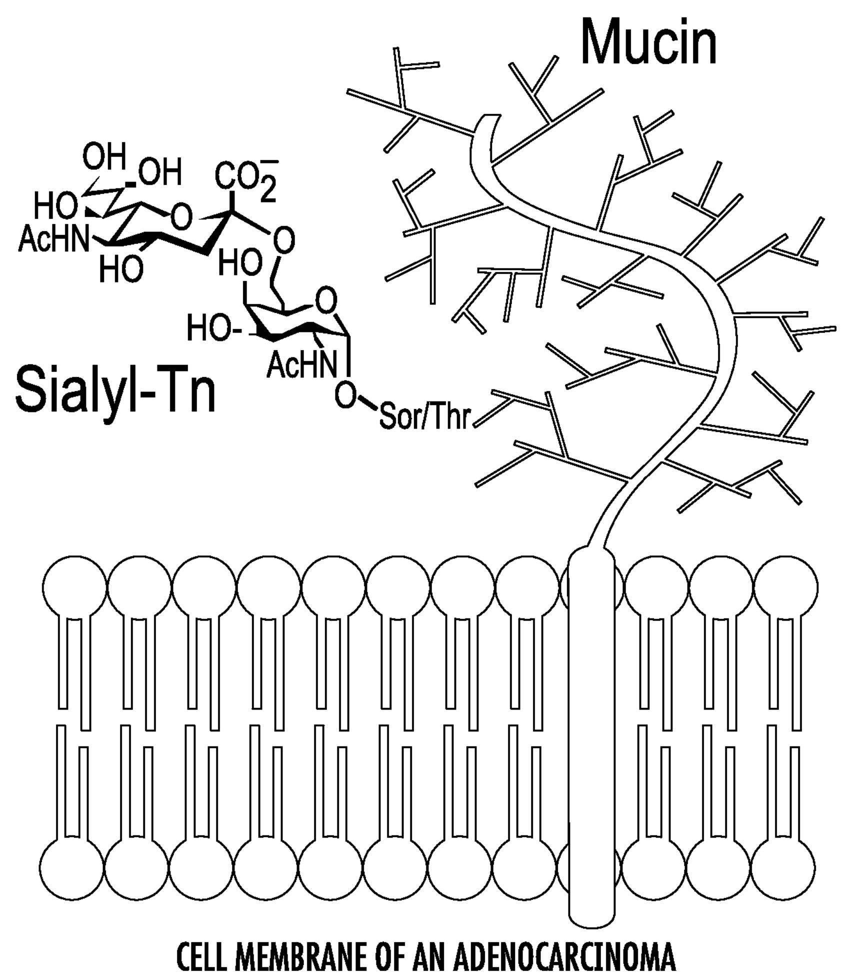
FIG. 21 shows that mucin is a large glycoprotein expressed and secreted from healthy and diseased cells. The mucin of adenocarcinomas has been shown to overexpress the disaccharide, Sialyl-Tn. This epitope is targeted with antibodies and antibody fragments.
Figures 22A, 22B:
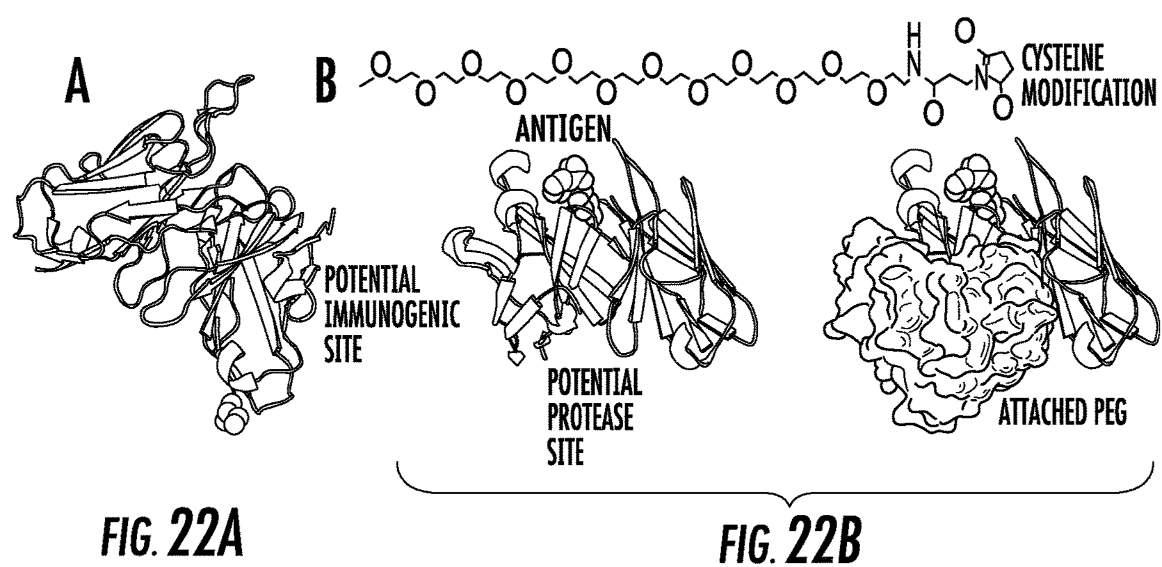
FIGS. 22A and 22B show PEGylation.

Next the quaternary structure of both scFvs by gel filtration were assayed. 3E8.scFv has a molecular weight of 28 kDa, and elutes as a single species with a calculated molecular weight of 25 kDa (FIG. 20*b*). The engineered scFv of 3E8 is monomeric with no visible dimer or trimer formation, nor aggregation. CC49.scFv elutes earlier with a calculated molecular weight of 31 kDa, which is 3 kDa greater than the predicted mass which shows some degree of unfolding or expansion.

Binding

Up regulation of metabolic genes in cancer cells leads to an increase in sialyl-Tn disaccharide display on mucin (Kjeldsen 1988). Molecules targeted to this epitope provide a powerful means for distinguishing cancerous and healthy tissue. Bovine submaxillary mucin is positive for the TAG-72 epitope, sialyl-Tn. To qualitatively assay binding, BSM was dotted on a nitrocellulose membrane and then blocked with bovine serum albumin (BSA). The antibodies and fragments were labeled nonspecifically at lysines with fluorescein, and then were added to the dot blots. After gentle washing the samples were imaged using a Typhoon phosphorimager. The darker circle indicates a positive result for sialyl-Tn binding and was seen for both our positive control, CC49.scFv, and our engineered variant, 3E8.scFv (FIG. 7*a*).

Next, a similar dot blot experiment was performed using constant concentrations of BSM and fluorescently-labeled 3E8.IgG. The assays were performed with increasing concentration of nonlabeled 3E8.scFv. If the scFv and IgG recognize the same epitope in BSM, and the scFv affinity is comparable to the IgG, one should see diminished fluorescence at increasing concentrations of scFv. Two negative controls were performed in parallel. First, the nitrocellulose membrane was prepared using only BSA to show that the antibodies do not bind nitrocellulose or BSA nonspecifically. Second, free fluorescein was added to the BSM dots to show that the interaction is not mediated by the fluorophore. As shown in FIG. 7*b*, 3E8.IgG binds strongly until ~2 μM competing 3E8.scFv. By 4 μM scFv about half of the IgG is displaced and by 8 μM the dot blot resembles the negative control. This analysis estimates that 3E8.scFv binds approximately 16-fold worse than 3E8.IgG and both bind the same epitope. The slight loss in affinity is expected since the native IgG is bivalent verse the monovalent scFv.

To further confirm the binding data, surface plasmon resonance on 3E8.IgG, CC49.scFv, and 3E8.scFv (FIG. 7*c*) was determined. The 3E8.IgG has been previously reported to bind the sialyl-Tn epitope with a $K_d$ of ~1 nM[7]. 3E8.IgG was assayed by SPR and it was determined that the affinity to be similar, 4±2 nM. Next the affinity of the scFv of CC49 was measured. CC49.scFv binds in the mid-nanomolar range with a dissociation constant of 30±8 nM. Finally, SPR was conducted on 3E8.scFv and found it to bind 2-fold better than CC49.scFv and only 4-fold weaker than the bivalent IgG. At 16±4 nM, 3E8.scFv binds better than clinically tested CC49.IgG and scFv variants of CC49, and has more desirable biophysical properties than full-length antibodies.

Immunohistochemistry

The single chain variable fragment of 3E8 was nonspecifically biotinylated to investigate its candidacy for immunohistochemistry (IHC), and to validate its ability to bind sialyl-Tn in human tissue. Generally, an antibody is incubated with tissue before gentle washing and addition of a biotinylated secondary antibody. Next, streptavidin-linked horseradish peroxidase (HRPO) is added to the tissue in the presence of 3,3'-diaminobenzidine tetrahydrochloride (Dab). The oxidation of Dab results in a chromogenic product that stains localized tissue. Because the scFv lacks the constant domain where the secondary antibody binds, our fragment was directly labeled with biotin at surface lysines. Before staining human tissue, a nitrocellulose dot blot analogous was performed successfully.

Diseased colon was obtained from surgical resection and embedded in paraffin before sectioning. The sample was stained with the commercial B72.3 kit and 3E8.scFv. Both samples intensely stained the extracellular mucin, as well as mucin-filled intracellular vesicles (FIG. 9).

Stability

Engineering a single chain variable fragment with enhanced stability and aggregation resistance was the goal. The full-length IgG and both scFvs were assayed for stability by Differential Static Light Scattering (DSLS) (Senisterra 2009) and High-Throughput Thermal Scanning (HTTS) (Lavinder 2009). DSLS measures the diffraction of 600 nm light with increasing temperature (FIG. 6*a*). As proteins unfold and aggregate, the precipitation products diffract light leading to high $O.D._{600}$ values. CC49.scFv undergoes a single cooperative transition with $T_{agg}$=54.0° C. (temperature where half the protein is aggregated). A similar transition is seen in 3E8.scFv, but the engineered variant is ~12° C. more stable (66.0° C.). The full-length antibody, 3E8.IgG is an additional 21° C. more stable than its truncated relative. These results alone show that the 3E8.scFv is significantly more stable than CC49.scFv.

A second technique for measuring protein stability is based on hydrophobic dye binding of thermally denatured intermediates (HTTS). Here, it is shown that $T_{HTTS}$ values (temperature where half the protein is unfolded) that are highly concordant to the $T_{agg}$ values shown for both scFvs (55.4° C.—CC49.scFv and 66.0° C.—3E8.IgG). The full-length IgG exhibits two unfolding transitions—one at 66.2° C., and a second at 83.6° C. (FIG. 6*b*). The first transition overlaps the unfolding event seen for 3E8.scFv and can describe the unfolding variable domains. The second transition therefore corresponds to the unfolding of constant domains. This data taken together with the DSLS values, show that the increased stability of the constant domains prevent the IgG from aggregating, but both the scFv of 3E8 and the IgG are inactivated at 66° C. Therefore a single chain variable fragment that is dramatically more stable than CC49.scFv and equal to the stability of 3E8.IgG has been produced.

Materials and Methods

Design and Construction

The scFv genes were designed as $V_L$-linker-$V_H$ fusions. The genes encode the PelB leader sequence for periplasmic trafficking, a hexahistidine tag for purification, and the recognition site for Tobacco Etch Virus (TEV) protease to remove the purification tag. The full-length DNA genes were ordered from Genewiz, Inc. (South Plainfield, N.J.) and subcloned into pCOLD IV (Takara Bio, Japan). The monoclonal antibody, 3E8.IgG was received as a gift from Enlyton, Ltd. (Columbus, Ohio).

Expression and Purification

The ampicillin resistant plasmids were transformed into DH10β for cold-shock expression. Cells were grown at 37° C. in 2×YT shake flasks to $O.D._{600}$=~0.7. At mid-log phase the flasks were plunged into ice water for 10 minutes. Next, the cells were induced with 0.3 mM IPTG and moved to 4° C. for 30 minutes. After cold shock, the flasks were returned to the shaker and grown for ~16 hours at 16° C.

Cells were harvested by centrifugation at 8000 g and resuspended (40 mL/1 L culture) in 30 mM Tris.HCl, 20% sucrose, pH 8. Spheroplasts from 1 L of culture were generated by adding 30 mg lysozyme, 0.05 mg RNase (Pierce), 100 Units DNase (Fisher), and 1.5 mM $MgCl_2$. The suspension was mixed at 4° C. with a magnetic stir bar for 30 minutes before dilution with 160 mL of ice cold water. The diluted sample was stirred for another 30 minutes at 4° C. before centrifugation at 8000 g. The supernatant was decanted and prepared for Ni-NTA binding by adding 4 mL of 0.5 M imidazole and 1 mL of 50% Ni-NTA agarose (Qiagen). After 1 hour of nickel binding at 4° C. the periplasmic fraction was poured into a prefritted column (Bio-Rad) and washed (50 mM Tris.HCl, 300 mM NaCl, 20 mM imidazole pH 8.0) before elution (50 mM Tris.HCl, 300 mM NaCl, 250 mM imidazole pH 8.0). The 6×His-TEV-scFvs were digested overnight with 6×His-TEV protease with 5 mM DTT. After cleavage, the sample was dialyzed into 50 mM potassium phosphate, 300 mM NaCl, pH 8. The hexahistidine tag and 6×His-TEV were removed by a second Ni-NTA column. Protein concentration and purity were assayed by SDS-PAGE and absorbance at 280 nm.

Circular Dichroism

Spectra were recorded on a Jasco J-185 spectrometer at 10 μM protein in 10 mM HEPES, 150 mM NaCl, 3.4 μM EDTA, 0.005% surfactant P20 (GE Healthcare). Wavelength scans were collected in triplicate from 190 to 275 nm with 2 second integration at 100 nm $min^{-1}$ scanning speed. Data collected with HT voltage greater than 600 V were discarded.

Gel Filtration

Size-exclusion chromatography was performed on a GE Pharmacia AKTA Purifier. Antibody fragments were injected at 10 μM and eluted from a Superdex 75 10/300 column (GE Amersham) with 50 mM Tris.HCl, 100 mM NaCl, pH 8 at 0.4 mL $min^{-1}$. Molecular weights for scFvs were calculated based on fits from known standards: aprotinin (6.5 kDa-14.6 mL), cytochrome c (12.5 kDa-12.9 mL), carbonic anhydrase (29.0 kDa-11.21 mL), and bovine serum albumin (66.5 kDa-9.2 mL).

Stability

The stability of the full-length antibody and scFvs were determined by High-Throughput Thermal Scanning (HTTS). Here, 5 μM protein was incubated with 5×SYPRO Orange dye (Invitrogen). The melts were assayed using a Bio-Rad C1000 thermal cycler with a ramp rate of 1° C. $min^{-1}$ at 0.2° C. intervals. The data were exported to Microsoft Excel 2010. The $T_{HTTS}$'s were calculated as the temperature with the maximum slope as determined from a 5° C. window around each point.

The temperature of aggregation was assayed by Differential Static Light Scattering (DSLS) using the absorbance feature of the Jasco J-185 spectrometer at 10 μM protein in 10 mM HEPES, 150 mM NaCl, 3.4 μM EDTA, 0.005% surfactant P20 (GE Healthcare). Data were collected in 1° C. steps with 6 second temperature equilibration, 1° C. $min^{-1}$ ramping, and 2 second integration. All melts were exported to Microsoft Excel 2010. The $T_{AGG}$'s were calculated as the temperature with the maximum slope as determined from a 5° C. window around each point.

Labeling

The antibody and fragments were nonspecifically labeled at surface lysines with a 20 molar excess of NHS-fluorescein (53209-Pierce). Labeling was confirmed with an Olis DM-45P fluorimeter. ScFv was labeled at surface exposed lysines with a 3 molar excess of NHS-biotin (H1759-Sigma). Excess labeling reagent was removed by dialysis into 50 mM potassium phosphate, 300 mM NaCl, pH 8.

Binding

Qualitative binding to sialyl-Tn was assayed by dot-blotting. First, 2 μL of 5 mg $mL^{-1}$ bovine submaxillary mucin (M3895-Sigma) was spotted on a nitrocellulose membrane. The membrane was allowed to dry overnight before blocking with 5 mg $mL^{-1}$ BSA. After overnight incubation, excess BSA was removed by washing before addition of fluorescein-labeled scFvs. The scFvs were incubated for 3 hours at room temperature before washing. Fluorescence was observed using a Typhoon phosphorimager with 488 nm excitation.

The epitope binding of the 3E8.scFv was assayed for its ability to inhibit 3E8.IgG binding. Here, 0.25 μM labeled 3E8.IgG competed with increasing concentrations of non-labeled 3E8.scFv (0 to 8 μM). The loss of fluorescence was observed using the Typhoon phosphorimager with 488 nm excitation.

The binding parameters were evaluated using surface plasmon resonance (SPR). BSM was immobilized on a CM5 dextran sensor chip using the GE Pharmacia amine coupling kit (BR-1000-50). Scouting conditions were 200 μg $mL^{-1}$ BSM in 100 mM sodium acetate, pH 4 for channel 2, and 10 μg $mL^{-1}$ BSA in 100 mM sodium acetate, pH 4 for channel 1. The immobilization protocol continued until 700 RU were obtained. Binding was measured as 2-1. Antibody and fragments were dialyzed into 10 mM HEPES, 150 mM NaCl, 3.4 μM EDTA, 0.005% surfactant P20 (GE Healthcare) and were assayed from 0-400 nM. Samples were bound for 120 seconds at 10 μL $min^{-1}$ and dissociation was measured for 180 seconds. The CM5 chip was regenerated between trials with 6 M guanidine and 200 mM acetic acid with no loss in activity. The average binding parameters were evaluated using the BIAevaluation software.

Immunohistochemistry

Paraffin-embedded tissue was cut at 4 μm and sections were placed on positively-charged slides. Slides were then placed at 60° C. for one hour, cooled, deparaffinized and rehydrated through xylene and graded ethanol solutions to water. All slides were quenched for 5 minutes in 3% hydrogen peroxide to block endogenous peroxidase. Antigen retrieval was performed by Heat-Induced Epitope Retrieval (HIER) where slides are incubated in Target Retrieval Solution pH 6 (Dako) for 25 minutes at 96° C. Slides were stained with 5 μM scFv using a Dako Autostainer Immunostaining System at room temperature. Slides were counterstained in Richard Allen hematoxylin, dehydrated through graded ethanol solution, cleared with xylene, and coverslipped.

Example 4: Single Chain Variable Fragments of 3E8, PEGylation, and Conjugation to 3E8cys.scFv Design and Cloning of Antibody Fragments A first-generation single-chain variable fragment (scFv) based on the affinity-optimized, humanized antibody, 3E8 (Yoon 2006). The parent antibody has been reported to bind to the sialyl-Tn epitope that is found in the tumor-associated glycoprotein-72 (TAG-72) with a dissociation constant in the range of 5-10 nM (Thor 1986; Thor 1987; Muraro 1988; Colcher 1988). scFv fragments are monomeric and dimeric fusions, respectively, of the binding domains of the antibody, and have molecular weights in the range of 25 and 50 kD, respectively (Bird 1988; Kortt 2001). In contrast to full-length IgGs and Fab fragments, these smaller fragments can be expressed in bacteria (Sandhu 1992; Pini 2000).

The variable domains of 3E8 were connected by the 205C linker with the following orientation: $V_L$-205C-$V_H$ Denzin, 1991). The sequence was appended with the PelB leader sequence to direct the protein to the periplasm of *E. coli*, a hexahistidine tag for purification, and TEV protease site for subsequent removal of the hexahistidine tag. The full-length open reading frame was cloned into the pHLIC plasmid for overexpression (Durani 2012). A second construct, 3E8cys.scFv, was generated by PCR of the parent construct with mutagenic primers. This variant places a single cysteine at the C-terminus of 3E8.scFv to allow site-specific PEGylation via maleimide chemistry. Both constructs were confirmed by DNA sequencing.

Expression and Purification of Antibody Fragments

Figure 4:
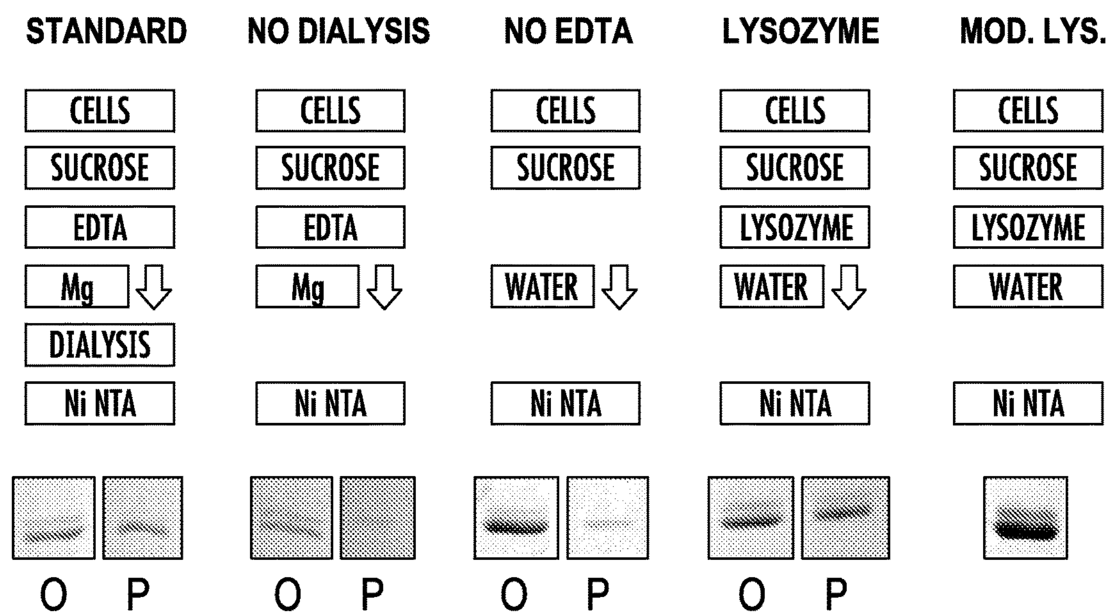
FIG. 4 shows optimization of periplasm extraction. The osmotic (O) and periplasmic (P) fractions are compared across nine purification methods. The modified lysozyme procedure yielded the best results. The faint band above the desired product is scFv with PelB leader sequence. When digested with TEV protease, both protein bands resolve to a single species. All samples purified are 3E8.scFv from pCOLD IV in DH10B.
Figure 5:
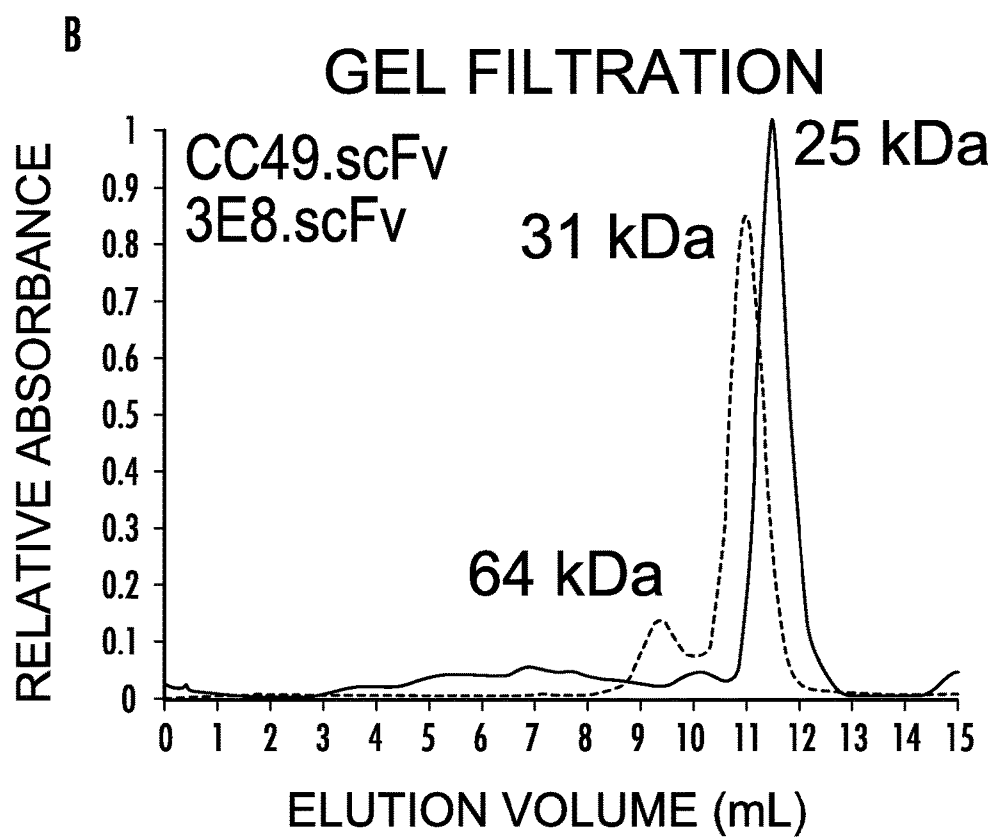
FIG. 5 shows gel filtration of antibody fragments. CC49.scFv is a heterogeneous sample that contains both monomer and dimer. Additionally, the fragment elutes as a slightly larger protein than its calculated molecular weight, showing some degree of unfolding or expansion. The 3E8.scFv elutes as a single species with molecular weight corresponding to a well folded monomer.

The constructs were transformed into C43(DE3) *Escherichia coli* for overexpression under the T7 promoter (Miroux 1996). Cultures were grown at 37° C. to $OD_{600}$=1.0 before cold shock and induction with 0.05 mM IPTG. The cells continued to express protein overnight at 16° C. The next morning, the cells were harvested, resuspended, and lysed by an Avestin Emulsiflex. The soluble fraction was recovered by centrifugation and purified by immobilized metal affinity chromatography (IMAC). The hexahistidine tags were cleaved by TEV protease and further purified by a second IMAC step (FIG. 20), to better than 90% purity. An additional ion exchange column was required to purify 3E8cys.scFv to near homogeneity due to the presence of what appears to be a proteolytic contaminant. Here, a Resource S cation exchange column separated the desired product from the 17 kD contaminant (FIG. 4). Under these conditions ~2 mg $L^{-1}$ of each scFv variant was purified, and have generated >10 mg from a single purification of material from 6 L of media in shake flasks.

Selection of PEGs and Conjugation

Figure 23:
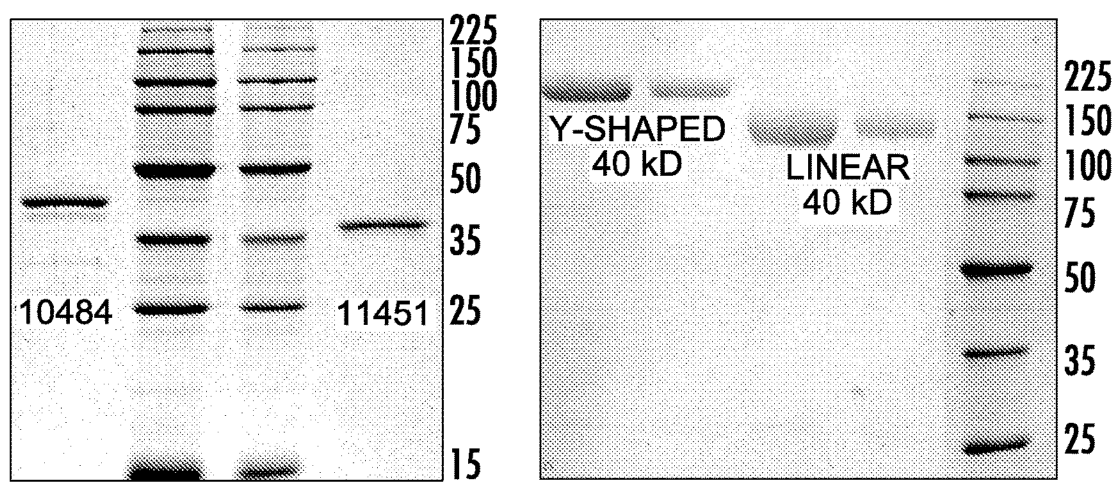
FIG. 23 shows crude modeling of 3E8.scFv reveals four lysines within the CDRs responsible for antigen binding.

PEGylation has been shown to increase the serum half-lives of antibody fragments by raising the hydrodynamic radius of the molecule, decreasing kidney filtration (Chen 2011; Veronese 2008). In addition, PEGylation has been reported to decrease proteolysis, immunogenicity, and aggregation. PEGs can be attached to proteins at lysines and cysteines via NHS-ester or maleimide activated PEGs, respectively. Crude modeling of 3E8.scFv reveals four lysines within the CDRs responsible for antigen binding (FIG. 23A). 3E8cys.scFv was engineered, which adds a C-terminal cysteine. This cysteine is expected to be the only free thiol within the antibody fragment, allowing for the site-specifically PEGylation of the scFv at a site distal to the antigen interaction surface.

Figure 24:
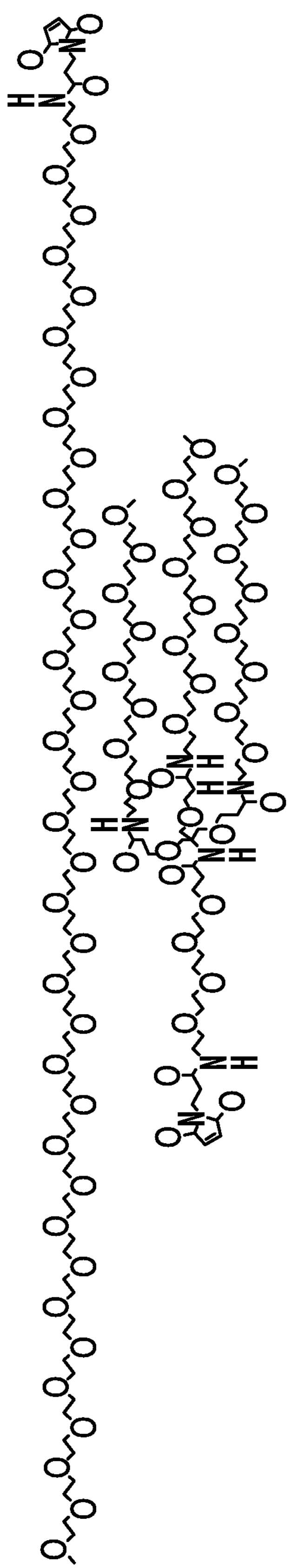
FIG. 24 shows PEGylated 3E8cys.scFv. Modified antibody fragments are shown on an SDS-PAGE gel. The 40 kD samples are loaded at 2× and 1× concentrations. PEG polymers do not strongly interact with SDS; therefore, their apparent masses are anomalous by SDS-PAGE compared to protein ladders. A linear and branched 1.8 kD PEG are shown.

PEGylate 3E8cys.scFv was chose for PEGylation with Quanta BioDesign's 10484 and 11451 PEGs. Both PEGs are discrete—meaning each molecule has an exact number of repeating polymer units ($(\text{—}CH_2\text{—}CH_2\text{—}O)_n$), as opposed to polydisperse PEGs which contain a distribution of numbers of monomeric units. The first PEG (10484) has a molecular weight of exactly 8,323.78 Da. It is a neutral PEG with three large arms each containing three further branches. The second PEG (11451) has a molecular weight of exactly 4,473.17 Da. It has three branches each terminating in a negatively charged carboxylic acid. To explore the effects of even larger PEGs linear and Y-shaped (branched) 40 kD PEGs were obtained from JenKem Technology USA. These large PEGs are polydisperse, but the polydispersity index for these molecules is 1.03, meaning that the PEG molecules have masses tightly distributed around 40,000 Da. All PEGs were activated with maleimide functional groups (FIG. 24 and Table 1).

TABLE 1

| | Mass (kD) | Type | Shape | Charge |
|---|---|---|---|---|
| 10484 | 8.3 | discrete | multiple branches | neutral |
| 11451 | 4.5 | discrete | branched | −3 |
| 40-L | ~40 | polydisperse | linear | neutral |
| 40-Y | ~40 | polydisperse | branched (Y-shaped) | neutral |

The protein samples were dialyzed into phosphate buffered saline (PBS) with 1 mM TCEP to keep the C-terminal cysteines reduced for PEGylation. The reactions proceeded to near completion overnight in the presence of ~50-fold molar excess PEG. Unreacted PEG and unmodified 3E8cys.scFv were removed by ion exchange chromatography followed by dialysis into PBS. Between 150-350 μg of each compound was generated.

Binding of 3E8.scFv and PEGylated Antibody Fragments

The purified antibody fragments were analyzed for binding to immobilized bovine submaxillary mucin (BSM), which is positive for the Sialyl-Tn epitope, by surface plasmon resonance (SPR) (Goel 2000). From this data, the rate of association ($k_a$), rate of dissociation ($k_d$), and the equilibrium dissociation constant ($K_D$) can be determined.

The scFv of 3E8 binds the Sialyl-Tn epitope with low nanomolar affinity (12 nM). In fact, the scFv binds nearly as well as the bivalent IgG (4 nM). The three non-PEGylated constructs all bind the antigen better than clinically investigated CC49 IgG (~30 nM)[15]. 3E8cys.scFv shows slightly lower apparent binding affinity (3-fold higher $K_D$), but on par with CC49. The binding of 3E8cys.scFv is slightly improved when PEGylated with 10484 and 11451; when PEGylated with the larger 40 kD PEGs, the binding is unperturbed.

Figure 25:
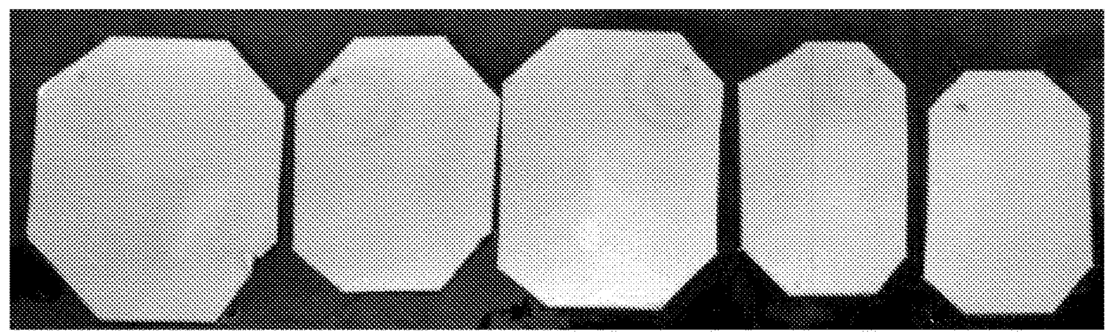
FIG. 25 shows replicates of 3E8cys.scFv+Y-40 kD binding to TAG-72 immobilized on nitrocellulose paper. The antigen was spotted on the corner of the paper indicated by pencil mark. Far right is the negative control, where all experimental steps were performed, but the paper was incubated with buffer in place of antibody fragment.
Figure 26:
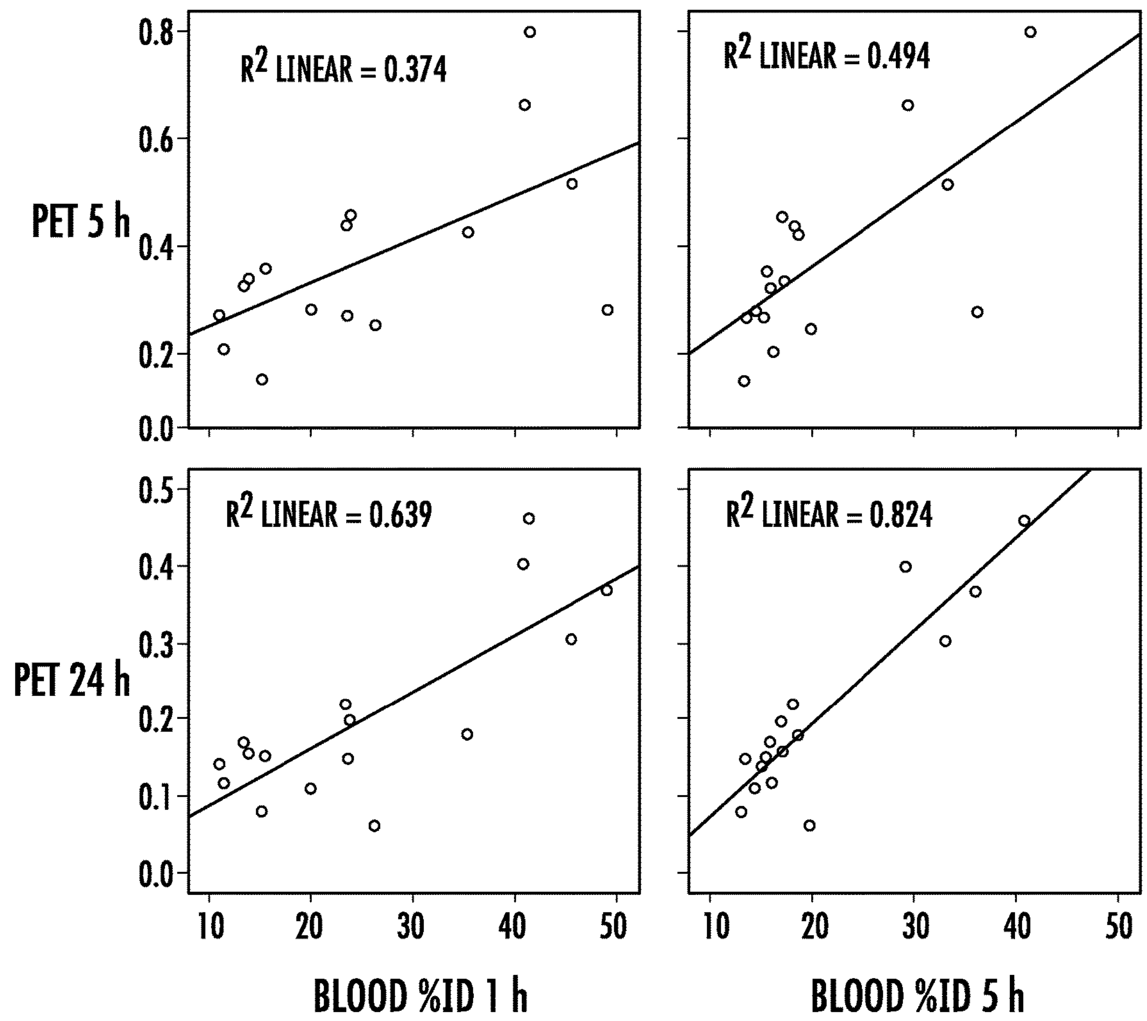
FIG. 26 shows correlation between serum half-lives and microPET/CT imaging. Blood radioactivity (% ID) of each individual mouse is plotted against its normalized tumor intensity in PET imaging. Upper panel, microPET/CT imaging at 5 h; bottom panel, microPET/CT imaging at 24 h. 5 and 24 h are the appropriate time points for a $^{123}$I-SPECT/CT radiopharmaceutical.
Figure 27:
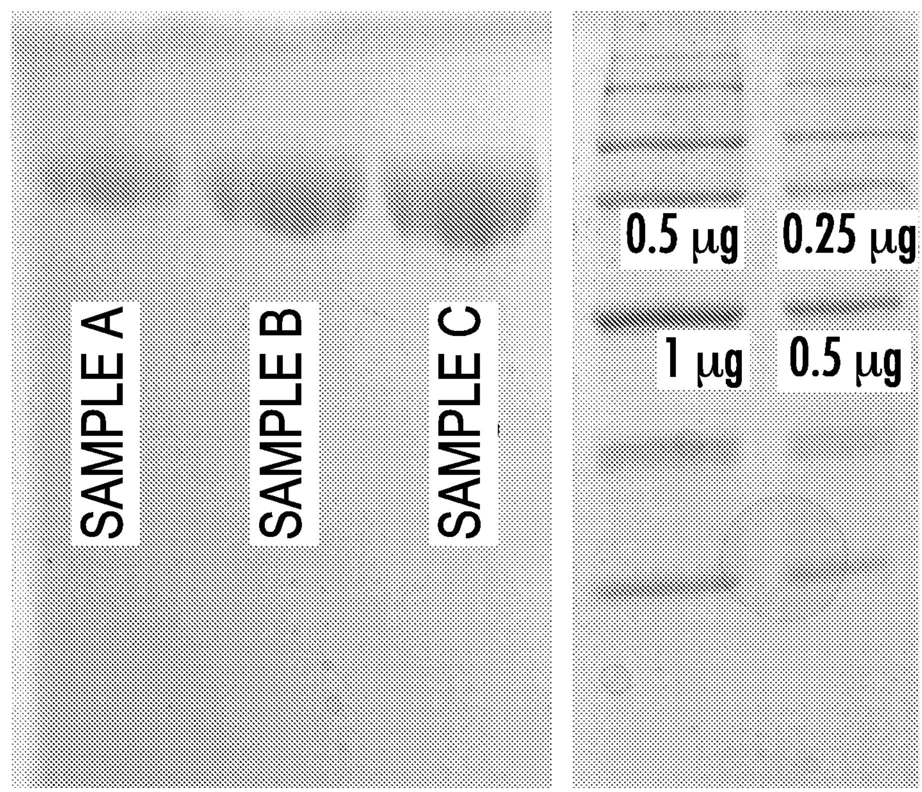
FIG. 27 shows 3E8cys.scFv was conjugated with a linear 30 kD PEG. Three antibody fragment aliquots were PEGylated and purified. Sample C provided the highest yield and purity, therefore, it was used for tumor imaging.
Figure 28:
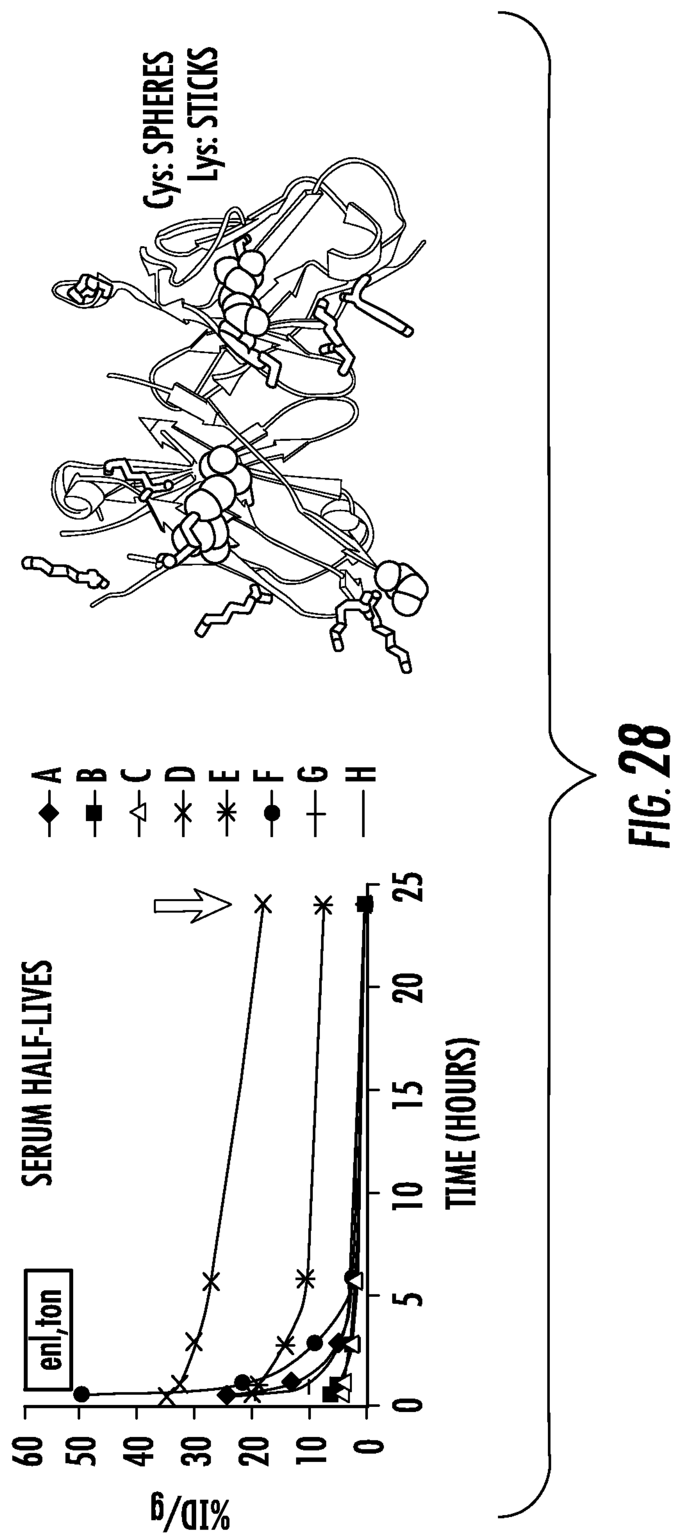
FIG. 28 shows the serum half-lives can be tuned with polyethylene glycol (PEG) conjugation. PEGylated antibody fragments are shown using lysines (NHS-ester chemistry) and cysteines (maleimide chemistry).
Figure 29:
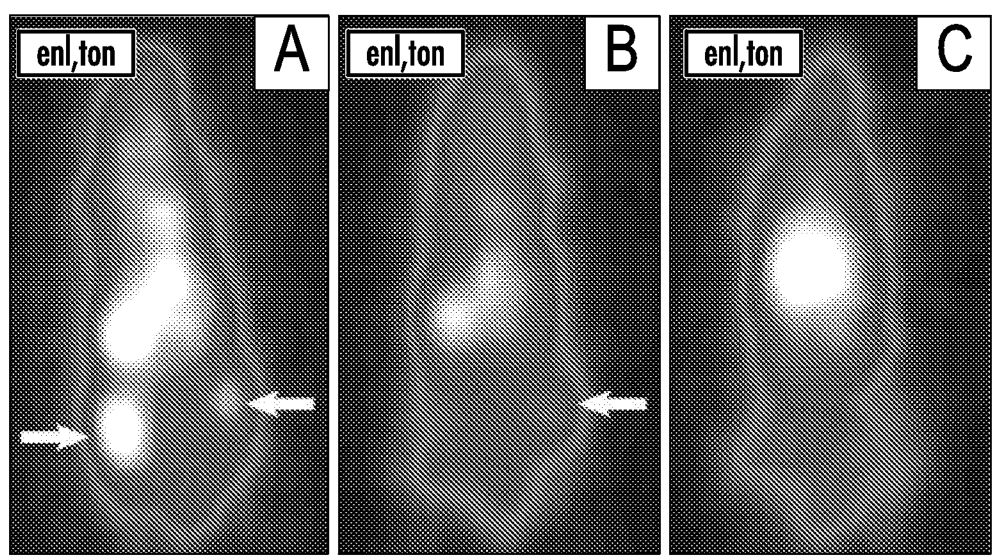
FIGS. 29A-C show proof-of-concept surgical resection with intraoperative imaging via the 123I-labeled antibody fragment. A. Image taken prior to surgery (tumors arrowed). B. A second image is taken to assess the surgical procedure. Note residual tumor remains on the right flank. C. Image taken after complete removal of cancerous tissue.

In addition, binding of these molecules has been validated by dot blots against bovine submaxillary mucin (FIG. 25). Here, nitrocellulose paper is spotted with mucin (TAG-72 positive) and blocked with BSA. The proteins are labeled with biotin for binding to streptavidin-horseradish peroxidase (HRP), and HRP development chemistry. A brown color indicates localization of the antibody fragment to TAG-72.

3E8.scFv's ability to target cancerous tissue by immunohistochemical (IHC) staining of colon tissue has been shown. Here, resected tissue was acquired from a patient with advanced colon cancer. The paraffin-embedded tissue was cut at 4 μm and sections were placed on positively-charged slides. 3E8.scFv was nonspecifically labeled at lysines with NHS-biotin and applied to the tissue with a Dako Immunostaining System. Next, streptavidin-linked HRP is added to the tissue in the presence of DAB. The oxidation of DAB by HRP results in a colored product that stains the localized tissue brown. FIG. 9 shows intense staining of the cancerous extracellular mucin as well as intracellular vesicles containing TAG-72. The scFv of 3E8 targeted the same sites as clinically-used B72.3.

Stability of Antibody Fragments

Antibody fragments with increased stability can have more favorable pharmacokinetic properties and to resist aggregation. The full-length 3E8.IgG and scFvs based on 3E8 and CC49 were assayed for stability by Differential Static Light Scattering (DSLS) and Differential Scanning Fluorimetry (DSF/HTTS) (Senisterra 2009; Lavinder 2009). DSLS measures the scattering of 600 nm light with increasing temperature (FIG. 10*a*), which is related to aggregation. CC49.scFv undergoes a single cooperative transition with $T_{agg}$=54.0° C. (temperature where half the protein is aggregated). A similar transition is seen in 3E8.scFv, but the engineered variant is ~12° C. more stable (66.0° C.). The full-length antibody, 3E8.IgG is an additional 21° C. more stable to aggregation than its truncated relative. These results alone show that the 3E8.scFv is significantly more stable than CC49.scFv.

Figure 10:
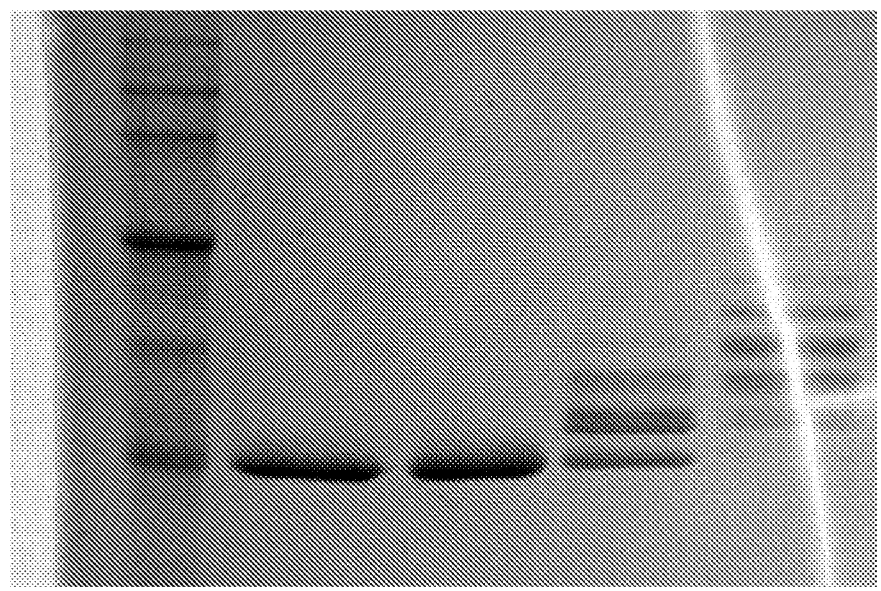
FIG. 10 shows NHS-PEGylation of 3E8.scFv. Lane 1: USB ladder, Lanes 2 and 3: Unmodified antibody fragment, Lane 4: Reaction with 5-fold molar excess of PEG, Lane 5: Reaction with 20-fold molar excess of PEG.
Figure 11:
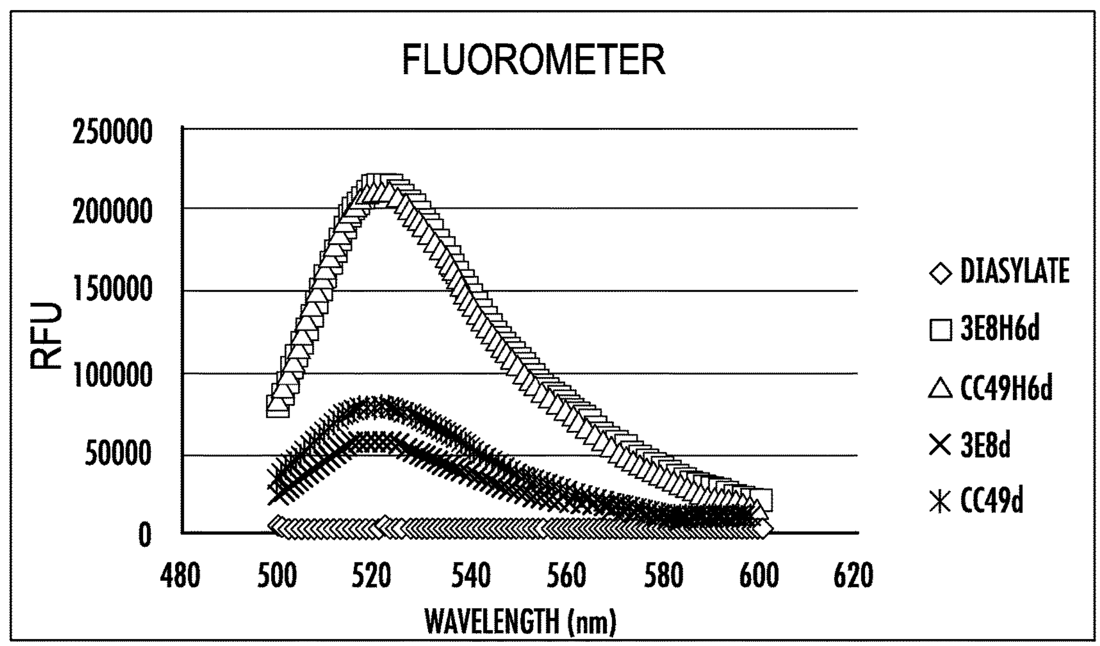
FIG. 11 shows fluorescent labeling of antibody fragments with and without 6×-His tags. The samples with hexahistidine tags (3E8H6d and CC49H6d) generate more intense signals due to increased concentrations of antibody fragment.
Figure 12:
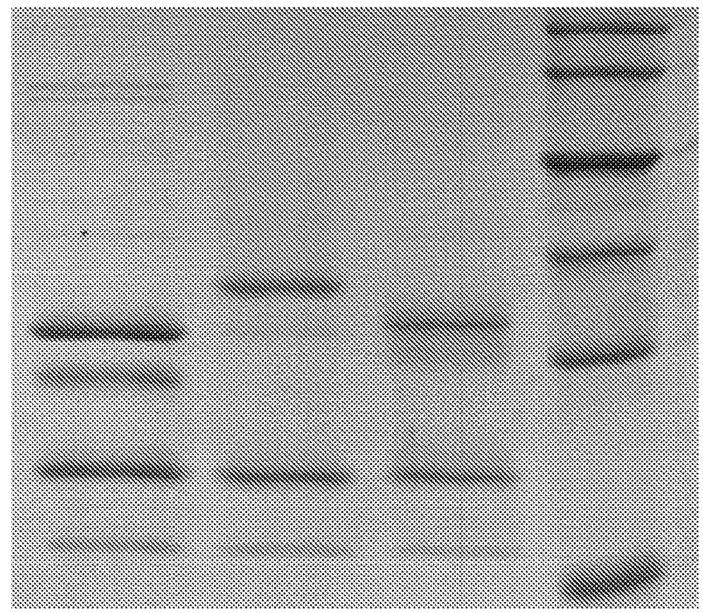
FIG. 12 shows the specific PEGylation of 3E8.scFv.Cys. The antibody fragment was labeled specifically at the C-terminal cysteine residue using maleimide chemistry. The scFv was nearly quantitatively PEGylated. Lane 1: partially purified, reduced 3E8.scFv.Cys, Lane 2: PEGylated 3E8.scFv.Cys. Lane 3: unrelated. Lane 4: ladder.
Figure 13:
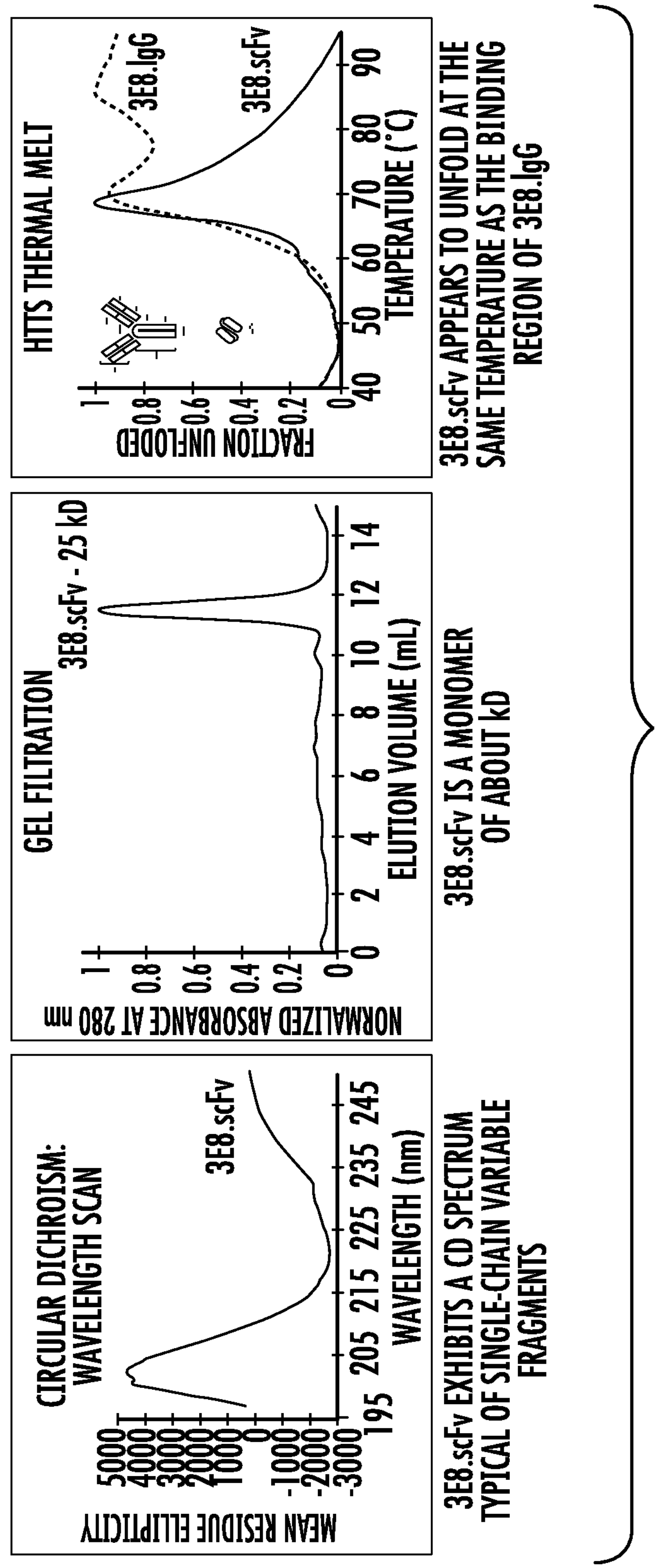
FIG. 13 shows the biophysical characterization of 3E8.scFv.
Figure 15:
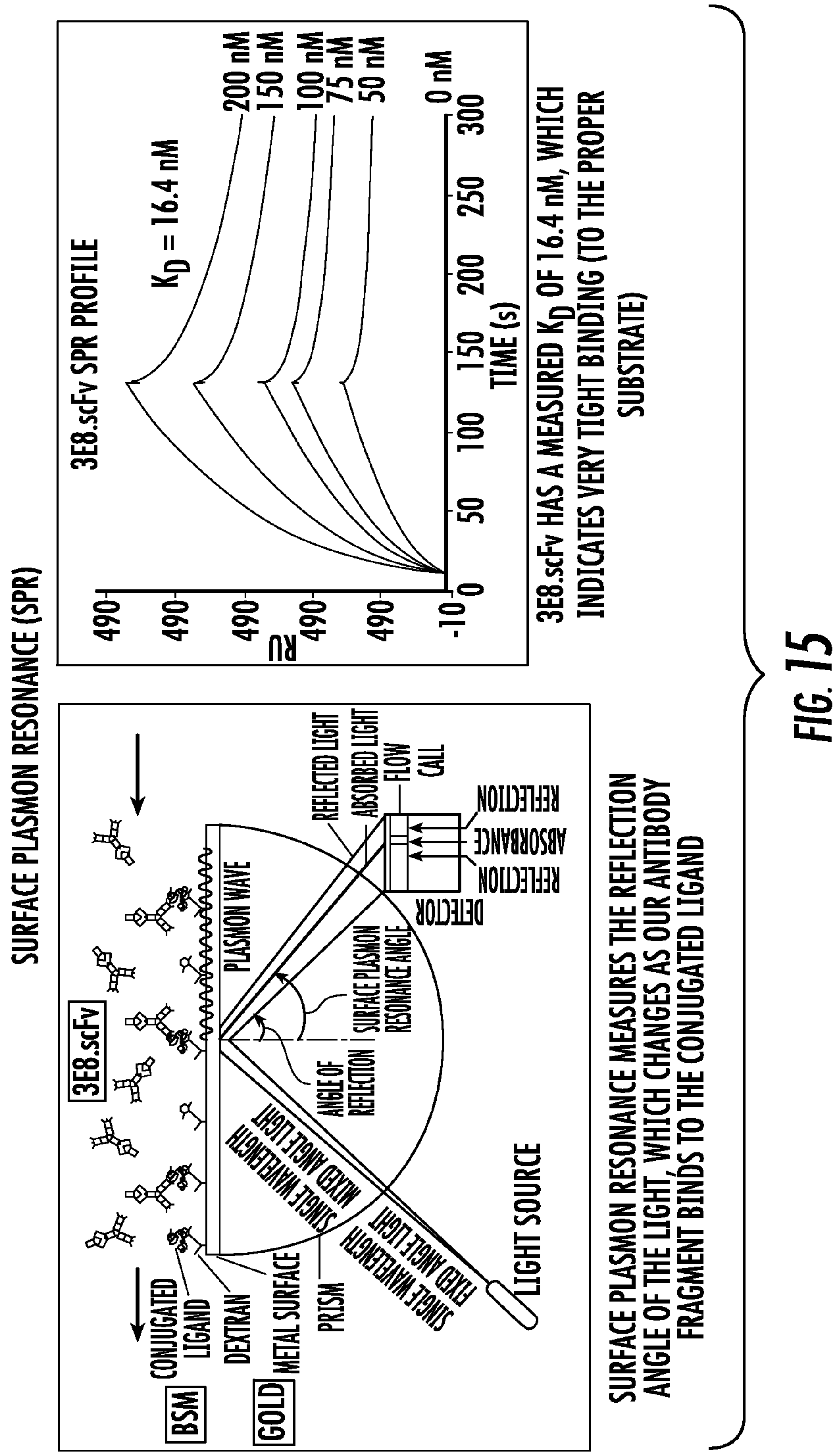
FIG. 15 shows surface plasmon resonance.
Figure 16:
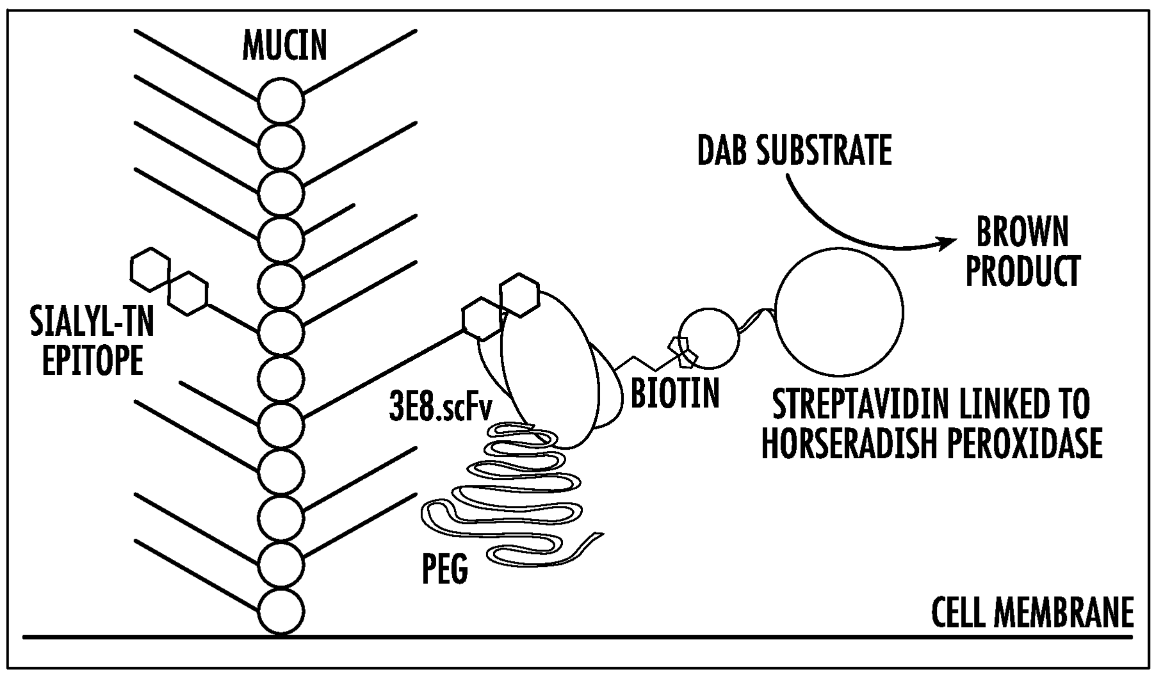
FIG. 16 shows immunohistochemistry. Biotin attached to 3E8.scFv via lysines can be coupled to a chromogenic enzyme complex which produces a brown product. Using this scheme, one can visualize 3E8.scFv bound to its epitope. Histologists can use this technique to analyze surgical specimens to determine the success of surgical procedures.

A second technique for measuring protein stability is based on hydrophobic dye binding of thermally denatured intermediates (DSF/HTTS). Here, we report $T_{DSF}$ values (temperature where half the protein is unfolded) that are highly concordant to the $T_{agg}$ values shown for both scFvs (55.4° C.—CC49.scFv and 66.0° C.—3E8.scFv). The full-length IgG exhibits two unfolding transitions—one at 66.2° C., and a second at 83.6° C. (FIG. 10*b*). The first transition overlaps the unfolding event seen for 3E8.scFv and therefore likely describes the unfolding variable domains. The second transition would therefore correspond to the unfolding of constant domains. These data taken together with the DSLS values suggest that the increased stability of the constant domains prevent the IgG from aggregating, but both the scFv of 3E8 and the IgG are inactivated at 66° C. Therefore a produced a single chain variable fragment has been produced that is dramatically more stable than CC49.scFv and equal to the functional stability of 3E8.IgG.

Radiolabeling and Pharmacokinetic Properties

The antibody fragments were first radiolabeled using the standard Iodogen method (Bailey 1996; Paus 1982). The free radioactive iodine was separated from labeled antibody by size exclusion chromatography and the fractions with the highest radioactivity were used for animal blood curves.

Radiolabeling

In a typical radiolabeling experiment, ~50-100 μg of protein was transferred to an Iodogen tube (Pierce, Rockford, Ill.) containing 100 μL phosphate buffer (0.1M, pH 7.4) followed by addition of known amounts of $^{125}$INa (Perkin Elmer, Waltham Mass.) or $^{123}$INa (Nordion, Ottowa, Ontario, Canada) in 0.02 M NaOH. An additional 50 μL of phosphate buffer (0.1M, pH 7.4) was then added to the mixture, it was covered with parafilm, and the mixture was incubated at room temperature for 30 to 45 min with occasional swirling. The labeled protein was loaded onto a Sephadex G-25 (PD-10) size-exclusion column and eluted with Phosphate Buffer Saline (PBS) to separate labeled protein from free $^{125/123}$I. Several fractions, containing approximately 10 drops, were collected and the fractions containing the highest radioactivity were collected and pooled in a pre-weighed plastic vial.

The amount of radioactivity was determined using a dose calibrator. The percent yield of radiolabeling was calculated by dividing the total radioactivity of the pooled samples by the amount of radioactivity added to the Iodogen tube. Purity of the samples was determined by Thin Layer Chromatography (TLC) strips (Whatman) eluted with 85% methanol: 15% water mixture. The bound protein did not migrate and unbound iodide moved to the solvent front.

Biodistribution and Pharmacokinetics

CC49 $^{124}$I-Fab'-dPEG molecules were studied using dPEG structures similar or identical to those used in this current study. The same tumors (LS-174T) and same TAG-72 target were used. In the Fab'-dPEG study of 4 different molecules, we measured the blood clearance curves from 1 to 24 hours and whole body microPET/CT imaging. A solid correlation between blood radioactivity at 5 and 24 hours and tumor intensity was found in microPET/CT images at both 5 and 24 hours post administration (FIG. 25). These time points (5 and 24 hours) are appropriate imaging times for the $^{123}$I-SPECT/CT imaging. The mouse blood curves from 1-24 hours were therefore good quantitative indicators of early time tumor uptake and retention. The full tissue biodistribution data are collected at 24 hours.

For evaluating blood clearance, at 0.5, 1, 3, 6, and 24 h, mice were anesthetized with isoflurane, and leg skin was sterilized with a 70% ethanol pad. The saphenous vein was punctured using a 25 G syringe needle and 5-10 μL of blood was collected using a capillary tube. The radioactivity of the blood samples was counted using the Wiz II gamma-counter and % ID/g was calculated using the same methods mentioned above. A blood factor of 78 mL/kg was used to calculate % ID for each mouse based on the individual weight of the mouse. Mean % ID was determined for each dose group at each time point.

Mice were sacrificed after the 24 h time point. Organs and tissues were dissected, including heart, lungs, spleen, liver, kidneys, pancreas, gastrointestinal tract (GI), muscle, skin, blood, tail, and carcass. Organs and tissues were then weighed, and radioactivity was counted using a gamma-counter (Perkin Elmer Wizard II, Model 2480, Waltham, Mass.).

It has now been shown that 3E8.scFv can be tuned from very short to very long serum half-lives by modulating the length and type of PEG polymer.

Pharmacokinetics Results

Inclusion of a 30 kD Linear PEG

The unmodified scFv filtered rapidly, and conjugation to 11451 and 10484 did not extend the serum half-lives of the 25 kD antibody fragment. Two 40 kD conjugates were studied that increase the total mass to 65 kD, which approximates the cut-off mass for first-pass renal clearance. These two molecules exhibited dramatic increases in serum residency. In fact, at 24 hours 8 and 18% serum activity were recorded for the linear and Y-shaped PEGs, respectively.

Animal Tumor Model

Animal studies were conducted in compliance with animal protocols approved at The Ohio State University Laboratory Animal Resource. Human colon adenocarcinoma cell line LS-174T was obtained from American Type Culture Collection (Manassas, Va.) and maintained in McCOY's 5A (Invitrogen, Carlsbad, Calif.) supplemented with 10% FBS (Invitrogen) and 1% penicillin and streptomycin (Invitrogen) at 37° C. with 5% $CO_2$. LS-174T cell line was passaged twice a week after being washed in PBS and trypsinization. For each antibody fragment, seven 4-6 week-old female athymic nu/nu mice (Charles River Laboratories, MA) were subcutaneously injected with $6\times10^6$ LS-174T cells in 100 μL of PBS on the right and left flanks Tumors were allowed to grow for 10 days and five mice with proper sizes on both flanks were recruited in the following studies. Potassium iodine (UPSHER-SMITH, MN) was in Clear$H_2O$ Hydro-Gels at 290 mg/L 24 hours prior to injection to block thyroid uptake of metabolized iodine.

Imaging with MicroSPECT/CT $^{123}$I-labeled 3E8 fragment proteins were injected at 1.8 mCi for 3E8cys.scFv+30 kD conjugate, per mouse via tail in 200 μL of PBS. N=4 mice were imaged. Micro-SPECT/CT (Inveon, Siemens Preclinical, Knoxville, Tenn.) imaging of mice was carried out at 5-7 and 20 h post-injection IV. Animals were anesthetized using isoflurane inhalation with 5% of dial vaporizer for induction and 1.5-2% for maintenance. The process of microSPECT/CT scanning lasted one hour at the 5 h time point and two hours at the 20 h time point. The difference was due to the decay of the $^{123}$I over one half life (13 h) and therefore much lower count rates at 20 h. The CT scans lasted three minutes. The microSPECT/CT images were reconstructed with the OSEM3D algorithm to try to lower possible artifact due to bladder contents and low localization counts. The discrepancy in threshold was due to a low signal to noise ratio (SNR) and differences in agent performance. These levels gave the best range across all samples to show clearance and background in the surrounding tissues. Large amounts of uptake in the stomach and bladder contents contributed to poor visualization. This however, did not often interfere with the region of interest (ROI) evaluations of the tumors. In all instances, the CT scan was used to assist in the determination of the tumor volume. The fasciae and subcutaneous fat gave enough tissue contrast to separate the xenograft in the CT volumes.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

REFERENCES

1. Jemal, A., Bray, F., Center, M. M., Ferlay, J., Ward, E. & Forman, D. (2011). Global cancer statistics. *CA Cancer J Clin* 61, 69-90.

2. Sun, D., Bloomston, M., Hinkle, G., Al-Saif, O. H., Hall, N. C., Povoski, S. P., Arnold, M. W. & Martin, E. W., Jr. (2007). Radioimmunoguided surgery (RIGS), PET/CT image-guided surgery, and fluorescence image-guided surgery: past, present, and future. *J Surg Oncol* 96, 297-308.

3. Thor, A., Ohuchi, N., Szpak, C. A., Johnston, W. W. & Schlom, J. (1986). Distribution of oncofetal antigen tumor-associated glycoprotein-72 defined by monoclonal antibody B72.3. *Cancer Res* 46, 3118-24.

4. Thor, A., Viglione, M. J., Muraro, R., Ohuchi, N., Schlom, J. & Gorstein, F. (1987). Monoclonal antibody B72.3 reactivity with human endometrium: a study of normal and malignant tissues. *Int J Gynecol Pathol* 6, 235-47.

5. Yokota, T., Milenic, D. E., Whitlow, M. & Schlom, J. (1992). Rapid tumor penetration of a single-chain Fv and comparison with other immunoglobulin forms. *Cancer Res* 52, 3402-8.

6. Colcher, D., Pavlinkova, G., Beresford, G., Booth, B. J. & Batra, S. K. (1999). Single-chain antibodies in pancreatic cancer. *Ann N Y Acad Sci* 880, 263-80.

7. Yoon, S. O., Lee, T. S., Kim, S. J., Jang, M. H., Kang, Y. J., Park, J. H., Kim, K. S., Lee, H. S., Ryu, C. J., Gonzales, N. R., Kashmiri, S. V., Lim, S. M., Choi, C. W. & Hong, H. J. (2006). Construction, affinity maturation, and biological characterization of an anti-tumor-associated glycoprotein-72 humanized antibody. *J Biol Chem* 281, 6985-92.

8. Bird, R. E., Hardman, K. D., Jacobson, J. W., Johnson, S., Kaufman, B. M., Lee, S. M., Lee, T., Pope, S. H., Riordan, G. S. & Whitlow, M. (1988). Single-chain antigen-binding proteins. *Science* 242, 423-6.

9. Sandhu, J. S. (1992). Protein engineering of antibodies. *Crit Rev Biotechnol* 12, 437-62.

10. Pini, A. & Bracci, L. (2000). Phage display of antibody fragments. *Curr Protein Pept Sci* 1, 155-69.

11. Yang, K., Basu, A., Wang, M., Chintala, R., Hsieh, M. C., Liu, S., Hua, J., Zhang, Z., Zhou, J., Li, M., Phyu, H., Petti, G., Mendez, M., Janjua, H., Peng, P., Longley, C., Borowski, V., Mehlig, M. & Filpula, D. (2003). Tailoring structure-function and pharmacokinetic properties of single-chain Fv proteins by site-specific PEGylation. *Protein Eng* 16, 761-70.

12. Muraro, R., Kuroki, M., Wunderlich, D., Poole, D. J., Colcher, D., Thor, A., Greiner, J. W., Simpson, J. F., Molinolo, A., Noguchi, P. & et al. (1988). Generation and characterization of B72.3 second generation monoclonal antibodies reactive with the tumor-associated glycoprotein 72 antigen. *Cancer Res* 48, 4588-96.

13. Colcher, D., Minelli, M. F., Roselli, M., Muraro, R., Simpson-Milenic, D. & Schlom, J. (1988). Radioimmunolocalization of human carcinoma xenografts with B72.3 second generation monoclonal antibodies. *Cancer Res* 48, 4597-603.

14. Divgi, C. R., Scott, A. M., Dantis, L., Capitelli, P., Siler, K., Hilton, S., Finn, R. D., Kemeny, N., Kelsen, D., Kostakoglu, L. & et al. (1995). Phase I radioimmunotherapy trial with iodine-131-CC49 in metastatic colon carcinoma. *J Nucl Med* 36, 586-92.
15. Kashmiri, S. V., Shu, L., Padlan, E. A., Milenic, D. E., Schlom, J. & Hand, P. H. (1995). Generation, characterization, and in vivo studies of humanized anticarcinoma antibody CC49. *Hybridoma* 14, 461-73.
16. Denzin, L. K., Whitlow, M. & Voss, E. W., Jr. (1991). Single-chain site-specific mutations of fluorescein-amino acid contact residues in high affinity monoclonal antibody 4-4-20. *J Biol Chem* 266, 14095-103.
17. Prachayasittikul, V., Isarankura-Na-Ayudhya, C., Tantimongcolwat, T., Nantasenamat, C. & Galla, H. J. (2007). EDTA-induced membrane fluidization and destabilization: biophysical studies on artificial lipid membranes. *Acta Biochim Biophys Sin* (*Shanghai*) 39, 901-13.
18. Pavlinkova, G., Beresford, G. W., Booth, B. J., Batra, S. K. & Colcher, D. (1999). Pharmacokinetics and biodistribution of engineered single-chain antibody constructs of MAb CC49 in colon carcinoma xenografts. *J Nucl Med* 40, 1536-46.
19. Bork, P., Holm, L. & Sander, C. (1994). The immunoglobulin fold. Structural classification, sequence patterns and common core. *J Mol Biol* 242, 309-20.
20. Kjeldsen, T., Clausen, H., Hirohashi, S., Ogawa, T., Iijima, H. & Hakomori, S. (1988). Preparation and characterization of monoclonal antibodies directed to the tumor-associated O-linked sialosyl-2----6 alpha-N-acetylgalactosaminyl (sialosyl-Tn) epitope. *Cancer Res* 48, 2214-20.
21. Senisterra, G. A. & Finerty, P. J., Jr. (2009). High throughput methods of assessing protein stability and aggregation. *Mol Biosyst* 5, 217-23.
22. Lavinder, J. J., Hari, S. B., Sullivan, B. J. & Magliery, T. J. (2009). High-throughput thermal scanning: a general, rapid dye-binding thermal shift screen for protein engineering. *J Am Chem Soc* 131, 3794-5.
23. Kortt, A. A., Dolezal, O., Power, B. E., Hudson, P. J. (2001). Dimeric and trimeric antibodies: high avidity scFv for cancer targeting. Biomol Eng 18, 95-108.
24. Pini, A. & Bracci, L. (2000). Phage display of antibody fragments. Curr Protein Pept Sci 1, 155-69.
25. Durani, V., Sullivan, B. J., Magliery, T. J. (2012) Simplifying protein expression with ligation-free, traceless and tag-switching plasmids. Protein Expr Purif 85, 9-17.
26. Miroux, B., Walker, J. E. (1996) Over-production of proteins in *Escherichia coli*: mutant hosts that allow synthesis of some membrane proteins and globular proteins at high levels. J Mol Biol 260, 289-98.
27. Chen, C., Constantinou, A., Deonarain, M. (2011) Modulating antibody pharmacokinetics using hydrophilic polymers. Exper Opin Drug Deliv 8, 1221-36.
28. Veronese, F. M., Mero, A. (2008) The impact of PEGylation on biological therapies. BioDrugs 22, 315-29.
29. Goel, A., Colcher, D., Baranowska-Kortylewicz, et al. (2000) Genetically engineered tetravalent single-chain Fv of the pancarcinoma monoclonal antibody CC49: Improved biodistribution and potential for therapeutic application. Cancer Res 60, 6964-71.
30. Bailey, G. S. (1996) The Iodogen Method for Radiolabeling Protein, Humana Press Inc., Totowa, N.J.
31. Paus, E. B., O.; Nustad, K. (1982) Radioiodination of proteins with the Iodogen method, International Atomic Energy Agency, Vienna.
32. Maddalena, M. E., Fox, J., Chen, J., Feng, W., Cagnolini, A., Linder, K. E., Tweedle, M. F., Nunn, A. D., and Lantry, L. E. (2009) 177Lu-AMBA biodistribution, radiotherapeutic efficacy, imaging, and autoradiography in prostate cancer models with low GRP-R expression. Journal of nuclear medicine: official publication, Society of Nuclear Medicine 50, 2017-24
33. Wedeking, P., and Tweedle, M. (1988) Comparison of the Biodistribution of Gd-153-Labeled Gd(Dtpa)2-, Gd(Dota)-, and Gd(Acetate)N in Mice. Nuclear medicine and biology 15, 395-402.

SEQUENCES (3E8.scFv)

SEQ ID NO: 1

MKYLLPTAAAGLLLLAAQPAMAAHHHHHHGSSGGGENLYFQGSSGDI
VMTQSPDSLAVSLGERATINCKSSQSVLYSSNNKNYLAWYQQKPGQPPKL
LIYWASTRESGVPDRFSGSGSGTDFTLTISSLQAEDVAVYYCQQYYSYPL
TFGGGTKVEIKLSADDAKKDAAKKDDAKKDDAKKDLQVQLVQSGAEVKKP
GASVKVSCKASGYTFTDHAIHWVRQAPGQRLEWMGYFSPGNDDFKYSQKF
QGRVTITADKSASTAYMELSSLRSEDTAVYYCARSWIMQYWGQGTLVTVS
S (3E8.scFv.Cys)

SEQ ID NO: 2

MKYLLPTAAAGLLLLAAQPAMAAHHHHHHGSSGGGENLYFQGSSGDI
VMTQSPDSLAVSLGERATINCKSSQSVLYSSNNKNYLAWYQQKPGQPPKL
LIYWASTRESGVPDRFSGSGSGTDFTLTISSLQAEDVAVYYCQQYYSYPL
TFGGGTKVEIKLSADDAKKDAAKKDDAKKDDAKKDLQVQLVQSGAEVKKP
GASVKVSCKASGYTFTDHAIHWVRQAPGQRLEWMGYFSPGNDDFKYSQKF
QGRVTITADKSASTAYMELSSLRSEDTAVYYCARSWIMQYWGQGTLVTVS
SC

SEQ ID NO: 3

MKYLLPTAAAGLLLLAAQPAMA

SEQ ID NO: 4

AHHHHHHGSSGGGENLYFQ

SEQ ID NO: 5

GSSG

SEQ ID NO: 6

LSADDAKKDAAKKDDAKKDDAKKDL (3E8.scFv)

SEQ ID NO: 7

CATATGAAATATCTGTTACCTACTGCTGCTGCGGGCCTGCTATTATTA
GCGGCACAACCAGCAATGGCGGCGCATCATCATCATCATCATGGGTCCTC
GGGCGGTGGCGAAAATCTGTATTTTCAGGGTAGCAGCGGCGATATTGTGA
TGACCCAGAGCCCGGATAGTTTGGCCGTTAGCCTGGGCGAACGTGCGACG
ATTAATTGCAAGAGCAGCCAGAGCGTGCTTTACAGCAGCAACAATAAGAA
TTACCTGGCGTGGTATCAGCAAAAACCCGGCCAGCCGCCGAAACTTTTGA
TTTATTGGGCGAGCACCCGTGAAAGCGGCGTGCCGGATCGTTTCTCGGGC

-continued

| SEQUENCES |
|---|
| TCAGGCAGCGGGACCGATTTTACGCTGACCATCAGCAGCCTTCAGGCGGA |
| GGATGTCGCGGTGTACTACTGCCAGCAGTATTACAGCTATCCGTTGACCT |
| TTGGGGGAGGCACCAAAGTGGAGATCAAACTGAGCGCGGATGATGCTAAG |
| AAAGATGCGGCGAAGAAGGACGATGCGAAAAAAGACGACGCAAAAAAGGA |
| TCTGCAGGTGCAGCTGGTGCAGTCGGGTGCGGAAGTGAAGAAACCTGGGG |
| CGTCGGTGAAAGTGAGCTGCAAAGCGAGCGGCTATACCTTTACCGATCAT |
| GCGATTCATTGGGTGCGTCAAGCGCCAGGCCAGCGTCTGGAATGGATGGG |
| CTATTTTTCCCCAGGCAACGATGATTTCAAGTATTCCCAGAAGTTCCAAG |
| GGCGCGTGACCATTACCGCCGATAAAAGCGCAAGCACCGCGTATATGGAG |
| CTGTCCAGCCTGCGTAGCGAAGATACAGCGGTTTACTATTGCGCACGGAG |
| CTGGATTATGCAATACTGGGGCCAGGGCACCCTGGTGACCGTGAGCAGCT |
| AAGGATCC |
| (3E8.scFv.Cys)<br>SEQ ID NO: 8<br>CATATGAAATATCTGTTACCTACTGCTGCTGCGGGCCTGCTATTATTA |
| GCGGCACAACCAGCAATGGCGGCGCATCATCATCATCATCATGGGTCCTC |
| GGGCGGTGGCGAAAATCTGTATTTTCAGGGTAGCAGCGGCGATATTGTGA |
| TGACCCAGAGCCCGGATAGTTTGGCCGTTAGCCTGGGCGAACGTGCGACG |
| ATTAATTGCAAGAGCAGCCAGAGCGTGCTTTACAGCAGCAACAATAAGAA |
| TTACCTGGCGTGGTATCAGCAAAAACCCGGCCAGCCGCCGAAACTTTTGA |
| TTTATTGGGCGAGCACCCGTGAAAGCGGCGTGCCGGATCGTTTCTCGGGC |

-continued

| SEQUENCES |
|---|
| TCAGGCAGCGGGACCGATTTTACGCTGACCATCAGCAGCCTTCAGGCGGA |
| GGATGTCGCGGTGTACTACTGCCAGCAGTATTACAGCTATCCGTTGACCT |
| TTGGGGGAGGCACCAAAGTGGAGATCAAACTGAGCGCGGATGATGCTAAG |
| AAAGATGCGGCGAAGAAGGACGATGCGAAAAAAGACGACGCAAAAAAGGA |
| TCTGCAGGTGCAGCTGGTGCAGTCGGGTGCGGAAGTGAAGAAACCTGGGG |
| CGTCGGTGAAAGTGAGCTGCAAAGCGAGCGGCTATACCTTTACCGATCAT |
| GCGATTCATTGGGTGCGTCAAGCGCCAGGCCAGCGTCTGGAATGGATGGG |
| CTATTTTTCCCCAGGCAACGATGATTTCAAGTATTCCCAGAAGTTCCAAG |
| GGCGCGTGACCATTACCGCCGATAAAAGCGCAAGCACCGCGTATATGGAG |
| CTGTCCAGCCTGCGTAGCGAAGATACAGCGGTTTACTATTGCGCACGGAG |
| CTGGATTATGCAATACTGGGGCCAGGGCACCCTGGTGACCGTGAGCAGCT |
| GTTAAGGATCC |
| SEQ ID NO: 9<br>MKYLLPTAAAGLLLLAAQPAMAAHHHHHHGSSGGGENLYFQGSSGDIV |
| (VH Domain)<br>SEQ ID NO: 10<br>QVQLVQSGAEVKKPGASVKVSCKASGYTFTDHAIHWVRQAPGQRLE<br>WMGYFSPGNDDFKYSQKFQGRVTITADKSSSTAYMELSSLRSEDTAVYY<br>CARSWIMQYWGQGTLVTVSS |
| (VL Domain)<br>SEQ ID NO: 11<br>DIVMTQSPDSLAVSLGERATINCKSSQSVLYSSNNKNYLAWYQQKPG<br>QPPKLLIYWASTRESGVPDRFSGSGSGTDFTLTISSLQAEDVAVYYCQQ<br>YYSYPLTFGGGTKVEIK |

What is claimed is:

1. An antibody fragment which specifically binds tumor-associated glycoprotein 72 (TAG-72), wherein the antibody fragment comprises SEQ ID NO: 1 or SEQ ID NO: 2.

2. A nucleic acid sequence encoding an antibody fragment comprising SEQ ID NO: 1 or SEQ ID NO: 2.

3. A vector comprising a nucleic acid sequence encoding an antibody fragment comprising SEQ ID NO: 1 or SEQ ID NO: 2.

4. The vector according to claim 3, wherein said vector is a bare nucleic acid segment, a carrier-associated nucleic acid segment, a nucleoprotein, a plasmid, a virus, a viroid, or a transposable element.

5. An isolated cell that produces the antibody fragment comprising SEQ ID NO: 1 or SEQ ID NO: 2.

6. A composition comprising an antibody fragment comprising SEQ ID NO: 1 or SEQ ID NO: 2 and a pharmaceutically acceptable carrier.

7. A composition comprising an antibody fragment comprising SEQ ID NO: 1 or SEQ ID NO: 2, wherein the antibody fragment is directly or indirectly attached to an effector moiety.

8. The composition of claim 7, wherein said effector moiety is a radionuclide, therapeutic enzyme, anti-cancer drug, cytokine, cytotoxin, or anti-proliferative agent.

9. The composition of claim 7, wherein the effector moiety is a detectable label, and the composition is suitable for detection of cancer.

10. The composition of claim 9, wherein the detectable label is a radionuclide or an enzyme.

11. The composition of claim 9, wherein the cancer is colon cancer, colorectal cancer, gastric cancer, an adenocarcinoma, esophageal cancer, pancreatic cancer, endometrial cancer, ovarian cancer, lung cancer, prostate cancer, and breast cancer.

12. A method of in vivo immunodetection of TAG-72-expressing cancer cells in a mammal comprising a step of administering to the mammal a diagnostically effective amount of a composition comprising an antibody fragment comprising SEQ ID NO: 1 or SEQ ID NO: 2, wherein the antibody fragment is directly or indirectly attached to a radionuclide.

13. The method of claim 12, wherein said immunodetection is in vivo tumor imaging.

14. The method of claim 12, wherein the radionuclide is $^{43}$K, $^{52}$Fe, $^{57}$Co, $^{67}$Cu, $^{67}$Ga, $^{68}$Ga, $^{77}$Br, $^{81}$Rb/$^{81}$MKr, $^{87M}$Sr, $^{99M}$Tc, $^{111}$In, $^{113}$In, $^{123}$I, $^{124}$I, $^{125}$I, $^{127}$Cs, $^{129}$Cs, $^{131}$I, $^{132}$I, $^{197}$Hg, $^{203}$Pb, $^{64}$Cu, or $^{206}$Bi.

15. A method of treating cancer expressing TAG-72 comprising administering to a subject in need thereof a composition comprising an antibody fragment comprising SEQ ID NO: 1 or SEQ ID NO: 2, wherein the antibody fragment is directly or indirectly attached to an effector moiety.

16. The method of claim 15, wherein the effector moiety is a chemotherapeutic agent selected from the group consisting of an anti-tumor drug, a cytokine, an anti-metabolite, an alkylating agent, a hormone, methotrexate, doxorubicin, daunorubicin, cytosine arabinoside, etoposide, 5-fluorouracil, melphalan, chlorambucil, a nitrogen mustard, cyclophosphamide, cis-platinum, vindesine, vinca alkaloids, mitomycin, bleomycin, purothionin, macromomycin, 1,4-benzoquinone derivatives, trenimon, steroids, aminopterin, anthracyclines, demecolcine, mithramycin, daunomycin, vinblastine, neocarzinostatin, macromycin, a-amanitin, and combinations thereof.

17. The method of claim 16, further comprising administering to the subject one or more additional anti-tumor treatments.

18. The method of claim 17, wherein the one or more additional anti-tumor treatments are selected from the group consisting of radiotherapy, chemotherapy, an additional immunotherapy, an anti-inflammatory therapy, and combinations thereof.

19. The method of claim 17, wherein the one or more additional anti-tumor therapies comprise administering gemcitabine (4-amino-1-(2-deoxy-2,2-difluoro- -D-eiyi/7ro-pentofuranosyl)pyrimidin-2(1 H)-on-2',2'-difluoro-2'-deoxycytidine) and celecoxib (4-[5-(4-methylphenyl)-3-(trifluoromethyl)pyrazol-1-yl]benzenesulfonamide), or pharmaceutically acceptable salts of either or both thereof, to the subject.

* * * * *

SEQUENCE LISTING

<160> NUMBER OF SEQ ID NOS: 11

<210> SEQ ID NO 1
<211> LENGTH: 298
<212> TYPE: PRT
<213> ORGANISM: Artificial Sequence
<220> FEATURE:
<223> OTHER INFORMATION: Synthesized

<400> SEQUENCE: 1

```
Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110
```

```
Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Leu Ser
145                 150                 155                 160

Ala Asp Asp Ala Lys Lys Asp Ala Ala Lys Lys Asp Asp Ala Lys Lys
                165                 170                 175

Asp Asp Ala Lys Lys Asp Leu Gln Val Gln Leu Val Gln Ser Gly Ala
            180                 185                 190

Glu Val Lys Lys Pro Gly Ala Ser Val Lys Val Ser Cys Lys Ala Ser
        195                 200                 205

Gly Tyr Thr Phe Thr Asp His Ala Ile His Trp Val Arg Gln Ala Pro
    210                 215                 220

Gly Gln Arg Leu Glu Trp Met Gly Tyr Phe Ser Pro Gly Asn Asp Asp
225                 230                 235                 240

Phe Lys Tyr Ser Gln Lys Phe Gln Gly Arg Val Thr Ile Thr Ala Asp
                245                 250                 255

Lys Ser Ala Ser Thr Ala Tyr Met Glu Leu Ser Ser Leu Arg Ser Glu
            260                 265                 270

Asp Thr Ala Val Tyr Tyr Cys Ala Arg Ser Trp Ile Met Gln Tyr Trp
        275                 280                 285

Gly Gln Gly Thr Leu Val Thr Val Ser Ser
    290                 295


<210> SEQ ID NO 2
<211> LENGTH: 299
<212> TYPE: PRT
<213> ORGANISM: Artificial Sequence
<220> FEATURE:
<223> OTHER INFORMATION: Synthesized

<400> SEQUENCE: 2

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45

Met Thr Gln Ser Pro Asp Ser Leu Ala Val Ser Leu Gly Glu Arg Ala
    50                  55                  60

Thr Ile Asn Cys Lys Ser Ser Gln Ser Val Leu Tyr Ser Ser Asn Asn
65                  70                  75                  80

Lys Asn Tyr Leu Ala Trp Tyr Gln Gln Lys Pro Gly Gln Pro Pro Lys
                85                  90                  95

Leu Leu Ile Tyr Trp Ala Ser Thr Arg Glu Ser Gly Val Pro Asp Arg
            100                 105                 110

Phe Ser Gly Ser Gly Ser Gly Thr Asp Phe Thr Leu Thr Ile Ser Ser
        115                 120                 125

Leu Gln Ala Glu Asp Val Ala Val Tyr Tyr Cys Gln Gln Tyr Tyr Ser
    130                 135                 140

Tyr Pro Leu Thr Phe Gly Gly Gly Thr Lys Val Glu Ile Lys Leu Ser
145                 150                 155                 160

Ala Asp Asp Ala Lys Lys Asp Ala Ala Lys Lys Asp Asp Ala Lys Lys
                165                 170                 175
```

```
Asp Asp Ala Lys Lys Asp Leu Gln Val Gln Leu Val Gln Ser Gly Ala
            180                 185                 190

Glu Val Lys Lys Pro Gly Ala Ser Val Lys Val Ser Cys Lys Ala Ser
        195                 200                 205

Gly Tyr Thr Phe Thr Asp His Ala Ile His Trp Val Arg Gln Ala Pro
    210                 215                 220

Gly Gln Arg Leu Glu Trp Met Gly Tyr Phe Ser Pro Gly Asn Asp Asp
225                 230                 235                 240

Phe Lys Tyr Ser Gln Lys Phe Gln Gly Arg Val Thr Ile Thr Ala Asp
                245                 250                 255

Lys Ser Ala Ser Thr Ala Tyr Met Glu Leu Ser Ser Leu Arg Ser Glu
            260                 265                 270

Asp Thr Ala Val Tyr Tyr Cys Ala Arg Ser Trp Ile Met Gln Tyr Trp
        275                 280                 285

Gly Gln Gly Thr Leu Val Thr Val Ser Ser Cys
    290                 295


<210> SEQ ID NO 3
<211> LENGTH: 22
<212> TYPE: PRT
<213> ORGANISM: Artificial Sequence
<220> FEATURE:
<223> OTHER INFORMATION: Synthesized

<400> SEQUENCE: 3

Met Lys Tyr Leu Leu Pro Thr Ala Ala Ala Gly Leu Leu Leu Leu Ala
1               5                   10                  15

Ala Gln Pro Ala Met Ala
            20


<210> SEQ ID NO 4
<211> LENGTH: 19
<212> TYPE: PRT
<213> ORGANISM: Artificial Sequence
<220> FEATURE:
<223> OTHER INFORMATION: Synthesized

<400> SEQUENCE: 4

Ala His His His His His His Gly Ser Ser Gly Gly Gly Glu Asn Leu
1               5                   10                  15

Tyr Phe Gln


<210> SEQ ID NO 5
<211> LENGTH: 4
<212> TYPE: PRT
<213> ORGANISM: Artificial Sequence
<220> FEATURE:
<223> OTHER INFORMATION: Synthesized

<400> SEQUENCE: 5

Gly Ser Ser Gly
1


<210> SEQ ID NO 6
<211> LENGTH: 25
<212> TYPE: PRT
<213> ORGANISM: Artificial Sequence
<220> FEATURE:
<223> OTHER INFORMATION: Synthesized

<400> SEQUENCE: 6
```

```
Leu Ser Ala Asp Asp Ala Lys Lys Asp Ala Ala Lys Lys Asp Asp Ala
1               5                   10                  15

Lys Lys Asp Asp Ala Lys Lys Asp Leu
            20                  25


<210> SEQ ID NO 7
<211> LENGTH: 906
<212> TYPE: DNA
<213> ORGANISM: Artificial Sequence
<220> FEATURE:
<223> OTHER INFORMATION: Synthesized

<400> SEQUENCE: 7

catatgaaat atctgttacc tactgctgct gcgggcctgc tattattagc ggcacaacca      60

gcaatggcgg cgcatcatca tcatcatcat gggtcctcgg gcggtggcga aaatctgtat     120

tttcagggta gcagcggcga tattgtgatg acccagagcc cggatagttt ggccgttagc     180

ctgggcgaac gtgcgacgat taattgcaag agcagccaga gcgtgcttta cagcagcaac     240

aataagaatt acctggcgtg gtatcagcaa aaacccggcc agccgccgaa acttttgatt     300

tattgggcga gcacccgtga aagcggcgtg ccggatcgtt tctcgggctc aggcagcggg     360

accgatttta cgctgaccat cagcagcctt caggcggagg atgtcgcggt gtactactgc     420

cagcagtatt acagctatcc gttgaccttt gggggaggca ccaaagtgga gatcaaactg     480

agcgcggatg atgctaagaa agatgcggcg aagaaggacg atgcgaaaaa agacgacgca     540

aaaaaggatc tgcaggtgca gctggtgcag tcgggtgcgg aagtgaagaa acctggggcg     600

tcggtgaaag tgagctgcaa agcgagcggc tataccttta ccgatcatgc gattcattgg     660

gtgcgtcaag cgccaggcca gcgtctggaa tggatgggct atttttcccc aggcaacgat     720

gatttcaagt attcccagaa gttccaaggg cgcgtgacca ttaccgccga taaaagcgca     780

agcaccgcgt atatggagct gtccagcctg cgtagcgaag atacagcggt ttactattgc     840

gcacggagct ggattatgca atactggggc cagggcaccc tggtgaccgt gagcagctaa     900

ggatcc                                                                906


<210> SEQ ID NO 8
<211> LENGTH: 909
<212> TYPE: DNA
<213> ORGANISM: Artificial Sequence
<220> FEATURE:
<223> OTHER INFORMATION: Synthesized

<400> SEQUENCE: 8

catatgaaat atctgttacc tactgctgct gcgggcctgc tattattagc ggcacaacca      60

gcaatggcgg cgcatcatca tcatcatcat gggtcctcgg gcggtggcga aaatctgtat     120

tttcagggta gcagcggcga tattgtgatg acccagagcc cggatagttt ggccgttagc     180

ctgggcgaac gtgcgacgat taattgcaag agcagccaga gcgtgcttta cagcagcaac     240

aataagaatt acctggcgtg gtatcagcaa aaacccggcc agccgccgaa acttttgatt     300

tattgggcga gcacccgtga aagcggcgtg ccggatcgtt tctcgggctc aggcagcggg     360

accgatttta cgctgaccat cagcagcctt caggcggagg atgtcgcggt gtactactgc     420

cagcagtatt acagctatcc gttgaccttt gggggaggca ccaaagtgga gatcaaactg     480

agcgcggatg atgctaagaa agatgcggcg aagaaggacg atgcgaaaaa agacgacgca     540

aaaaaggatc tgcaggtgca gctggtgcag tcgggtgcgg aagtgaagaa acctggggcg     600

tcggtgaaag tgagctgcaa agcgagcggc tataccttta ccgatcatgc gattcattgg     660
```

```
gtgcgtcaag cgccaggcca gcgtctggaa tggatgggct atttttcccc aggcaacgat    720

gatttcaagt attcccagaa gttccaaggg cgcgtgacca ttaccgccga taaaagcgca    780

agcaccgcgt atatggagct gtccagcctg cgtagcgaag atacagcggt ttactattgc    840

gcacggagct ggattatgca atactggggc cagggcaccc tggtgaccgt gagcagctgt    900

taaggatcc                                                            909


<210> SEQ ID NO 9
<211> LENGTH: 48
<212> TYPE: PRT
<213> ORGANISM: Artificial Sequence
<220> FEATURE:
<223> OTHER INFORMATION: Synthesized

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala Ala His His His His His His Gly Ser Ser
            20                  25                  30

Gly Gly Gly Glu Asn Leu Tyr Phe Gln Gly Ser Ser Gly Asp Ile Val
        35                  40                  45


<210> SEQ ID NO 10
<211> LENGTH: 115
<212> TYPE: PRT
<213> ORGANISM: Artificial Sequence
<220> FEATURE:
<223> OTHER INFORMATION: Synthesized

<400> SEQUENCE: 10

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Asp Asp Phe Lys Tyr Ser Gln Lys Phe
    50                  55                  60

Gln Gly Arg Val Thr Ile Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Trp Ile Met Gln Tyr Trp Gly Gln Gly Thr Leu Val Thr
            100                 105                 110

Val Ser Ser
        115


<210> SEQ ID NO 11
<211> LENGTH: 113
<212> TYPE: PRT
<213> ORGANISM: Artificial Sequence
<220> FEATURE:
<223> OTHER INFORMATION: Synthesized

<400> SEQUENCE: 11

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30
```

-continued

```
Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gly Gly Thr Lys Val Glu Ile
            100                 105                 110

Lys
```